United States Patent [19]

Sheldrake et al.

[11] Patent Number: 5,663,334
[45] Date of Patent: Sep. 2, 1997

[54] PROCESS FOR PREPARING PYRIMIDYL IMIDAZOLES

[75] Inventors: Peter William Sheldrake, Kent, England; Timothy Francis Gallagher, Harleysville; Joseph Sisko, Lansdale, both of Pa.

[73] Assignee: SmithKline Beecham Corporation, Philadelphia, Pa.

[21] Appl. No.: 702,250

[22] Filed: Aug. 21, 1996

Related U.S. Application Data

[63] Continuation of Ser. No. 472,366, Jun. 7, 1995, Pat. No. 5,593,992, which is a continuation-in-part of Ser. No. 369,964, Jan. 9, 1995, which is a continuation-in-part of Ser. No. 92,733, filed as PCT/US94/07969, Jul. 15, 1994, published as WO95/02591, Jan. 26, 1995, abandoned.

[51] Int. Cl.$^6$ .................. C07D 403/04; C07D 403/14; C07D 413/14
[52] U.S. Cl. .................. 544/122; 544/123; 544/316; 544/331; 544/333
[58] Field of Search .................. 544/122, 123, 544/316, 331

[56] References Cited

U.S. PATENT DOCUMENTS

| | | |
|---|---|---|
| 3,707,475 | 12/1972 | Lombardino . |
| 3,772,441 | 11/1973 | Lombardino . |
| 3,929,807 | 12/1975 | Fitzi . |
| 3,940,486 | 2/1976 | Fitzi . |
| 4,058,614 | 11/1977 | Baldwin . |
| 4,199,592 | 4/1980 | Cherkofsky . |
| 4,447,431 | 5/1984 | Sallmann . |
| 4,503,065 | 3/1985 | Wilkerson . |
| 4,565,875 | 1/1986 | Cavender . |
| 4,686,231 | 8/1987 | Bender et al. . |
| 4,822,805 | 4/1989 | Tasasugi et al. . |

FOREIGN PATENT DOCUMENTS

| | | |
|---|---|---|
| WO 92/10498 | 6/1992 | WIPO . |
| WO 92/10190 | 6/1992 | WIPO . |
| WO95/02591 | 1/1995 | WIPO . |

OTHER PUBLICATIONS

Dinarello et al., Rev. Infect. Disease, 6, p. 51 (1984).
Dinarello, J. Clin. Immun., 5(5), pp. 287–297 (1985).
R.P. Soni, Aust. J. Chem., 35, pp. 1493–1496 (1982).
Poli et al., Proc. Nat'l Acad. Sci., 87, pp. 782–784 (1990).
VanLeusen et al., J.O.C., 42, p. 1153 (1977).
Kumada et al., Tetrahedron Letters, 22, p. 5319 (1981).
Pridgen, J. Org. Chem., 47, p. 4319 (1982).
Stille, J. Amer. Chem. Soc., 109, p. 5478 (1978).
Fischer et al., Rec. Trav. Chim. Pays. Bas., 84, p. 439 (1965).
Snieckus, V., Tetrahedron Letters, 29, 2135 (1988).
Terashimia, M., Chem. Pharm. Bull., 11, p. 4755 (1985).
Thompson, W.J., et al., J. Org. Chem., 49, p. 5237 (1984).
Garigipati, R., Tetrahedron Letters, 31, p. 190 (1989).
Engel & Steglich, Liebigs Ann. Chem., 1916 (1978).
Strzybny et al., J. Org. Chem., 28, p. 3381 (1963).
Zavyalov, et al., Khim Farm Zh, 26(3), p. 88 (1992).
Colotta et al., J. Immunol., 132(2), p. 936 (1984).
Simon et al., J. Immunol. Methods, 84, p. 85 (1985).
Becker et al., J. Immunol., 147, p. 4307 (1991).
Gilbert, Synthesis, pp. 30–32 (1972).
Morton et al., Tetrahedron Letters, 4123 (1982).
Armarego, W. J. Chem. Soc., (JCSOA9) p. 561 (1962).

*Primary Examiner*—Robert W. Ramsuer
*Attorney, Agent, or Firm*—Dara L. Dinner; Stephen Venetianer; Edward T. Lentz

[57] ABSTRACT

Novel 1,4,5-substituted imidazole compounds and compositions for use in therapy as cytokine inhibitors.

29 Claims, No Drawings

PROCESS FOR PREPARING PYRIMIDYL IMIDAZOLES

This is a continuation of application U.S. Ser. No. 08/472,366, filed 7 Jun. 1995, now U.S. Pat. No. 5,593,992, which is a continuation in part application of U.S. Ser. No. 08/369,964, filed 9 Jan. 1995, which is a continuation in part application of PCT/US94/07969 filed 15 Jul. 1994, which is a continuation in part application of U.S. Ser. No. 08/092,733, filed 16 Jul. 1993, now abandoned.

This invention relates to a novel group of imidazole compounds, processes for the preparation thereof, the use thereof in treating cytokine mediated diseases and pharmaceutical compositions for use in such therapy.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et al., Proc. Natl. Acad. Sci., 87:782–784 (1990)], therefore, inhibition of monokine production or activity aids in limiting HIV progression as stated above for T-cells.

TNF has also been implicated in various roles with other viral infections, such as the cytomegalia virus (CMV), influenza virus, and the herpes virus for similar reasons as those noted.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide CLPS). Human IL-8 has been shown to act on Mouse, Guinea Pig, Rat, and Rabbit Neutrophils. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are cytokine suppressive anti-inflammatory drugs, i.e. compounds which are capable of inhibiting cytokines, such as IL-1, IL-6, IL-8 and TNF.

SUMMARY OF THE INVENTION

This invention relates to the novel compounds of Formula (I) and pharmaceutical compositions comprising a compound of Formula (I) and a pharmaceutically acceptable diluent or carrier.

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides a compound of Formula (I):

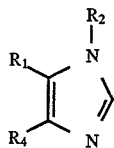

(I)

$R_1$ is 4-pyridyl, pyrimidinyl, quinolyl, isoquinolinyl, quinazolin-4-yl, 1-imidazolyl or 1-benzimidazolyl, which heteroaryl ring is optionally substituted with one or two substituents each of which is independently selected from $C_{1-4}$ alkyl, halogen, hydroxyl, $C_{1-4}$ alkoxy; $C_{1-4}$ alkylthio, $C_{1-4}$ alkylsulfinyl, $CH_2OR_{12}$, amino, mono and di- $C_{1-6}$ alkyl substituted amino, $N(R_{10})C(O)R_a$ or an N-heterocyclyl ring which ring has from 5 to 7 members and optionally contains an additional heteroatom selected from oxygen, sulfur or $NR_{15}$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $-C(Z)NR_7R_{17}$, $-C(Z)OR_{16}$, $-(CR_{10}R_{20})_vCOR_{12}$, $-SR_5$, $-SOR_5$, $-OR_{12}$, halo-substituted-$C_{1-4}$ alkyl, $C_{1-4}$ alkyl, $-ZC(Z)R_{12}$, $-NR_{10}C(Z)R_{16}$, or $-(CR_{10}R_{20})_vNR_{10}R_{20}$ and which, for other positions of substitution, is halogen, cyano, $-C(Z)NR_{13}R_{14}$, $-C(Z)OR_3$, $-(CR_{10}R_{20})_{m''}COR_3$, $-S(O)mR_3$, $-OR_3$, $-OR_{12}$, halo substituted $C_{1-4}$ alkyl, $C_{1-4}$ alkyl, $-(CR_{10}R_{20})_{m''}NR_{10}C(Z)R_3$, $-NR_{10}S(O)_mR_8$, $-NR_{10}S(O)_mNR_7R_{17}$, $-ZC(Z)R_3$, $-ZC(Z)R_{12}$, or $-(CR_{10}R_{20})_{m''}NR_{13}R_{14}$;

v is 0, or an integer having a value of 1 or 2;

m is 0, or the integer 1 or 2;

m' is an integer having a value of 1 or 2, m'' is 0, or an integer having a value of 1 to 5;

$R_2$ is $C_{1-10}$ alkyl $N_3$, $-(CR_{10}R_{20})_{n'}OR_9$, heterocyclyl, heterocyclyl$C_{1-10}$alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl$C_{1-10}$alkyl, aryl, aryl$C_{1-10}$alkyl, heteroaryl, heteroaryl$C_{1-10}$alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_mNR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups may be optionally substituted;

n is an integer having a value of 1 to 10;

n' is 0, or an integer having a value of 1 to 10;

Z is oxygen or sulfur;

Ra is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $-SR_5$ being $-SNR_7R_{17}$ and $-S(O)R_5$ being $-SOH$;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$_{1-10}$alkyl, heterocyclyl, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)2R_{18}$, $(CR_{10}R_{20})_nNR_{13}R_{14}$; wherein the aryl, arylalkyl, heteroaryl, heteroaryl alkyl may be optionally substituted;

$R_9$ is hydrogen, $-C(Z)R_{11}$, optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)-C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl 1-10alkyl, heterocyclyl, heterocyclyl-$C_{1-10}$alkyl, heteroaryl or heteroaryl 1-10alkyl;

$R_{19}$ is hydrogen, cyano, $C_{1-4}$ alkyl, $C_{3-7}$ cycloalkyl or aryl;

or a pharmaceutically acceptable salt thereof.

DETAILED DESCRIPTION OF THE INVENTION

The novel compounds of Formula (I) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

In Formula (I), suitable $R_1$ moieties includes 4-pyridyl, 4-pyrimidinyl, 4-quinolyl, 6-isoquinolinyl, 4-quinazolinyl, 1-imidazolyl and 1-benzimidazolyl, of which the 4-pyridyl, 4-pyrimidinyl and 4-quinolyl are preferred. More preferred is an optionally substituted 4-pyrimidinyl or optionally substituted 4-pyridyl moiety, and most preferred is an optionally substituted 4-pyrimidinyl ring.

Suitable substituents for the $R_1$ heteroaryl rings are $C_{1-4}$ alkyl, halo, OH, $C_{1-4}$ alkoxy, $C_{1-4}$ alkylthio, $C_{1-4}$ alkylsulfinyl, $CH_2OR_{12}$, amino, mono- and di-$C_{1-6}$ alkyl-substituted amino, $N(R_{10})C(O)R_a$ or an N-heterocyclyl ring which ring has from 5 to 7 members and optionally contains an additional heteroatom selected from oxygen, sulfur or $NR_{15}$. A preferred substituent for all the $R_1$ moieties is $C_{1-4}$ alkyl, in particular methyl, amino, and mono- and di-$C_{1-6}$ alkylsubstituted amino, preferably where the amino group is mono-substituted, more preferably with methyl. The alkyl group in the mono- and di-$C_{1-6}$ alkylsubstituted amino moiety may be halo substituted, such as in trifluoro- i.e., trifluoromethyl or trifluroethyl.

When the $R_1$ optional substituent is $N(R_{10})C(O)R_a$, wherein $R_a$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl, $R_a$ is preferably $C_{1-6}$ alkyl; preferably $R_{10}$ is hydrogen. It is also recognized that the $R_a$ moieties, in particular the $C_{1-6}$ alkyl group may be optionally substituted, preferably from one to three times, preferably with halogen, such as fluorine, as in trifluoromethyl or trifluroethyl.

Preferably, the preferred substituent for $R_1$ is the amino or mono $C_{1-6}$ alkyl substituted moiety. A preferred ring placement of the $R_1$ substituent on the 4-pyridyl derivative is the 2-position, such as 2-methyl-4-pyridyl. A preferred ring placement on the 4-pyrimidinyl ring is also at the 2-position, such as in 2-methyl-pyrimidinyl, 2-amino pyrimidinyl or 2-methylaminopyrimidinyl.

Suitably, $R_4$ is phenyl, naphth-1-yl or naphth-2-yl, or a heteroaryl, which is optionally substituted by one or two substituents. More preferably $R_4$ is a phenyl or naphthyl ring. Suitable substitutions for $R_4$ when this is a 4-phenyl, 4-naphth-1-yl, 5-naphth-2-yl or 6-naphth-2-yl moiety are one or two substituents each of which are independently selected from halogen, $-SR_5$, $-SOR_5$, $-OR_{12}$, $CF_3$, or $-(CR_{10}R_{20})_v NR_{10}R_{20}$, and for other positions of substitution on these rings preferred substitution is halogen, $-S(O)_mR_3$, $-OR_3$, $CF_3$, $-(CR_{10}R_{20})_m$"$NR_{13}R_{14}$, $-NR_{10}C(Z)R_3$ and $-NR_{10}S(O)_m$'$R_8$. Preferred substituents for the 4-position in phenyl and naphth-1-yl and on the 5-position in naphth-2-yl include halogen, especially fluoro and chloro and $-SR_5$ and $-SOR_5$ wherein $R_5$ is preferably a $C_{1-2}$ alkyl, more preferably methyl; of which the fluoro and chloro is more preferred, and most especially preferred is fluoro. Preferred substituents for the 3-position in phenyl and naphth-1-yl rings include: halogen, especially fluoro and chloro; $-OR_3$, especially $C_{1-4}$ alkoxy; $CF_3$, $NR_{10}R_{20}$, such as amino; $-NR_{10}C(Z)R_3$, especially $-NHCO(C_{1-10}$ alkyl); $-NR_{10}S(O)_m R_8$, especially $-NHSO_2(C_{1-10}$ alkyl), and $-SR_3$ and $-SOR_3$ wherein $R_3$ is preferably a $C_{1-2}$ alkyl, more preferably methyl. When the phenyl ring is disubstituted preferably it is two independent halogen moieties, such as fluoro and chloro, preferably di-chloro and more preferably in the 3,4-position. It is also preferred that for the 3-position of both the $-OR_3$ and $-ZC(Z)R_3$ moieties, $R_3$ may also include hydrogen.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methane-sulfonamido or acetamido, or $R_4$ is a phenyl di-substituted at the 3,4-position independently with chloro or fluoro, more preferably chloro. Most preferably, $R_4$ is a 4-fluorophenyl.

In Formula (I), Z is oxygen or sulfur, preferably oxygen.

Suitably, $R_2$ is $C_{1-10}$ alkyl $N_3$, $-(CR_{10}R_{20})_n OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl; $(CR_{10}R_{20})_n OR_{11}$, $(CR_{10}R_{20})_n S(O)_m R_{18}$, $(CR_{10}R_{20})_n NHS(O)_2 R_{18}$, $(CR_{10}R_{20})_n NR_{13}R_{14}$, $(CR_{10}R_{20})_n NO_2$, $(CR_{10}R_{20})_n CN$, $(CR_{10}R_{20})_n \cdot SO_2 R_{18}$, $(CR_{10}R_{20})_n S(O)_m \cdot NR_{13}R_{14}$, $(CR_{10}R_{20})_n C(Z)R_{11}$, $(CR_{10}R_{20})_n OC(Z)R_{11}$, $(CR_{10}R_{20})_n C(Z)OR_{11}$, $(CR_{10}R_{20})_n C(Z)NR_{13}R_{14}$, $(CR_{10}R_{20})_n C(Z)NR_{11}OR_9$, $(CR_{10}R_{20})_n NR_{10}C(Z)R_{11}$, $(CR_{10}R_{20})_n NR_{10}C(Z)NR_{13}R_{14}$, $(CR_{10}R_{20})_n N(OR_6)C(Z)NR_{13}R_{14}$, $(CR_{10}R_{20})_n N(OR_6)C(Z)R_{11}$, $(CR_{10}R_{20})_n C(=NOR_6)R_{11}$, $(CR_{10}R_{20})_n NR_{10}C(=NR_{19})NR_{13}R_{14}$, $(CR_{10}R_{20})_n OC(Z)NR_{13}R_{14}$, $(CR_{10}R_{20})_n NR_{10}C(Z)NR_{13}R_{14}$, $(CR_{10}R_{20})_n NR_{10}C(Z)OR_{10}$, 5-($R_{18}$)-1,2,4-oxadiazol-3-yl or 4-($R_{12}$)-5-($R_{18}R_{19}$)-4,5-dihydro-1,2,4-oxadiazol-3-yl; wherein the cycloalkyl, cycloalkylalkyl, aryl, arylalkyl, heteroaryl, heteroarylalkyl, heterocyclic, and heterocyclic alkyl moieties may be optionally substituted; wherein n is an integer having a value of 1 to 10, m is 0, or the integer 1 or 2; n' is 0, or an integer having a value of 1 to 10; and m' is 1 or 2. Preferably n is 1 to 4.

Preferably $R_2$ is an optionally substituted heterocyclyl ring, and optionally substituted heterocyclyl$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{20})_n C(Z)OR_{11}$ group, $(CR_{10}R_{20})_n NR_{13}R_{14}$, $(CR_{10}R_{20})_n NHS(O)_2 R_{18}$, $(CR_{10}R_{20})_n S(O)_m R_{18}$, an optionally substituted aryl; an optionally substituted aryl$C_{1-10}$ alkyl, $(CR_{10}R_{20})_n OR_{11}$, $(CR_{10}R_{20})_n C(Z)R_{11}$, or $(CR_{10}R_{20})_n C(=NOR_6)R_{11}$ group.

More preferably $R_2$ is an optionally substituted heterocyclyl ring, and optionally substituted heterocyclyl$C_{1-10}$ alkyl, optionally substituted aryl, $(CR_{10}R_{20})_n NR_{13}R_{14}$, or $(CR_{10}R_{20})_n C(Z)OR_{11}$ group.

When $R_2$ is an optionally substituted heterocyclyl the ring is preferably a morpholino, pyrrolidinyl, or a piperidinyl group. When the ring is optionally substituted the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl—wherein the aryl or aryl alkyl moieties themselves may be optionally substituted (as in the definition section below);

$C(O)OR_{11}$, such as the $C(O)C_{1-4}$ alkyl or $C(O)OH$ moieties; $C(O)H$; $C(O)C_{1-4}$ alkyl, hydroxy substituted $C_{1-4}$ alkyl, $C_{1-4}$ alkoxy, $S(O)_mC_{1-4}$ alkyl (where m is 0, 1, or 2), $NR_{10}R_{20}$ (wherein $R_{10}$ and $R_{20}$ are independently hydrogen or $C_{1-4}$alkyl).

Preferably if the ring is a piperidine, the ring is attached to the imidazole at the 4-position, and the substituents are directly on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2 or 6 position or both, such as 2,2,6,6-tetramethyl-4-piperidine. Similarly, if the ring is a pyrrole, the ring is attached to the imidazole at the 3-position, and the substituents are all directly on the available nitrogen.

When $R_2$ is an optionally substituted heterocyclyl $C_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties. The heterocyclic ring herein is also optionally substituted in a similar manner to that indicated above for the direct attachment of the heterocyclyl.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_5$ to $C_6$ ring which ring may be optionally substituted 1 or more times independently by halogen, such as fluorine, chlorine, bromine or iodine; hydroxy; $C_{1-10}$ alkoxy, such as methoxy or ethoxy; $S(O)_m$ alkyl, wherein m is 0, 1, or 2, such as methyl thio, methylsulfinyl or methyl sulfonyl; amino, mono & di-substituted amino, such as in the $NR_7R_{17}$ group; or where the $R_7R_{17}$ may cyclize together with the nitrogen to which they are attached to form a 5 to 7 membered ring which optionally includes an additional heteroatom selected from O/N/S; $C_{1-10}$ alkyl, such as methyl, ethyl, propyl, isopropyl, or t-butyl; halosubstituted alkyl, such as $CF_3$; hydroxy substituted $C_{1-10}$alkyl; $C(O)OR_{11}$, such as the free acid or methyl ester derivative; an optionally substituted aryl, such as phenyl; an optionally substituted arylalkyl, such as benzyl of phenethyl; and further where these aryl moieties may also be substituted one to two times by halogen; hydroxy; $C_{1-10}$ alkoxy; $S(O)_m$alkyl; amino, mono & di-substituted amino, such as in the $NR_7R_{17}$ group; alkyl or halosubstituted alkyl.

When $R_2$ is $(CR_{10}R_{20})_nNR_{13}R_{14}$, $R_{13}$ and $R_{14}$ are as defined in Formula (I), that is $R_{13}$ and $R_{14}$ are each independently selected from hydrogen, optionally substituted $C_{1-4}$ alkyl, optionally substituted aryl or an optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$. It is recognized that in some instances this can yield the same moiety as a heterocyclic $C_{1-10}$ alkyl moiety noted above which is also a suitable $R_2$ variable. Preferably $R_{13}$ and $R_{14}$ are independently hydrogen, $C_{1-4}$ alkyl, preferably methyl, or benzyl. The n term is preferably 1 to 4, more preferably 3 or 4, and most preferably 3, such as in a propyl group. Preferred groups include, but are not limited to, aminopropyl; (N-methyl-N-benzyl)aminopropyl, (N-Phenylmethyl) amino-1-propyl, or diethylamino propyl.

When $R_2$ is a $(CR_{10}R_{20})_nC(Z)OR_{11}$ group, $R_{11}$ is suitably hydrogen, $C_{1-4}$ alkyl, especially methyl. The n term is preferably 1 to 4, more preferably 2 or 3, such as in an ethyl or propyl group. Preferred groups include, but are not limited to, carboxymethyl-1-butyl, carboxy-1-propyl, or 2-acetoxyethyl.

When $R_2$ is a $(CR_{10}R_{20})_nS(O)_mR_{18}$ group m is 0, 1, or 2, and $R_{18}$ is preferably aryl, especially phenyl, or $C_{1-10}$ alkyl, especially methyl. The n term is preferably 1 to 4, more preferably 2 or 3, such as in an ethyl or propyl group.

When $R_2$ is a $(CR_{10}R_{20})_nOR_{11}$ group, $R_{11}$ is suitably hydrogen, aryl, especially phenyl, or $C_{1-10}$ alkyl, especially methyl or ethyl. The n term is preferably 1 to 4, more preferably 2 or 3, such as in an ethyl or propyl group.

When $R_2$ is a $(CR_{10}R_{20})_nNHS(O)_2R_{18}$ group, $R_{18}$ is suitably alkyl, especially methyl. The n term is preferably 1 to 4, more preferably 2 or 3, such as in an ethyl or propyl group.

When $R_2$ is a optionally substituted aryl, the aryl is preferably phenyl. The aryl ring may be optionally substituted one or more times, preferably by one or two substituents, independently selected from $C_{1-4}$ alkyl, halogen, especially fluoro or chloro, $(CR_{10}R_{20})_tOR_{11}$, $—(CR_{10}R_{20})_tNR_{10}R_{20}$, especially amino or mono- or di-alkylamino $—(CR_{10}R_{20})_tS(O)_mR_{18}$, wherein m is 0, 1 or 2; —SH—, $—(CR_{10}R_{20})_nNR_{13}R_{14}$, $—NR_{10}C(Z)R_3$ (such —NHCO($C_{1-10}$ alkyl)); $—NR_{10}S(O)_mR_8$ (such as —NHSO$_2$($C_{1-10}$ alkyl)); and t is 0, or an integer of 1 to 4. Preferably the phenyl is substituted in the 3 or 4- position by $—(CR_{10}R_{20})_tS(O)_mR_{18}$, and $R_{18}$ is preferably $C_{1-10}$ alkyl, especially methyl.

When $R_2$ is an optionally substituted heteroaryl or heteroarylalkyl group the ring may be optionally substituted one or more times, preferably by one or two substituents, independently selected from one or more times, by $C_{1-4}$ alkyl, halogen, especially fluoro or chloro, $(CR_{10}R_{20})_tOR_{11}$, $—(CR_{10}R_{20})_tNR_{10}R_{20}$, especially amino or mono- or di-alkylamino $—(CR_{10}R_{20})_tS(O)_mR_{18}$, wherein m is 0, 1 or 2; —SH—, $—(CR_{10}R_{20})_n-NR_{13}R_{14}$, $—NR_{10}C(Z)R_3$ (such —NHCO($C_{1-10}$ alkyl)); $—NR_{10}S(O)_mR_8$ (such as —NHSO$_2$($C_{1-10}$ alkyl)); t is 0, or an integer of 1 to 4.

One skilled in the art would readily recognize that when $R_2$ is a $(CR_{10}R_{20})_nOC(Z)R_{11}$, or $(CR_{10}R_{20})_nOC(Z)NR_{13}R_{14}$ moiety, or any similarly substituted group that n is preferably at least 2 which will allow for the synthesis of stable compounds.

Preferably $R_2$ is a $C_{1-4}$ alkyl (branched and unbranched), especially methyl, methylthio propyl, a methylsulfinyl propyl, an amino propyl, N-methyl-N-benzylamino propyl group, diethylamino propyl, cyclopropyl methyl, morpholinyl butyl, morpholinyl propyl, a morpholinyl ethyl, a piperidine or a substituted piperidine. More preferably $R_2$ is a methyl, isopropyl, butyl, t-butyl, n-propyl, methylthiopropyl, or methylsulfinyl propyl, morpholino propyl, morpholinyl butyl, phenyl substituted by halogen, thioalkyl or sulfinyl alkyl such as a methylthio, methylsulfinyl or methylsulfonyl moiety; piperidinyl, 1-Formyl-4-piperidine, 1-benzyl-4-piperidine, 1-methyl-4-piperidine, or a 1-ethoxycarbonyl-4-piperidine.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in $OR_3$, or for certain $R_2$ moieties.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)$_m$alkyl, wherein m is 0, 1 or 2, such as methyl thio, methylsulfinyl or methyl sulfonyl; amino, mono & di-substituted amino, such as in the NR$_7$R$_{17}$ group; or where the R$_7$R$_{17}$ may together with the nitrogen to which they are attached cyclize to form a 5 to 7 membered ring which optionally includes an additional heteroatom selected from O/N/S; C$_{1-10}$ alkyl, cycloalkyl, or cycloalkyl alkyl group, such as methyl, ethyl, propyl, isopropyl, t-butyl, etc. or cyclopropyl methyl; halosubstituted C$_{1-10}$ alkyl, such CF$_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; C$_{1-10}$ alkoxy; S(O)$_m$ alkyl; amino, mono & di-substituted amino, such as in the NR$_7$R$_{17}$ group; alkyl, or CF$_3$.

In a preferred subgenus of compounds of Formula (I), R$_1$ is 4-pyridyl, 2-alkyl-4-pyridyl, 4-quinolyl, 4-pyrimidinyl, 2-amino-4-pyrimidinyl or 2-methylamino-4-pyrimidinyl; R$_2$ is morpholinyl propyl, aminopropyl, piperidinyl, N-benzyl-4-piperidinyl, or N-methyl-4-piperidinyl; and R$_4$ is phenyl or phenyl substituted one or two times by fluoro, chloro, C$_{1-4}$ alkoxy, —S(O)$_m$ alkyl, methanesulfonamido or acetamido.

A preferred subgrouping of compounds of Formula (I) are those where R$_2$ is other than methyl when R$_1$ is pyridyl, and R$_4$ is an optionally substituted phenyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo" or "halogens", include the halogens: chloro, fluoro, bromo and iodo.

"C$_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2-10carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl") —a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

The term "aralkyl" or "heteroarylalkyl" or "heterocyclicalkyl" is used herein to mean C$_{1-4}$ alkyl as defined above attached to an aryl, heteroaryl or heterocyclic moiety as also defined herein unless otherwise indicate.

"sulfinyl"—the oxide S (O) of the Corresponding sulfide, the term "thio" refers to the sulfide, and the term "sulfonyl" refers to the fully oxidized S (O)$_2$ moiety.

"aroyl"—a C(O)Ar, wherein Ar is as phenyl, naphthyl, or aryl alkyl derivative such as defined above, such group include but are not limited to benzyl and phenethyl.

"alkanoyl"—a C(O)C$_{1-10}$ alkyl wherein the alkyl is as defined above.

For the purposes herein the "core" 4-pyrimidinyl moiety for R$_1$ or R$_2$ is referred to as the formula:

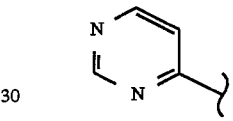

The compounds of the present invention may contain one or more asymmetric carbon atoms and may exist in racemic and optically active forms. All of these compounds are included within the scope of the present invention.

Exemplified compounds of Formula (I) include:

1-[3-(4-Morpholinyl)propyl]-4-(4-fluorophenyl)-5-(4-pyridyl)imidazole;

1-(3-Chloropropyl)-4-(4-fluorophenyl)-5-(4-pyridyl) imidazole;

1-(3-Azidopropyl)-4-(4-fluorophenyl)-5-(4-pyridyl) imidazole;

1-(3-Aminopropyl)-4-(4-fluorophenyl)-5-(4-pyridyl) imidazole;

1-(3-Methylsulfonamidopropyl)-4-(4-fluorophenyl)-5-(4-pyridyl)imidazole;

1-[3-(N-Phenylmethyl)aminopropyl]-4-(4-fluorophenyl)-5-(4-pyridyl)imidazole;

1-[3-(N-Phenylmethyl-N-methyl)aminopropyl)-4-(4-fluorophenyl)-5-(4-pyridyl)imidazole;

1-[3-(1-Pyrrolidinyl)propyl]-4-(4-fluorophenyl)-5-(4-pyridyl)imidazole;

1-(3-Diethylaminopropyl)-4-(4-fluorophenyl)-5-(4-pyridyl) imidazole;

1-[3-(1-Piperidinyl)propyl]-4-(4-fluorophenyl)-5-(4-pyridyl)imidazole;

1-[3-(Methylthio)propyl]-4-(4-fluorophenyl)-5-(4-pyridyl) imidazole;

1-[2-(4-Morpholinyl) ethyl]-4-(4-fluorophenyl)-5-(4-pyridyl)imidazole;

1-[3-(4-Morpholinyl)propyl]-4-(3-methylthiophenyl)-5-(4-pyridyl)imidazole;

(±)-1-[3-(4-Morpholinyl)propyl]-4-(3-methylsulfinylphenyl)-5-(4-pyridyl)imidazole;

1-[3-(N-methyl-N-benzyl)aminopropyl]-4-(3-methylthiophenyl)-5-(4-pyridyl)imidazole;

1-[3-(N-methyl-N-benzyl) aminopropyl]-4-(3-methylsulfinylphenyl)-5-(4-pyridyl)imidazole;
1-[4-(Methylthio)phenyl]-4-(4-fluorophenyl)-5-(4-pyridyl)imidazole;
1-[4-(Methylsulfinyl)phenyl]-4-(4-fluorophenyl)-5-(4-pyridyl)imidazole;
1-[3-(Methylthio)phenyl]-4-(4-fluorophenyl)-5-(4-pyridyl)imidazole;
(±)-1-[3-(Methylsulfinyl) phenyl]-4-(4-fluorophenyl)-5-(4-pyridyl)imidazole;
1-[2-(Methylthio)phenyl]-4-(4-fluorophenyl)-5-(4-pyridyl)imidazole;
1-[2-(Methylsulfinyl)phenyl]-4-(4-fluorophenyl)-5-(4-pyridyl)imidazole;
1-[4-(4-Morpholinyl)butyl]-4-(4-fluorophenyl)-5-(4-pyridyl)imidazole;
1-Cyclopropyl-4-(4-fluorophenyl)-5-(4-pyridyl)imidazole;
1-Isopropyl-4-(4-fluorophenyl)-5-(4-pyridyl)imidazole;
1-Cyclopropylmethyl-4-(4-fluorophenyl)-5-(4-pyridyl)imidazole;
1-tert-Butyl-4-(4-fluorophenyl)-5-(4-pyridyl)imidazole;
1-(2,2-Diethoxyethyl)-4-(4-fluorophenyl)-5-(4-pyridyl)imidazole;
1-Formylmethyl-4-(4-fluorophenyl)-5-(4-pyridyl)imidazole;
1-Hydroxyiminylmethyl-4-(4-fluorophenyl)-5-(4-pyridyl)imidazole;
1-Cyanomethyl-4-(4-fluorophenyl)-5-(4-pyridyl)imidazole;
1-[3-(4-Morpholinyl)propyl]-4-(4-fluorophenyl)-5-(2-methylpyrid-4-yl)imidazole;
4-(4-Fluorophenyl)-1-[3-(4-morpholinyl)propyl]-5-(2-chloropyridin-4-yl) imidazole;
4-(4-Fluorophenyl)-1-[3-(4-morpholinyl)propyl]-5-(2-amino-4-pyridinyl) imidazole;
1-(4-Carboxymethyl)propyl-4-(4-fluorophenyl)-5-(4-pyridyl)imidazole;
1-(4-Carboxypropyl)-4-(4-fluorophenyl)-5-(4-pyridyl)imidazole;
1-(3-Carboxymethyl)ethyl-4-(4-fluorophenyl)-5-(4-pyridyl)imidazole;
1-(3-Carboxy)ethyl-4-(4-fluorophenyl)-5-(4-pyridyl)imidazole;
1-(1-Benzylpiperidin-4-yl)-4-(4-fluorophenyl)-5-(4-pyridyl) imidazole;
5-(2-Aminopyrimidin-4-yl)-4-(4-fluorophenyl)-1-[3-(4-Morpholinyl)propyl]imidazole;
5-(2-Aminopyrimidin-4-yl)-4-(4-fluorophenyl)-1-(1-benzylpiperidin-4-yl)imidazole;
5-(2-Aminopyrimidin-4-yl)-4-(4-fluorophenyl)-1-(2-propyl)imidazole;
5-(2-Aminopyrimidin-4-yl)-4-(4-fluorophenyl)-1-(cyclopropylmethyl)imidazole;
5-(2-Aminopyrimidin-4-yl)-4-(4-fluorophenyl)-1-(1-carboxyethyl-4-piperidinyl)imidazole;
5-(2-Aminopyrimidin-4-yl)-4-(4-fluorophenyl)-1-(4-piperidinyl)imidazole;
1-Methyl-4-phenyl-5-(4-pyridyl)imidazole;
1-Methyl-4-[3-(chlorophenyl)]-5-[4-pyridinyl]imidazole;
1Methyl-4-(3-methylthiophenyl)-5-(4-pyridyl)imidazole;
(±)-1-Methyl-4-(3-methylsulfinylphenyl)-5-(4-pyridyl)imidazole;
(±)-4-(4-Fluorophenyl)-1-[3-(methylsulfinyl)propyl]-5-(4-pyridinyl)imidazole;
4-(4-Fluorophenyl)-1-[(3-methylsulfonyl)propyl]-5-(4-pyridinyl)imidazole;
1-(3-Phenoxypropyl)-4-(4-fluorophenyl)-5-(4-pyridinyl)imidazole;
1-[3-(Phenylthio)propyl]-4-(4-fluorophenyl)-5-(4-pyridinyl)imidazole;
1-[3-(4-Morpholinyl)propyl]-4-(4-fluorophenyl)-5-(4-quinolyl)imidazole;
(±)-1-(3-Phenylsulfinylpropyl) -4-(4-fluorophenyl)-5-(4-pyridinyl)imidazole;
1-(3-Ethoxypropyl)-4-(4-fluorophenyl)-5-(4-pyridinyl)imidazole;
1-(3-phenylsulfonylpropyl-4-(4-fluorophenyl)-5-(4-pyridinyl)imidazole;
1-[3-(4-Morpholinyl) propyl]-4-(3-chlorophenyl)-5-(4-pyridyl)imidazole;
1-[3-(4-Morpholinyl)propyl]-4-(3,4-dichlorophenyl)-5-(4-pyridyl)imidazole;
4-[4-(4-Fluorophenyl)-1-[3-(4-morpholinyl)propyl]-5-(pyrimid-2-one-4-yl)imidazole;
4-(4-Fluorophenyl)-5-[2-(methylthio)-4-pyrimidinyl]-1-[3-(4-morpholinyl)propyl]imidazole;
(±)-4-(4-Fluorophenyl)-5-[2-(methylsulfinyl)-4-pyrimidinyl]-1-[3-(4-morpholinyl)propyl]imidazole;
(E)-1-(1-Propenyl)-4-(4-fluorophenyl)-5-(4-pyridinyl)imidazole;
1-(2-Propenyl)-4-(4-fluorophenyl)-5-(4-pyridinyl)imidazole;
5-[(2-N,N-Dimethylamino)pyrimidin-4-yl]-4-(4-fluorophenyl)-1-[3-(4-morpholinyl)propyl]imidazole;
1-[3-(4-Morpholinyl)propyl]-5-(4-pyridinyl)-4-[4-(trifluoromethyl)phenyl]imidazole;
1-[3-(4-Morpholinyl)propyl]-5-(4-pyridinyl)-4-[3-(trifluoromethyl)phenyl]imidazole;
1-(Cyclopropylmethyl)-4-(3,4-dichlorophenyl)-5-(4-pyridinyl)imidazole;
1-(Cyclopropylmethyl)-4-(3-trifluoromethylphenyl)-5-(4-pyridinyl)imidazole;
1-(Cyclopropylmethyl)-4-(4-fluorophenyl)-5-(2-methylpyrid-4-yl)imidazole;
1-[3-(4-Morpholinyl)propyl]-5-(4-pyridinyl)-4-(3,5-bistrifluoromethylphenyl)imidazole;
5-[4-(2-Aminopyrimidinyl)]-4-(4-fluorophenyl)-1-(2-carboxy-2,2-dimethylethyl)imidazole;
1-(1-Formyl-4-piperidinyl)-4-(4-fluorophenyl)-5-(4-pyridinyl)imidazole;
5-(2-Amino-4-pyrimidinyl)-4-(4-fluorophenyl)-1-(1-methyl-4-piperidinyl)imidazole;
1-(2,2-Dimethyl-3-morpholin-4-yl)propyl-4-(4-fluorophenyl)-5-(2-Amino-4-pyrimidinyl)imidazole;
4-(4-Fluorophenyl)-5-(4-pyridyl)-1-(2-acetoxyethyl)imidazole;
5-(2-Aminopyrimidin-4-yl)-4-(4-fluorophenyl)-1-(1-benzylpyrrolin-3-yl)imidazole;
5-(2-Aminopyrimidin-4-yl)-4-(4-fluorophenyl)-1-(2,2,6,6-tetramethylpiperidin-4-yl)imidazole;
5-[4-(2-N-Methylamino)pyrimidinyl}-4-(4-fluorophenyl)-1-(4-N-methylpiperidine)imidazole;
5-[4-(2-N-Methylamino)pyrimidinyl]-4-(4-fluorophenyl)-1-(4-N-morpholino-1-propyl)imidazole;
5-[4-(2-N-Methylamino)pyrimidinyl}-4-(4-fluorophenyl)-1 (4-piperidine)imidazole;
5-[(2-Ethylamino)pyrimidin-4-yl]-4-(4-fluorophenyl)-1-(1-methylpiperdin-4-yl)imidazole;
4-(4-Fluorophenyl)-5-[2-(isopropyl)aminopyrimidiny-4-yl]-1-(1-methylpiperdin-4-yl)imidazole;
5-(2-Acetamido-4-pyrimidinyl)-4-(4-fluorophenyl)-1-(4-N-morpholino-1-propyl)imidazole;
5-(2-Acetamido-4-pyrimidinyl)-4-(4-fluorophenyl)-1-(1-methyl-4-piperidinyl)imidazole;
5-[4-(2-N-Methylthio)pyrimidinyl}-4-(4-fluorophenyl)-1-(4-piperidine)imidazole 4-(Fluorophenyl)-1-(methyl-4-piperidinyl)-5-(2-methylthio-4-pyrimidinyl)imidazole
4-(Fluorophenyl)-1-(methyl-4-piperidinyl)-5-(2-methysulfinyl-4-pyrimidinyl)imidazole
1-tert-Butyl-4-(4-fluorophenyl)-5-(2-methysulfinyl-4-pyrimidinyl)imidazole;
5-[4-(2-Aminopyrimidinyl)]-4-(4-fluorophenyl)-1-(2,2,6,6-tetramethyl-4-piperidinyl)imidazole
5-[4-(2-N-Methylamino-4-pyrimidinyl)]-4-(4-fluorophenyl)-1-(2,2,6,6-tetramethyl-4-piperidine)imidazole
5-(2-Amino-4-pyrimidinyl)-4-(4-fluorophenyl)-1-(tetrahydro-4-thiopyranyl)imidazole
5-(2-Amino-4-pyrimidinyl)-4-(4-fluorophenyl)-1-(tetrahydro-4-pyranyl)imidazole
5-(2-Methylamino-4-pyrimidinyl)-4-(4-fluorophenyl)-1-(2-cyanoethyl)imidazole
5-(2-Amino-4-pyrimidinyl)-4-(4-fluorophenyl)-1-(tetrahydro-4-sulfinylpyranyl)imidazole
5-(2-Amino-4-pyrimidinyl)-4-(4-fluorophenyl)-1-(tetrahydro-4-sulfonylpyranyl)imidazole
5-(2-Methylamino-4-pyrimidinyl)-4-(4-fluorophenyl)-1-(2,2,2-trifluoroethyl-4-piperidinyl)imidazole
5-(2-Amino-4-pyrimidinyl)-4-(4-fluorophenyl)-1-(trifluoroacetyl-4-piperidinyl)imidazole
5-(4-Pyridyl)-4-(4-fluorophenyl)-1-(4-piperidinyl)imidazole.
5-(4-Pyridyl)-4-(4-fluorophenyl)-1-(1-t-butoxy carbonyl-4-piperidinyl)imidazole.

Preferred compounds of Formula (I) include:
5-[4-(2-Amino)pyrimidinyl]-4-(4-fluorophenyl)-1-(4-N-morpholino-1-propyl)imidazole;
5-[4-(2-Aminopyrimidinyl)-4-(4-fluorophenyl)-1-(1-benzyl-4-piperidinyl)imidazole;
5-(2-Amino-4-pyrimidinyl)-4-(4-fluorophenyl)-1-(4-piperidinyl)imidazole;
5-(2-Amino-4-pyrimidinyl)-4-(4-fluorophenyl)-1-(4-N-methylpiperidinyl)imidazole;
5-[4-(2-N-Methylamino)pyrimidinyl}-4-(4-fluorophenyl)-1-(4-N-methylpiperidinyl)imidazole;
5-(2-Aminopyrimidin-4-yl)-4-(4-fluorophenyl)-1-(2,2,6,6-tetramethylpiperidin-4-yl)imidazole;
5-[4-(2-N-Methylamino)pyrimidinyl}-4-(4-fluorophenyl)-1-(4-piperidine)imidazole;

Another aspect of the present invention is the compound, 4-phenyl-5-[4-pyridyl)imidazole. Another aspect of the present invention is a pharmaceutical composition comprising a carrier or diluent and effective amount of 4-phenyl-5-[4-pyridyl)imidazole. Yet another aspect of the present invention is the novel method of treating a cytokine mediated disease state, in a mammal in need thereof, with an effective amount of 4-phenyl-5-[4-pyridyl)imidazole.

For purposes herein the dosage ranges, formulation details, and methods of making are analogous to the compounds of Formula (I).

In a further aspect the present invention provides for compounds of the Formula (II) having the structure:

(II)

wherein p is 0, or 2; $R_4$ is as defined for Formula (I) and Ar is an optionally substituted aryl as defined herein. Suitably, Ar is phenyl optionally substituted by $C_{1-4}$alkyl, $C_{1-4}$ alkoxy or halo. Preferably Ar is phenyl or 4-methylphenyl, i.e. a tosyl derivative. Compounds of Formula (II) are belived novel, provided than when Ar is tosyl, and p is 0 or 2, then $R_4$ is not an unsubstituted phenyl.

The compounds of Formula (I) may be obtained by applying synthetic procedures, some of which are illustrated in Schemes I to XI herein. The synthesis provided for in these Schemes is applicable for the producing compounds of Formula (I) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed. Once the imidazole nucleus has been established, further compounds of Formula (I) may be prepared by applying standard techniques for functional group interconversion, well known in the art.

For instance: $—C(O)NR_{13}R_{14}$ from $—CO_2CH_3$ by heating with or without catalytic metal cyanide, e.g. NaCN, and $HNR_{13}R_{14}$ in $CH_3OH$; $—OC(O)R_3$ from $—OH$ with e.g., $ClC(O)R_3$ in pyridine; $—NR_{10}—C(S)NR_{13}R_{14}$ from $—NHR_{10}$ with an alkylisothiocyante or thiocyanic acid; $NR_6C(O)OR_6$ from $—NHR_6$ with the alkyl chloroformate; $—NR_{10}C(O)NR_{13}R_{14}$ from $—NHR_{10}$ by treatment with an isocyanate, e.g. $HN=C=O$ or $R_{10}N=C=O$; $—NR_{10}—C(O)R_8$ from $—NHR_{10}$ by treatment with $Cl-C(O)R_3$ in pyridine; $—C(=NR_{10})NR_{13}R_{14}$ from $—C(NR_{13}R_{14})SR_3$ with $H_3NR_3+OAc$ by heating in alcohol; $—C(NR_{13}R_{14})SR_3$ from $—C(S)NR_{13}R_{14}$ with $R_6$-I in an inert solvent, e.g. acetone; $—C(S)NR_{13}R_{14}$ (where $R_{13}$ or $R_{14}$ is not hydrogen) from $—C(S)NH_2$ with $HNR_{13}R_{14}$—$C(=NCN)$—$NR_{13}R_{14}$ from $—C(=NR_{13}R_{14})$—$SR_3$ with $NH_2CN$ by heating in anhydrous alcohol, alternatively from $—C(=NH)$—$NR_{13}R_{14}$ by treatment with BrCN and NaOEt in EtOH; $—NR_{10}$—$C(=NCN)SR_8$ from $—NHR_{10}$ by treatment with $(R_8S)_2C=NCN$; $—NR_{10}SO_2R_3$ from $—NHR_{10}$ by treatment with $ClSO_2R_3$ by heating in pyridine; $—NR_{10}C(S)R_3$ from $—NR_{10}C(O)R_8$ by treatment with Lawesson's reagent [2,4-bis(4-methoxyphenyl)-1,3,2,4-dithiadiphosphetane-2,4-disulfide]; $—NR_{10}SO_2CF_3$ from $—NHR_6$ with triflic anhydride and base wherein $R_3$, $R_6$, $R_{10}$, $R_{13}$ and $R_{14}$ are as defined in Formula (I) herein.

Precursors of the groups $R_1$, $R_2$ and $R_4$ can be other $R_1$, $R_2$ and $R_4$ groups which can be interconvened by applying standard techniques for functional group interconversion. For example a compound of the formula (I) wherein $R_2$ is halo-substituted $C_{1-10}$ alkyl can be convened to the corresponding $C_{1-10}$ alkyl$N_3$ derivative by reacting with a suitable azide salt, and thereafter if desired can be reduced to the corresponding $C_{1-10}$alkyl$NH_2$ compound, which in turn can be reacted with $R_{18}S(0)_2X$ wherein X is halo (e.g., chloro) to yield the corresponding $C_{1-10}$alkylNHS$(0)_2R_{18}$ compound.

Alternatively a compound of the formula (I) where $R_2$ is halo-substituted $C_{1-10}$-alkyl can be reacted with an amine $R_{13}R_{14}NH$ to yield the corresponding $C_{1-10}$-alkyl$NR_{13}R_{14}$ compound, or can be reacted with an alkali metal salt of $R_{18}SH$ to yield the corresponding $C_{1-10}$alkyl$SR_{18}$ compound.

SCHEME I

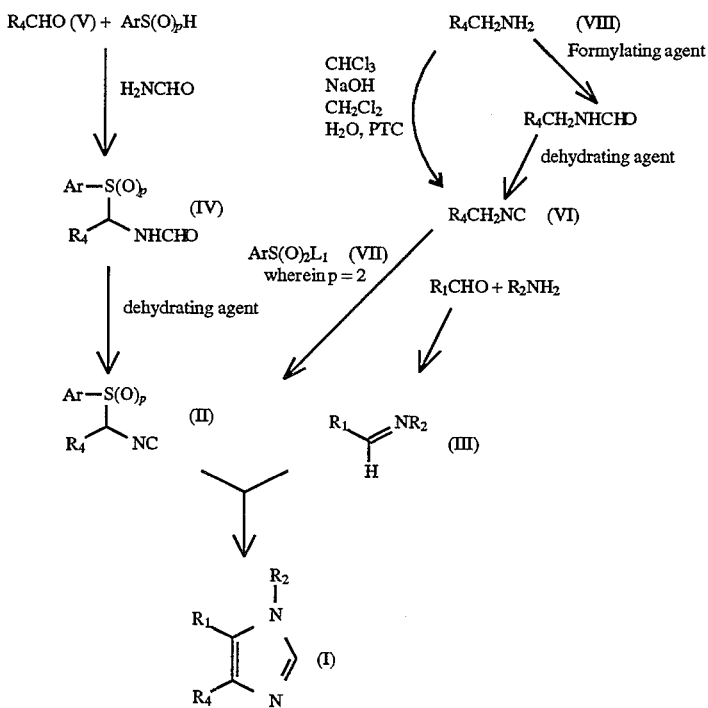

Referring to Scheme I the compounds of Formula (T) are suitably prepared by reacting a compound of the Formula (II) with a compound of the Formula (III) wherein p is 0 or 2, $R_1$, $R_2$ and $R_4$ are as deemed herein, for Formula (I), or are precursors of the groups $R_1$, $R_2$ and $R_4$, and Ar is an optionally substituted phenyl group, and thereafter if necessary converting a precursor of $R_1$, $R_2$ and $R_4$ to a group $R_1$, $R_2$ and $R_4$.

Suitably, the reaction is performed at ambient temperature or with cooling (e.g. −50° to 10°) or heating in an inert solvent such as methylene chloride, DMF, tetrahydrofuran, toluene, acetonitrile, or dimethoxyethane in the presence of an appropriate base such as 1,8-diazabicyclo [5.4.0.]undec-7-ene (DBU) or a guanidine. base such as 1,5,7-triazabicyclo[4.4.0]dec-5-ene (TBD). The intermediates of formula (II) have been found to be very stable and capable of storage for a long time. Preferably, p is 2.

Reaction a compound of the Formula (II) wherein p=2, with a compound of the Formula (III)-Scheme I gives consistently higher yields of compounds of Formula (I) than when p=0. In addition, the reaction of Formula (II) compounds wherein p=2 is more environmentally and economically attractive. When p=0, the preferred solvent used is methylene chloride, which is environmentally unattractive for large scale processing, and the preferred base, TBD, is also expensive, and produces some byproducts and impurities, than when using the commercially attractive synthesis (p=2) as further described herein.

As noted, Scheme I utilizes the 1,3-dipolar cycloadditions of an anion of a substituted aryl thiomethylisocyanide (when p=0) to an imine. More specifically, this reaction requires a strong base, such as an amine base, to be used for the deprotonation step. The commercially available TBD is preferred although t-butoxide, Li+ or Na+, or K+ hexamethyldisilazide may also be used. While methylene chloride is the preferred solvent, other halogenated solvents, such as chloroform or carbon tetrachloride; ethers, such as THF, DME, DMF, diethylether, t-butyl methyl ether; as well as acetonitrile, toluene or mixtures thereof can be utiltized. The reaction may take place from about −20° C. to about; 40° C., preferably from about 0° C. to about 23° C., more preferably from about 0° C. to about 10° C., and most preferably about 4° C. for reactions involving an $R_1$ group of pyrimidine. For compounds wherein $R_1$ is pyridine, it is recognized that varying the reactions conditions of both temperature and solvent may be necessary, such as decreasing temperatures to about −50° C. or changing the solvent to THF.

In a further process, compounds of Formula (I) may be prepared by coupling a suitable derivative of a compound of Formula (IX):

wherein $T_1$ is hydrogen and $T_4$ is $R_4$, or alternatively $T_1$ is $R_1$ and $T_4$ is H in which $R_1$, $R_2$ and $R_4$ are as hereinbefore defined; with: (i) when $T_1$ is hydrogen, a suitable derivative of the heteroaryl ring $R_1H$, under ring coupling conditions, to effect coupling of the heteroaryl ring $R_1$ to the imidazole nucleus at position 5; (ii) when $T_4$ is hydrogen, a suitable derivative of the aryl ring $R_4H$, under ring coupling conditions, to effect coupling of the aryl ring $R_4$ to the imidazole nucleus at position 4.

Such aryl/heteroaryl coupling reactions are well known to those skilled in the art. In general, an organometallic synthetic equivalent of an anion of one component is coupled with a reactive derivative of the second component, in the presence of a suitable catalyst. The anion equivalent may be formed from either the imidazole of Formula (IX), in which case the aryl/heteroaryl compound provides the reactive derivative, or the aryl/heteroaryl compound in which case the imidazole provides the reactive derivative. Accordingly, suitable derivatives of the compound of Formula (IX) or the aryl/heteroaryl rings include organometallic derivatives such as organomagnesium, organozinc, organostannane and boronic acid derivatives and suitable reactive derivatives include the bromo, iodo, fluorosulfonate and trifluoromethanesulphonate derivatives. Suitable procedures are described in WO 91/19497, the disclosure of which is incorporated by reference herein.

Suitable organomagnesium and organozinc derivatives of a compound of Formula (IX) may be reacted with a halogen, fluorosulfonate or triflate derivative of the heteroaryl or aryl ring, in the presence of a ring coupling catalyst, such as a palladium (O) or palladium (II) catalyst, following the procedure of Kumada et al., Tetrahedron Letters, 22, 5319 (1981 ). Suitable such catalysts include tetrakis-(triphenylphosphine)palladium and $PdCl_2$[1,4-bis-(diphenylphosphino)-butane], optionally in the presence of lithium chloride and a base, such as triethylamine. In addition, a nickel (II) catalyst, such as $Ni(II)Cl_2$(1,2-biphenylphosphino)ethane, may also be used for coupling an aryl ring, following the procedure of Pridgen et at., J. Org. Chem, 1982, 47, 4319. Suitable reaction solvents include hexamethylphosphor-amide. When the heteroaryl ring is 4-pyridyl, suitable derivatives include 4-bromo- and 4-iodopyridine and the fluorosulfonate and triflate esters of 4-hydroxy pyridine. Similarly, suitable derivatives for when the aryl ring is phenyl include the bromo, fluorosulfonate, triflate and, preferably, the iodo-derivatives. Suitable organomagnesium and organozinc derivatives may be obtained by treating a compound of Formula (IX) or the bromo derivative thereof with an alkyllithium compound to yield the corresponding lithium reagent by deprotonation or transmetallation, respectively. This lithium intermediate may then be treated with an excess of a magnesium halide or zinc halide to yield the corresponding organometallic reagent.

A trialkyltin derivative of the compound of Formula (IX) may be treated with a bromide, fluorosulfonate, triflate, or, preferably, iodide derivative of an aryl or heteroaryl ring compounds in an inert solvent such as tetrahydrofuran, preferably containing 10% hexamethylphosphoramide, in the presence of a suitable coupling catalyst, such as a palladium (0) catalyst, for instance tetrakis-(triphenylphosphine)-palladium, by the method described in by Stille, J. Amer. Chem. Soc, 1987, 109, 5478, U.S. Pat. Nos. 4,719,218 and 5,002,942, or by using a palladium (II) catalyst in the presence of lithium chloride optionally with an added base such as triethylamine, in an inert solvent such as dimethyl formamide. Trialkyltin derivatives may be conveniently obtained by metallation of the corresponding compound of Formula (IX) with a lithiating agent, such as s-butyl-lithium or n-butyllithium, in an ethereal solvent, such as tetrahydrofuran, or treatment of the bromo derivative of the corresponding compound of Formula (IX) with an alkyl lithium, followed, in each case, by treatment with a trialkyltin halide. Alternatively, the bromo-derivative of a compound of Formula (IX) may be treated with a suitable heteroaryl or aryl trialkyl tin compound in the presence of a catalyst such as tetrakis-(triphenyl-phosphine)-palladium, under conditions similar to those described above.

Boronic acid derivatives are also useful. Hence, a suitable derivative of a compound of Formula (IX), such as the bromo, iodo, triflate or fluorosulphonate derivative, may be reacted with a hetemaryl- or aryl-boronic acid, in the presence of a palladium catalyst such as tetrakis-(triphenylphosphine)-palladium or $PdCl_2$[1,4-bis-(diphenylphosphino)-butane] in the presence of a base such as sodium bicarbonate, under reflux conditions, in a solvent such as dimethoxyethane (see Fischer and Haviniga, Rec. Tray. Chim. Pays Bas, 84, 439, 1965, Snieckus, V., Tetrahedron Lett., 29, 2135, 1988 and Terashimia, M., Chem. Pharm. Bull., 11, 4755, 1985). Non-aqueous conditions, for instance, a solvent such as DMF, at a temperature of about 100° C., in the presence of a Pd(II) catalyst may also be employed (see Thompson W J et al, J Org Chem, 49, 5237, 1984). Suitable boronic acid derivatives may be prepared by treating the magnesium or lithium derivative with a trialkylborate ester, such as triethyl, tri-iso-propyl or tributylborate, according to standard procedures.

In such coupling reactions, it will be readily appreciated that due regard must be exercised with respect to functional groups present in the compounds of Formula (IX). Thus, in general, amino and sulfur substituents should be non-oxidised or protected.

Compounds of Formula (IX) are imidazoles and may be obtained by any of the procedures herein before described for preparing compounds of Formula (I). In particular, an α-halo-ketone or other suitably activated ketones $R_4COCH_2Hal$ (for compounds of Formula (IX) in which $T_1$ is hydrogen) or $R_1COCH_2Hal$ (for compounds of Formula (IX) in which $T_4$ is hydrogen) may be reacted with an amidine of the formula $R_2NH—C=NH$, wherein $R_2$ is as defined in Formula (I), or a salt thereof, in an inert solvent such as a halogenated hydrocarbon solvent, for instance chloroform, at a moderately elevated temperature, and, if necessary; in the presence of a suitable condensation agent such as a base. The preparation of suitable a-halo-ketones is described in WO 91/19497. Suitable reactive esters include esters of strong organic acids such as a lower alkane sulphonic or aryl sulphonic acid, for instance, methane or p-toluene sulphonic acid. The amidine is preferably used as the salt, suitably the hydrochloride salt, which may then be converted into the free amidine in situ, by employing a two phase system in which the reactive ester is in an inert organic solvent such as chloroform, and the salt is in an aqueous phase to which a solution of an aqueous base is slowly added, in dimolar amount, with vigorous stirring. Suitable amidines may be obtained by standard methods, see for instance, Garigipati R, Tetrahedron Letters, 190, 31, 1989.

Compounds of Formula (I) may also be prepared by a process which comprises reacting a compound of Formula (IX), wherein $T_1$ is hydrogen, with an N-acyl heteroaryl salt, according to the method disclosed in U.S. Pat. Nos. 4,803, 279, 4,719,218 and 5,002,942, to give an intermediate in which the heteroaryl ring is attached to the imidazole nucleus and is present as a 1,4-dihydro derivative thereof, which intermediate may then be subjected to oxidative-deacylation conditions (Scheme II). The heteroaryl salt, for instance a pyridinium salt, may be either preformed or, more preferably, prepared in situ by adding a substituted carbonyl halide (such as an acyl halide, an aroyl halide, an arylalkyl haloformate ester, or, preferably, an alkyl haloformate ester, such as acetyl bromide, benzoylchloride, benzyl chloroformate, or, preferably, ethyl chloroformate) to a solution of the compound of Formula (IX) in the heteroaryl compound $R_1H$ or in an inert solvent such as methylene chloride to which the heteroaryl compound has been added. Suitable deacylating and oxidising conditions are described in U.S. Pat. Nos. 4,803,279, 4,719,218 and 5,002,942, which references are hereby incorporated by reference in their entirety. Suitable oxidizing systems include sulfur in an inert solvent or solvent mixture, such as decalin, decalin and diglyme, p-cymene, xylene or mesitylene, under reflux conditions, or, preferably, potassium t-butoxide in t-butanol with dry air or oxygen.

In a further process, illustrated in Scheme III below, compounds of Formula (I) may be prepared by treating a compound of Formula (X) thermally or with the aid of a cyclising agent such as phosphorus oxychloride or phosphorus pentachloride (see Engel and Steglich, Liebigs Ann Chem, 1978, 1916 and Strzybny et al., J Org Chem, 1963, 28, 3381). Compounds of Formula (X) may be obtained, for instance, by acylating the corresponding a-keto-amine with an activated formate derivative such as the corresponding anhydride, under standard acylating conditions followed by formation of the imine with $R_2NH_2$. The aminoketone may be derived from the parent ketone by oxamination and reduction and the requisite ketone may in turn be prepared by decarboxylation of the beta-ketoester obtained from the condensation of an aryl (heteroaryl) acetic ester with the $R_1COX$ component.

SCHEME III

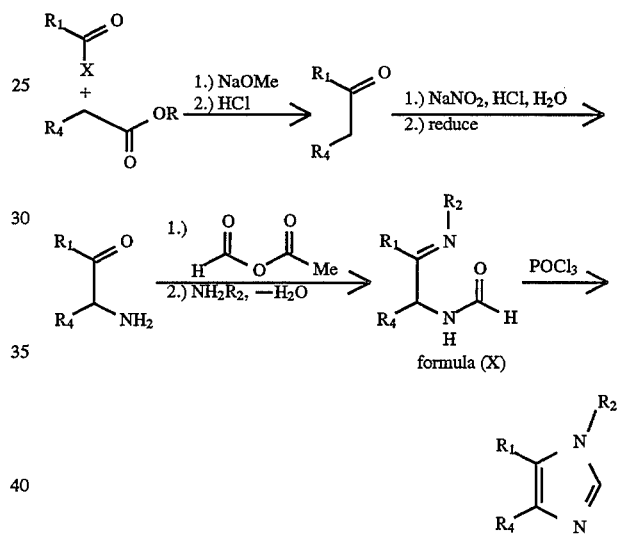

SCHEME II

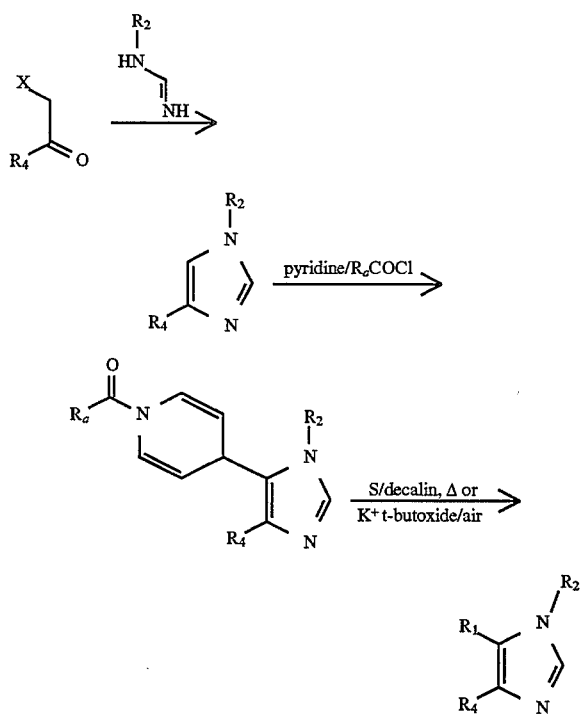

In Scheme IV illustrated below, two (2) different routes which use ketone (formula XI) for preparing a compound of Formula (I). A heterocyclic ketone (XI) is prepared by adding the anion of the alkyl heterocycle such as 4-methyl-quinoline (prepared by treatment thereof with an alkyl lithium, such as n-butyl lithium) to an N-alkyl-O-alkoxybenzamide, ester, or any other suitably activated derivative of the same oxidation state. Alternatively, the anion may be condensed with a benzaldehyde, to give an alcohol which is then oxidised to the ketone (XI).

SCHEME IV

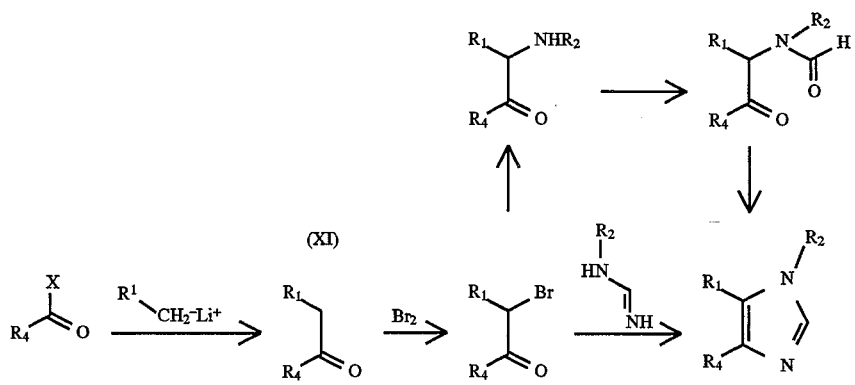

In a further process, N-substituted compounds of Formula (I) may be prepared by treating the anion of an amide of Formula (XII):

$$R_1CH_2NR_2COH \quad (XII)$$

wherein $R_1$ and $R_2$ with:
(a) a nitrile of the Formula (XIII):

$$R_4CN \quad (XIII)$$

wherein $R_4$ is as hereinbefore defined, or
(b) an excess of an acyl halide, for instance an acyl chloride, of the Formula (XIV):

$$R_4COHal \quad (XIV)$$

wherein $R_4$ is as hereinbefore defined and Hal is halogen, or a corresponding anhydride, to give a bis-acylated intermediate which is then treated with a source of ammonia, such as ammonium acetate.

SCHEME V

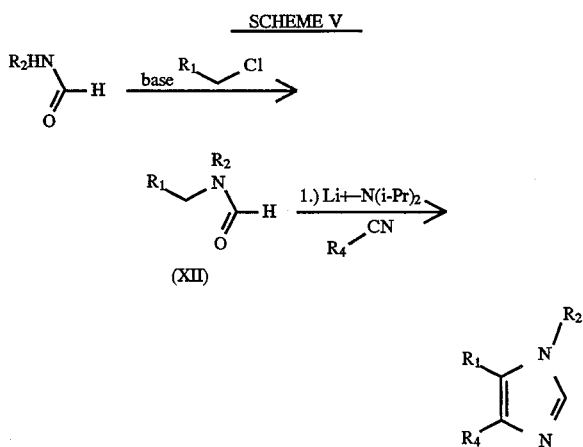

One variation of this approach is illustrated in Scheme V above. A primary amine ($R_2NH_2$) is treated with a halomethyl heterocycle of Formula $R_1CH_2X$ to give the secondary amine which is then converted to the amide by standard techniques. Alternatively the amide may be prepared as illustrated in scheme V by alkylation of the formamide with $R_1CH_2X$. Deprotonation of this amide with a strong amide base, such as lithium di-iso-propyl amide or sodium bis-(trimethylsilyl)amide, followed by addition of an excess of an aroyl chloride yields the bis-acylated compound which is then closed to an imidazole compound of Formula (I), by heating in acetic acid containing ammonium acetate. Alternatively, the anion of the amide may be reacted with a substituted aryl nitrile to produce the imidazole of Formula (I) directly.

The following description and schemes are further exemplification of the process as previously described above in Scheme I. Various pyrimidine aldehyde derivatives 6, 7 and 8 as depicted in scheme VI below, Can be prepared by modification of the procedures of Bredereck et at. (*Chem. Ber.* 1964, 97, 3407) whose disclosure is incorporated by reference herein. These pyrimidine aldehydes are then utilized as intermediates in the synthesis as further described herein. The unprotected amino aldehyde derivative, e.g. 8, can be somewhat unstable. Use of an acetolysis procedure, as described in Scheme VI, wherein the aldehyde 7 is isolated as the acetamide derivative, (compound 3 is converted to 7, via the intermediate 4) and leads to a more stable compound for use in the cycloaddition reaction to make compounds of Formula (I).

General acetolysis conditions, for such a reaction are employed and are well known to those of skill in the art. Suitable conditions are exemplified, for instance in Example 83. In greater detail, the reaction employs heating the 2-amino pyrimidine dialkoxy acetal with acetic anhydride in the presence of a catalytic mount of concentrated sulfuric acid, which simultaneously acetylates the amine and leads to the exchange of one of the alkoxy groups for an acetoxy group. The resultant compound is converted to the aldehyde by deacetylation with a catalytic amount of an alkoxide salt and the corresponding alcohol solvent, e.g. Na+ methoxide and methanol. Alternatively, higher yields can be obtained by first acetylating the amine with acetic anhydride and then affecting exchange by subsequent addition of concentrated sulfuric acid.

Scheme VI

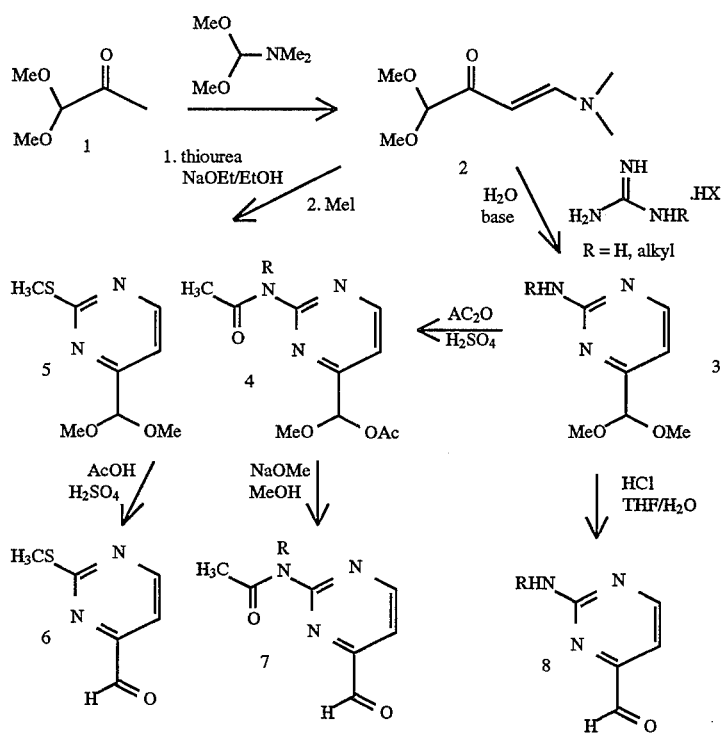

The reaction of imines with tosylmethyl isonitriles was first reported by van Leusen (van Leusen, et al., *J. Org. Chem.* 1977, 42, 1153.) Reported were the following conditions: tea butyl amine(tBuNH$_2$) in dimethoxyethane (DME), K$_2$CO$_3$ in MeOH, and NaH in DME. Upon re-examination of these conditions each was found to produce low yields. The desired product for instance, 5-[(2-(1-methylamino)-pyrimidin-4-yl]-4-(4-fluorophenyl)-1-(1-methylpiperdin-4-yl)imidazole was isolated at yields less than 50%, using t-BuNH$_2$ in DME at room temperature, but a second pathway involving amine exchange to produce the t-butyl imine followed by reaction with the isocyanide 1 to produce the tBu imidazole was also operating. This will likely occur using any primary amine as a base. The secondary amines, while not preferred may be used, but may also decompose the isonitrile slowly. Reactions will likely require about 3 equivalents of amine to go to completion, resulting in approximately 50% isolated yields. Hindered secondary amines (diisopropylamine) while usable are very slow and generally not too effective. Use of tertiary and aromatic amines, such as pyridine, and triethylamine gave no reaction under certain test conditions, but more basic types such as DBU, and 4-dimethylamino pyridine (DMAP) while slow, did produce some yields and hence may be suitable for use herein.

As depicted in Schemes VII and VIII below, the pyrimidine aldehydes of Scheme VI, can be condensed with a primary amine, to generate an imine, which may suitably be isolated or reacted in situ, with the desired isonitrile in the presence of a variety of suitable bases, and solvents as described herein to afford the 5-(4-pyrimidinyl)imidazoles, wherein R$_2$ and R$_4$ are as defined herein for Formula CI) compounds.

One preferred method for preparing compounds of Formula (I) is shown below in Scheme VII. The imines, prepared and isolated in a separate step were often tars, which were hard to handle. The black color was also often carded over into the final product. The yield for making the imines varied, and environmentally less-acceptable solvents, such as CH$_2$Cl$_2$ were often used in their preparation.

This reaction, wherein p=2, requires a suitable base for the reaction to proceed. The reaction requires a base strong enough to deprotonate the isonitrile. Suitable bases include an amine, a carbonate, a hydride, or an alkyl or aryl lithium reagent; or mixtures thereof. Bases include, but are not limited to, potassium carbonate, sodium carbonate, primary and secondary amines, such as morpholine, piperidine, pyrrolidine, and other non-nucleophilic bases.

Suitable solvents for use herein, include but are not limited to N,N-dimethylformamide (DMF), MeCN, halogenated solvents, such as methylene chloride or chloroform, tetrahydrofuran (THF), dimethylsulfoxide (DMSO), alcohols, such as methanol or ethanol, benzene, or toluene, or DME. Preferably the solvent is DMF, DME, THF, or MeCN, more preferably DMF. Product isolation may generally be accomplished by adding water and filtering the product as a clean compound.

SCHEME VII

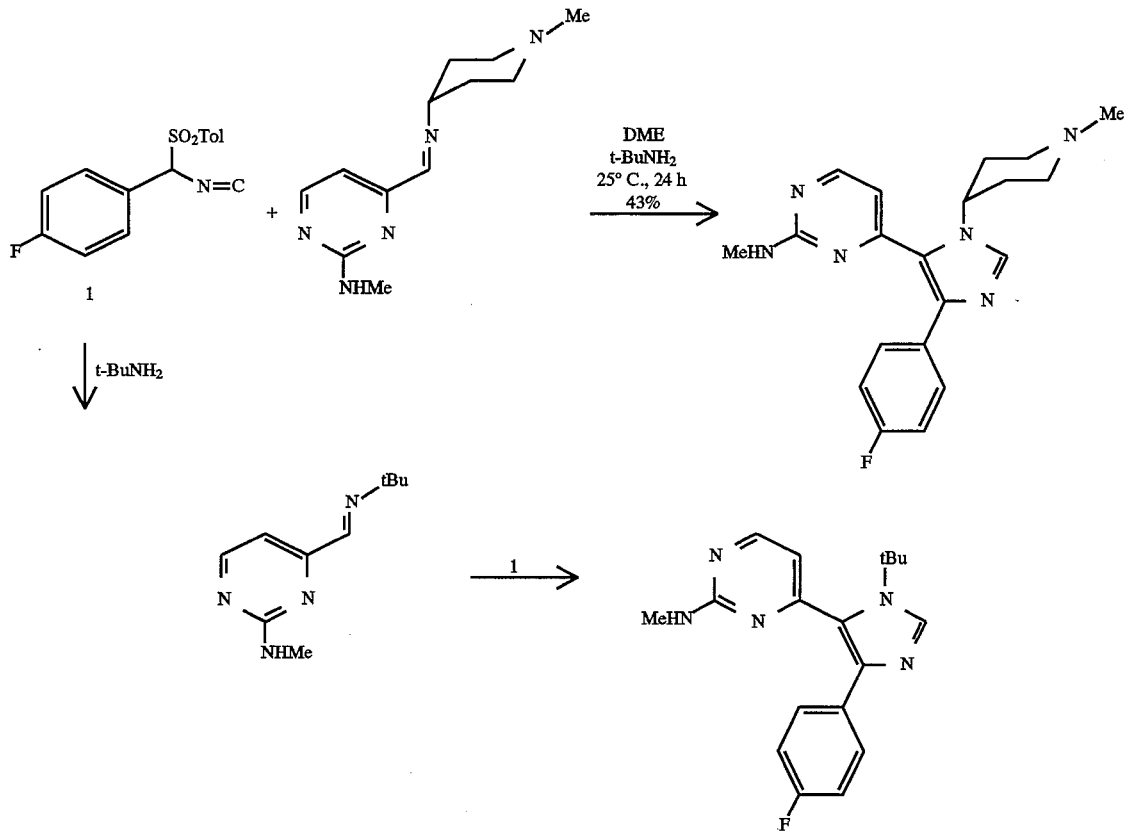

While not convenient for large scale work, addition of NaH to the isonitrile, perhaps with temperatures lower than 25° C. (in THF) are likely needed. Additionally, BuLi has also been reported to be an effective base for deprotonating tosyl. benzylisonitriles at −50° C. (DiSanto, R.; Costi, R.; Massa, S.; Artico, M. *Synth. Commun.* 1995, 25, 795).

Various temperature conditions may be utilized depending upon the preferred base. For instance, using tBuNH$_2$/DME and K2CO3/MeOH, reactions were tried at 0°, 25°, 40°, 60°, and 80° C. At temperatures above 40° C., the yields may drop to about 20%, although not much difference has been seen between 0° and 25° C. Using K$_2$CO$_3$ in DMF, reactions were tried at 0° C. and 25° C., with virtually no difference in product, quality or yield. Consequently, temperature ranges below 0° C., and above 80° C. are contemplated as also being within the scope of this invention. Preferably, the temperature ranges are from about 0° C. to about 25° C.

As shown in Scheme VIII below, the imine is preferably formed in situ in a solvent. This preferred synthesis, is a process which occurs as a one-pot synthesis. Suitably, when the primary amine is utilized as a salt, such as in the dihydrochloride salt in the Examples, the reaction may further include a base, such as potassium carbonate prior to the addition of the isonitrile. Alternatively, the piperidine nitrogen may be required to be protected as shown below. Reaction conditions, such as solvents, bases, temperatures, etc. are similar to those illustrated and discussed above for the isolated imine as shown in Scheme VIII. One skilled in the art would readily recognize that under some circumstances, the in situ formation of the imine may require dehydrating conditions, or may require acid catalysis.

SCHEME VIII

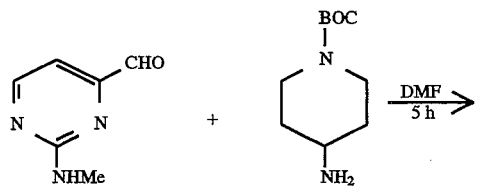

-continued
SCHEME VIII

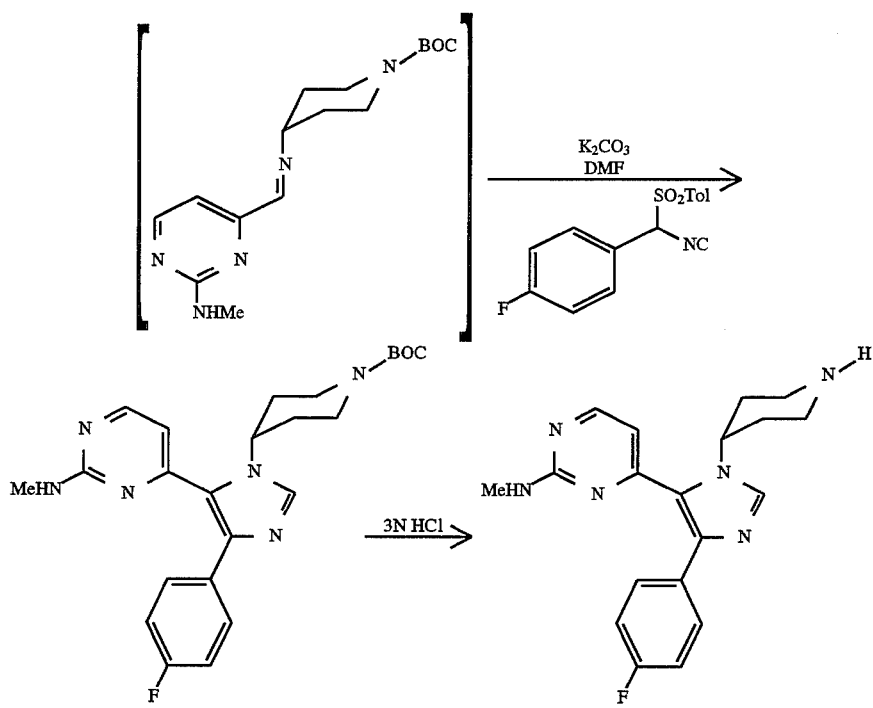

The preferred method of synthesis for compounds of Formula Cl) also provides for a suitable and reliable method for introduction of an S(O)malkyl moiety on the pyrimidine ($R_1$ group) by using, for instance, the 2-methylthio pyrimidine aldehyde derivative, as is described in the Examples section. In scheme IX below, compound 1 (X=S methyl), while a final product may also be used as a precursor, as previously noted to make further compounds of formula (I). In this particular instance the methylthio moiety is oxidized to the methyl sulfinyl moiety which may additionally be further modified to a substituted amino group.

Another embodiment of the present invention is the novel hydrolysis of 2-thiomethylpyrimidine acetal to 2-thiomethylpyrimidine aldehyde, as shown in Scheme X below. Hydrolysis of the acetal to aldehyde using various known reaction conditions, such as formic acid, did not produce a satisfactory yield of the aldehyde, <13%) was obtained. The preferred synthesis involves the use of AcOH (fresh) as solvent and concentrated $H_2SO_4$ under heating conditions, preferably a catalytic mount of sulfuric acid. Heating conditions include temperatures from about 60° to 85° C., preferably from about 70° to about 80° C. as higher

Scheme IX

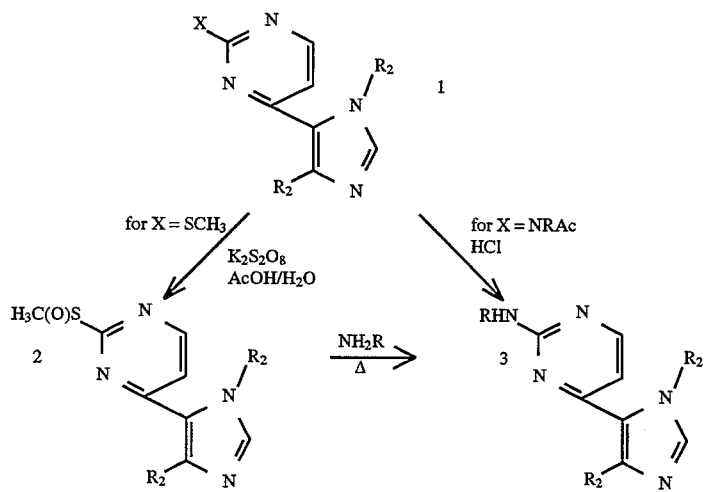

temperatures show a darkening of the reaction mixture. After the reaction is completed the mixture is cooled to about room temperature and the acetic acid is removed. An example of this procedure is described herein as Example

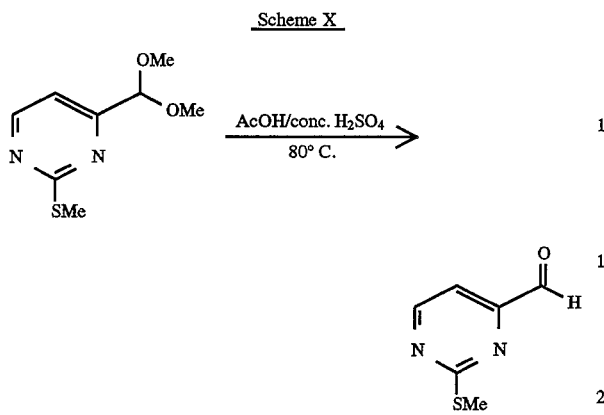

Scheme X

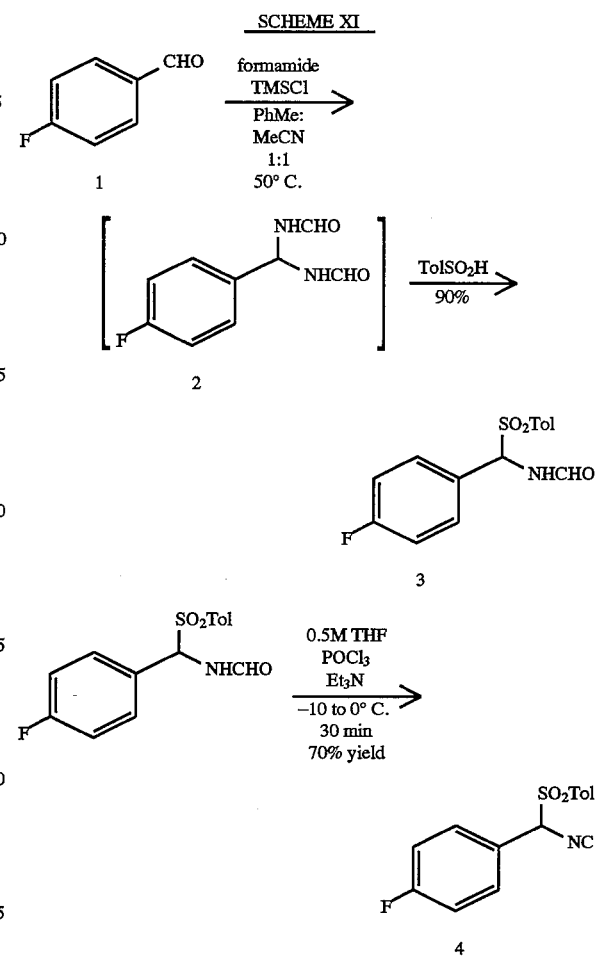

The final 2-aminopyrimidin-4-yl imidazole compounds of Formula (I), as well as similar pyridine containing compounds can be prepared by one of three methods: 1) direct reaction of the 2-aminopyrimidine imine with the isonitrile; 2) condensation of the 2-acetamidopyrimidine imine with the isonitrile followed by removal of the acetamido group and 3) oxidation of the 2-methylthiopyrimidine derivative to the corresponding sulfoxide followed by displacement with the desired amine.

While these schemes herein are presented, for instance, with an optionally substituted piperidine moiety for the resultant $R_2$ position, or a 4-fluoro phenyl for $R_4$, any suitable $R_2$ moiety or $R_4$ moiety may be added in this manner if it can be prepared on the primary amine. Similarly, any suitable $R_4$ can be added via the isonitrile mum.

The compounds of Formula (II), in Scheme I, may be prepared by the methods of van Leusen et at., supra. For example a compound of the Formula (II) may be prepared by dehydrating a compound of the Formula (IV)—Scheme I, wherein Ar, $R_4$ and p are as defined herein.

Suitable dehydrating agents include phosphorus oxychloride, oxalyl chloride, thionyl chloride, phosgene, or tosyl chloride in the presence of a suitable base such as triethylamine or diisopropylethylamine, or similar bases, etc. such as pyridine. Suitable solvents are dimethoxy ether, tetrahydrofuran, or halogenated solvents, preferably THF. The reaction is most efficent when the reaction temperatures are kept between −10° C. and 0° C. At lower temperatures incomplete reaction occurs and at higher temperatures, the solution turns dark and the product yield drops.

The compounds of formula (IV)-Scheme I may be prepared by reacting a compound of the formula (V)-Scheme I, $R_4$CHO where $R_4$ is as defined herein, with $ArS(0)_pH$ and formamide with or without water removal, preferably under dehydrating conditions, at ambient or elevated temperature e.g. 30° to 150°, conveniently at reflux, optionally in the presence of an acid catalyst. Alternatively trimethysilylchloride can be used in place of the acid catalyst. Examples of acid catalysts include camphor-10-sulphonic acid, formic acid, p-toluenesulphonic acid, hydrogen chloride or sulphuric acid.

An optimal method of making an isonitrile of Formula (II) is illustrated below, in Scheme XI, and in the Examples section, Example 85 herein.

The conversion of the substituted aldehyde to the tosylbenzyl formamide may be accomplished by heating the aldehyde, 1-Scheme XI, with an acid, such as p-toluenesulfonic acid, formic acid or camphorsulfonic acid; with formamide and p-toluene-sulfinic acid [under reaction conditions of about 60° C. for about 24 hours]. Preferably, no solvent is used. The reaction, may give poor yields (<30%) when solvents, such as DMF, DMSO, toluene, acetonitrile, or excess formamide are used. Temperatures less than 60° C. are generally poor at producing the desired product, and temperatures in excess of 60° C. may produce a product which decomposes, or obtain a benzylic bis-formamide 2-Scheme XI.

Another embodiment of the present invention is the synthesis of the tosyl benzyl formamide compound, achieved by reacting the bisformamide intermediate 2-Scheme XI with p-toluenesulfinic acid. In this preferred mute, preparation of the bis-formamide from the aldehyde is accomplished by heating the aldehyde with formamide, in a suitable solvent with acid catalysis. Suitable solvents are toluene, acetonitrile, DMF, and DMSO or mixtures thereof. Acid catalysts, are those well known in the art, and include but are not limited to hydrogen chloride, p-toluenesulfonic acid, camphorsulfonic acid, and other anhydrous acids. The reaction can be conducted at temperatures ranging from about 250° C. to 110° C., preferably about 50° C., suitably for about 4 to about 5 hours, longer reaction times are also acceptable. Product decomposition and lower yields may be observed at higher temperatures (>70° C.) at prolonged reactions times. Complete conversion of the product generally requires water removal from the reaction mixture.

Preferred conditions for converting a bis-formamide derivative to the tosyl benzyl formamide are accomplished by heating the bisformamide in a suitable solvent with an acid catalyst and p-toluenesulfinic acid. Solvents for use in this reaction include but are not limited to toluene, and acetonitrile or mixtures thereof. Additional mixtures of these solvents with DMF, or DMSO may also be used but may result in lower yields. Temperatures may range from about 30° C. to about 100° C. Temperatures lower than 40° C. and higher than 60° C. are not preferred as the yield and rate decreases. Preferably the range is from about 40° to 60° C., most preferably about 50° C. The optimal time is about 4 to 5 hours, although it may be longer. Preferably, acids used include but are not limited to, toluenesulfonic acid, camphorsulfonic acid, and hydrogen chloride and other anhydrous acids. Most preferably the bisformamide is heated in toluene:acetonitrile in a 1:1 ratio, with p-toluenesulfinic acid and hydrogen chloride.

Another embodiment of the present invention is the preferred synthetic route for synthesis of the tosylbenzyl formamide compound which is accomplished using a one-pot procedure. This process first converts the aldehyde to the bis-formamide derivative and subsequently reacts the bis-formamide derivative with toluenesulfonic acid. This procedure combines the optimized conditions into a single, efficient process. High yields, >90% of the aryl (tosyl) benzylformamide may be obtained in such a manner.

Preferred reaction conditions employ a catalyst, such as trimethylsilyl chloride (TMSCl), in a preferred solvent, toluene:acetonitrile, preferably in a 1:1 ratio. A reagent, such as TMSCl, is preferred which reacts with water produced therein and at the same time produces hydrogen chloride to catalyze the reaction. Also preferred is use of hydrogen chloride and p-toluenesulfonic acid. Therefore, three suitable reaction conditions for use herein include 1) use of a dehydrating agent which also provides hydrogen chloride, such as TMSCl or p-toluene sulfinic acid; or by 2) use of a suitable dehydrating agent and a suitable source of acid source, such as but not limited to, camphorsulfonic acid, hydrogen chloride or p-toluenesulfonic acid; and 3) alternative dehydrating conditions, such as the azeotropic removal of water, and using an acid catalyst and p-toluene sulfinic acid.

Compounds of the formula (II) where p is 2 may also be prepared by reacting in the presence of a strong base a compound of the formula (VI)-Scheme I, $R_4CH_2NC$ with a compound of the formula (VII)-Scheme I, $ArSO_2L_1$ wherein $R_4$ and Ar are as defined herein and $L_1$ is a leaving group such as halo, e.g. fluoro. Suitable strong bases include, but are not limited to, alkyl lithiums such as butyl lithium or lithium diisopropylamide (Van Leusen et al., *Tetrahedron Letters*, No. 23, 2367–68 (1972)).

The compounds of formula (VI)-Scheme I may be prepared by reacting a compound of the formula (VIII)-Scheme I, $R_4CH_2NH_2$ with an alkyl formate (e.g. ethylformate) to yield an intermediate amide which can be converted to the desired isonitrile by reacting with well known dehydrating agent, such as but not limited to oxalyl chloride, phosphorus oxychloride or tosyl chloride in the presence of a suitable base such as triethylamine.

Alternatively a compound of the formula (VIII)-Scheme I may be converted to a compound of the formula (VI)-Scheme I by reaction with chloroform and sodium hydroxide in aqueous dichloromethane under phase transfer catalysis.

The compounds of the formula (III)-Scheme I may be prepared by reacting a compound of the formula $R_1CHO$ with a primary amine $R_2NH_2$.

The amino compounds of the formula (VIII)-Scheme I are known or can be prepared from the corresponding alcohols, oximes or amides using standard functional group interconversions.

Suitable protecting groups for use with hydroxyl groups and the imidazole nitrogen are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, $(CR_{10}R_{20})_n$. Suitable examples of imidazole nitrogen protecting groups include tetrahydropyranyl.

Pharmaceutically acid addition salts of compounds of Formula (I) may be obtained in known manner, for example by treatment thereof with an appropriate amount of acid in the presence of a suitable solvent.

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

Compounds of Formula (I) are capable of inhibiting proinflammatory cytokines, such as IL-1, IL-6, IL-8 and TNF and are therefore of use in therapy. IL-1, IL-6, IL8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which Comprises administering an effective amount of a compound of Formula (I) or a pharmaceutically acceptable salt thereof. The present invention also provides for a method of prophylaxis treatment in a human, or other mammal, by inhibition of the synthesis of the. COX-2 enzyme.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency. virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory, site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not Cell bound) IL-1, IL-6, IL-8 or TNF greater than or equal to 1 picogram per ml; (ii) any cell associated IL-1, IL-6, IL-8 or TNF; or (ii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or subnormal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, interleukin-1 (IL-1), Interleukin-6 (IL-6), Interleukin-8 GL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (D which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has Close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

In order to use a compound of Formula (I) or a pharmaceutically acceptable salt thereof in therapy, it will normally be Formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carder or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carder(s) must be "acceptable" in the sense of being compatible with the other ingredients of the Formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carder is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the installation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to i % w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid Formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The Formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol Formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The cytokine-inhibiting effects of compounds of the present invention were determined by the following in vitro assays:

Interleukin-1 (IL-1)

Human peripheral blood monocytes were isolated and purified from either fresh blood preparations from volunteer donors, or from blood bank buffy coats, according to the procedure of Colotta et al, J Immunol, 132, 936 (1984). These monocytes ($1 \times 10^6$) were plated in 24-well plates at a concentration of 1–2 million/ml per well. The cells were allowed to adhere for 2 hours, after which time non-adherent cells were removed by gentle washing. Test compounds were then added to the cells for 1 h before the addition of lipopolysaccharide (50 ng/ml), and the cultures were incubated at 37° C. for an additional 24h. At the end of this period, culture supernatants were removed and clarified of cells and all debris. Culture supernatants were then immediately assayed for IL-1 biological activity, either by the method of Simon et at., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. ImmunoTherapy, 6 (1), 1–12 (1990) (ELISA assay). The compounds of Formula (I), as evidenced by Examples 1 to 24 were shown to be inhibitors of in vitro IL-1 produced by human monocytes.

Tumour Necrosis Factor (TNF)

Human peripheral blood monocytes were isolated and purified from either blood bank buffy coats or plateletpheresis residues, according to the procedure of Colotta, R. et al., J Immunol, 132(2), 936 (1984). The monocytes were plated at a density of $1 \times 10^6$ cells/ml medium/well in 24-well multi-dishes. The cells were allowed to adhere for 1 hour after which time the supernatant was aspirated and fresh medium (1 ml, RPMI-1640, Whitaker Biomedical Products, Whitaker, Calif.) containing 1% fetal calf serum plus penicillin and streptomycin (10 units/ml) added. The cells were incubated for 45 minutes in the presence or absence of a test compound at 1 nM–10 mM dose ranges (compounds were solubilized in dimethyl sulfoxide/ethanol, such that the final solvent concentration in the culture medium was 0.5% dimethyl sulfoxide/0.5% ethanol). Bacterial lipopolysaccharide (*E. coli* 055:B5 [LPS] from Sigma Chemicals Co.) was then added (100 ng/ml in 10 ml phosphate buffered saline) and cultures incubated for 16–18 hours at 37° C. in a 5% $CO_2$ incubator. At the end of the incubation period, culture supernatants were removed from the cells, centrifuged at 3000 rpm to remove cell debris. The supernatant was then assayed for TNF activity using either a radioimmuno or an ELISA assay, as described in WO 92/10190 and by Becker et al., I Immunol, 1991, 147, 4307. The compounds of Formula (I), as evidenced by Examples 1 to 24 were shown to be inhibitors of in vitro TNF produced by human monocytes.

IL-1 and TNF inhibitory activity does not seem to correlate with the property of the compounds of Formula (I) in mediating arachidonic acid metabolism inhibition. Further the ability to inhibit production of prostaglandin and/or leukotdene synthesis, by nonsteroidal anti-inflammatory drugs with potent cyclooxygenase and/or lipoxygenase inhibitory activity does not mean that the compound will necessarily also inhibit TNF or IL-1 production, at non-toxic doses.

Interleukin-8 (IL-8)

Primary human umbilical cord endothelial cells (HUVEC) (Cell Systems, Kirland, Wash.) are maintained in culture medium supplemented with 15% fetal bovine serum and 1% CS-HBGF consisting of aFGF and heparin. The cells are then diluted 20-fold before being plated (250 µl) into gelating coated 96-well plates. Prior to use, culture medium are replaced with fresh medium (200 µl). Buffer or test compound (25 µl, at concentrations between 1 and 10 µM) is then added to each well in quadruplicate wells and the plates incubated for 6h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$'s where appropriate are generated by non-linear regression analysis.

Cytokine Specific Binding Protein Assay

A radio competitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible cytokine inhibitor binding assay was developed using soluble cystosolic fraction from THP.1 cells and a radiolabeled compound. For instance, a suitable radiolabeled compound of this cytokine inhibitor class is 4-(Fluorophenyl)-2-(4-hydroxyphenyl-3,5-$t_2$)-5-(4-pyridyl) imidazole. In brief, the THP.1 cytosol was routinely prepared from cell lysate obtained by nitrogen cavitation followed by a 10K×g low speed and a 100K×g high speed centrifugation, the supernatant of which was designated as the cytosolic fraction. THP.1 cytosol was incubated with appropriately diluted radioligand at room temperature for a pre-determined time to allow the binding to achieve equilibrium. The sample was added to a G-10 column and eluted with 20 mm TRN, 50 mMb -mercaptoethanol, $NAN_3$. The fraction encompassing the void volume was collected and the radioactivity was assessed by liquid scintillation counting. This was determined to reflect bound radioligand since the radioactive signal was abrogated by the presence of excess cold ligand in the incubation mixture or when there was no cytosolic fraction present. Compounds of Formula (I) at various doses were added to the binding assay to achieve inhibition of binding of the radiolabel. $IC_{50}$s as well as Ki values were determined by regression analysis and scatchard plot analysis respectively. There is generally excellent correlation between the $IC_{50}$ of compounds tested in both the binding assay and the bioassay and can be used interchangeably in many cases.

Patent Application U.S. Ser. No. 08/123 175 Lee et at., filed September 1993 whose disclosure is incorporated by reference herein in its entirely describes the above noted method for screening drugs to identify compounds which interact with and bind to the cytokine specific binding protein (hereinafter CSBP). However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the creening protocol. Regardless of the form of the binding protein, a plurality of compounds are contacted with the binding protein under conditions sufficient to form a compound/binding protein complex and compound capable of forming, enhancing or interfering with said complexes are detected.

More specifically, the Binding Assay is performed as follows:

MATERIALS

Incubation buffer: 20 mM Tris, 1 mM $MgCl_2$, 20 mM Hepes, 0.02% $NaN_3$, store at 4° C. Elution buffer: 20 mM Tris, 50 mM 2-mercaptoethanol, $NaN_3$, store at 4° C. G-10 Sephadex: add 100 g Sephadex G-10 (Pharmacia, Uppsala, Sweden) to 400 mL dd H2O and allow to swell at room temperature for 2 hours. Decant fines and wash 3 times. Add $NaN_3$ and qs with dd $H_2O$ to 500 mLs and store at 4° C.

Assemble Columns: Straw column, filter frit and tip (Kontes, SP 420160-000, 420162-002). Lowsorb tubes (Nunc) used in binding reaction. THP. 1 cytosol spun at 15000 rpm for 5 min to clarify. THP.1 cytosol prepared by hypnotic treatment of cells and lysis by decompression in nitrogen. Nuclei and membrane fragments removed by differential centrifugation (10,000 g for 1 hour and 100,000 g for 1 hour).

Compounds: Non-radioactive Compound I with corresponding EtOH control (dilutions made in incubation buffer) and $^3$H-Compound I (dilutions in incubation buffer)

METHOD

A. Column Preparation
1. Begin 30 min before anticipated elution of reaction mixture.
2. Add 3 mL of G-10 slurry to column for bed vol of 1.5 ml.
3. Rinse with 7 mL elution buffer (fill to top of column)
4. Cut columns down to size.

B. Sample Incubation
1. 15 min incubation at 4° C.
2. Binding reaction mixture; 100 gL cytosol, 10 uL cold Compound I or EtOH control, 10 µL 3H-Compound I (molar concentration depends on nature of study).
3. "Free" control=100 µL incubation buffer in lieu of cytosol preparation.

C. Sample Elution
1. Elute at 4° C.
2. Add total reaction volume to G-10 column.
3. Add 400 µL elution buffer to column and discard eluate.
4. Add 500 µL elution buffer to column, collecting eluted volume in 20 ml scintillation vial.
5. Add 15 mL Ready Safe scintillation fluid.
6. Vortex and count in liquid scintillation counter for 5 minutes. Include a "total input counts control" (10 µL of labeled ligand).

D. Data Analysis
  1. Plot DPMS as output in graphic form and analyze by regression analysis and "Lundon ligand binding" software for the determination of IC 50 and Kd/Ki respectively.
  2. Rank order the IC50s of the tested compounds in the bioassay and compare to that generated by the binding assay and establish a correlation curve.

The binding assay was further validated by the following criteria: THP.1 cytosol demonstrated saturable and specific binding of the radiolabeled compound.

Preparation of 4-(Fluorophenyl)-2-(4-hydroxyphenyl-3,5-t2)-5-(4-pyridyl)imidazole, (Compound I).

A 2.9 mg (0.0059 mmol) portion of 2-(3,5-Dibromo-4-hydroxyphenyl)-4-(4-fluorophenyl)-5-(4-pyridyl)imidazole, Compound I(p), was dissolved in 0.95 mL of dry DMF and 0.05 mL of triethylamine in a 2.4 mL round bottom flask equipped with a small magnetic stirring bar. A 1.7 mg portion of 5% Pd/C (Engelhard lot 28845) was added, and the flask was attached to the stainless steel tritium manifold. The mixture was degassed through four freeze-pump-thaw cycles, then tritium gas (5.3 Ci, 0.091 mmol) was introduced. The reaction mixture was allowed to warm to room temperature and was stirred vigorously for 20h. The mixture was frozen in liquid nitrogen, the remaining tritium gas (2.4 Ci) was removed, and the flask was removed from the manifold. The reaction mixture was transferred, using 3×1 mL of methanol as rinsings, into a 10 mL round bottom flask, and the solvents were removed by static vacuum transfer. A 1.5 mL portion of methanol was added to the residue, then removed by static vacuum transfer. The latter process was repeated. Finally, the residue was suspended in 1.5 mL of ethanol and filtered through a syringe-tip Millipore filter (0.45 micron), along with 3×ca. 1 mL ethanol rinsings. The total filtrate volume was determined to be 3.9 mL, and the total radioactivity, 94.2 mCi. Solution was determined to be 3.9 mL, and the total radioactivity, 94.2 mCi. HPLC analysis of filtrate (Pattisit 50DS-3, 4.6 mm I.D.×25 cm, 1 mL/min of 70:30:01 water/acetonitrile/trifluoroacetic acid, Radiorustic Flo-One Beta radio detector with 3 mL/min of Ecoscint-H cocktail through a 0.75 mL cell) showed the presence of Compound I ($R_t$=60 min. ca. 37% of total radioactivity), and a discrete intermediate presumed to be the monobromo derivative Compound Ia ($R_t$=11.8 min, ca. 9%).

The filtrate solution was evaporated to near dryness with a stream of nitrogen, and the residue was dissolved in about 1.2 mL of the HPLC mobile phase. The solution was separated by HPLC as shown below, and the peaks corresponding to Compounds I and Ia and SB collected separately.

| HPLC Method | |
| --- | --- |
| Column | Altex Ultrasphere 10 mm I.D. × 25 cm |
| Mobile Phase | 70:30:0.1 water/acetonitrile/trifluoroacetic acid |
| Flow Rate | 5 mL/min |
| UV detection | 210 nm |
| Injection Volumes | 0.05–0.4 m: |
| Retention Times | 7.8 min Compound I |
| | 24 min Compound Ia |

The pooled Compound I fractions totaled 32 mL in volume and the radioactive concentration was 1.52 mCi/mL (total 48.6 m Ci). The pooled SB Compound Ia [$^3$H] fractions (totaling 10.1 mCi) were evaporated to dryness and the residue was transferred quantitatively into a glass vial using 3.8 mL of absolute ethanol for further analysis.

An 8 mL (12.2 mCi) portion of Compound I was evaporated to dryness/n vacuo at <35° C., then redissolved in 0.5 mL of mobile phase. The whole volume was injected into the HPLC system described above, and the appropriate peak was collected. Evaporation of the collected eluate/n vacuo at <35° C. and transfer of the yellow residue into a vial with absolute ethanol provided a solution (3.8 mL, 2.44 mCi/mL) of Compound I. The portion of this solution used for NMR analyses was first evaporated to dryness using stream of nitrogen then taken up in CD3OD.

Analysis of 4-(4-Fluorophenyl)-2-(4-hydroxyphenyl-3,5-t$_2$)-5-(4-pyridyl)imidazole, Compound I.

| Radiochemical Purity by HPLC | |
| --- | --- |
| Method | |
| Column | Ultrasphere Octyl, 5 mm, 4.6 mm I.D. × 25 cm, Beckman |
| Mobile Phase: | 350:150:0.5 (v/v/v) water/acetonitrile/trifluoroacetic acid |
| Flow Rate | 1.0 mL/min |
| Mass detection | UV at 210 nm |
| Radioactivity detection | Ramona-D radioactivity flow detector |
| Scintillator | Tru-Count (Tru-Lab Supply Co.) |
| Flow rate | 5.0 mL/min |
| Cell volume | 0.75 mL |
| Retention time | 7.7 min |
| Result | 98.7 |
| Radioactive Concentration by Scintillation Counting | |
| Method | |
| Scintillator | Ready Safe (Beckman Instruments, Inc.) |
| Instrument | TM Analytic model 6881 |
| Efficiency | Automated DPM calculation from quench curve |
| Result | 2.44 mCi/mL |
| Specific Activity by Mass Spectrometry | |
| Method | CI-MS, NH$_3$ reagent gas |
| Result | 20.0 Ci/mmol |
| | $^3$H Distribution: |
| | Unlabeled 44% |
| | Single Label 43% |
| | Double Label 13% |
| $^3$H NMR[9] | |
| Method | |
| Instrument | Brunker AM 400 |
| Experiment | Proton decoupled $^3$H NMR |
| | Proton non-decoupled $^3$H NMR |
| | Proton non-decoupled $^3$H NMR |
| Peak Referencing | Solvent Peak of methanol ∂ 3.3 |
| Solvent | Methanol-d$_4$ |
| Result | Tritium is incorporated exclusively on the carbon atoms ortho to aromatic hydroxyl group |

| Analytical Summary | |
| --- | --- |
| Assay | Result |
| Radiochemical purity determined by HPLC | 98.7% |
| Radioactivity concentration determined by scintillation counting | |
| Specific activity determined by mass spectrometry | 20.0 Ci/mmol |
| $^3$H NMR | agrees with the proposed structure |

Representative compounds of Formula (1D, Examples 1 to 97, but for the compound of example 2, which was not tested, and the compounds of Examples 72, 83(d), 81(d), 81(e) have all demonstrated positive inhibitory activity in this binding assay.

Prostoglandin endoperoxide synthase-2 (PGHS-2) assay

The following assay describes a method for determining the inhibitory effects of compounds of Formula (I) on human PGHS-2 protein expression in LPS stimulated human monocytes

Method

Human peripheal blood monocytes were isolated from buffy coats by centrifugation through Ficoll and Percoll gradients. Cells were seeded at 2×10⁶/well in 24 well plates and allowed to adhere for 1 hour in RPMI supplemented with 1% human AB serum, 20 mM L-glutamine, Penicillin-Streptomycin and 10 mM HEPES. Compounds were added at various concentrations and incubated at 37° C. for 10 minutes. LPS was added at 50 ng/well (to induce enzyme expression) and incubated overnight at 37° C. The supernatant was removed and cells washed once in cold PBS. The cells were lysed in 100 μl of cold lysis buffer (50 mM Tris/HCl pH 7.5, 150 mM NaCl, 1% NP40, 0.5% sodium deoxycholate, 0.1% SDS, 300 ug/ml DNAse, 0.1% TRITON X-100, 1 mM PMSF, 1 mM leupeptin, 1 mM pepstalin). The lysate was centrifuged (10,000×g for 10 min. at 4° C.) to remove debris and the soluble fraction was subjected to SDS PAGE. analysis (12% gel). Protein separated on the gel were transferred onto nitrocellulose membrane by electrophoretic means for 2 hoists at 60 volts. The membrane was protreated for one hour in PBS/0.1% Tween 20 with 5% non-fat dry milk. After washing 3 times in PBS/Tween buffer, the membrane was incubated with a 1:2000 dilution of a monospecific antiserum to PGHS-2 or a 1:1000 dilution of an antiserum to PGHs-1 in PBS/Tween with 1% BSA for one hour with continuous shaking. The membrane was washed 3× in PBS/Tween and then incubated with a 1:3000 dilution of horseradish peroxidase conjugated donkey antiserum to rabbit Ig (Amersham) in PBS/Tween with 1% BSA for one hour with continuous shaking. The membrane was then washed 3× in PBS/Tween and the ECL immunodetection system (Amersham) was used to detect the level of expression of prostaglandin endoperoxide synthases-2.

RESULTS

The following compounds were tested and found to be active (inhibited LPS induced PGHS-2 protein expression in rank order potency similar to that for inhibiting cytokine production as noted in assays indicated): 1-[3-(4-Morpholinyl)propyl]-4-(4-fluorophenyl)-5-(4-pyridyl) imidazole, a representative compound of Formula (I); 6-(4-Fluorophenyl)-2,3-dihydro-5-(4-pyridinyl)imidazo[2, 1-b] thiazole; Dexamethasone Several compounds were tested and found to be inactive (up to 10 uM): 2-(4-Methylsulfinylphenyl)-3-(4-pyridyl)-6, 7-dihydro-(5H)-pyrrolo[1,2-a]imidazole rolipram; phenidone and NDGA None of the compounds tested was found to inhibit PGHS-1 or cPLA₂ protein levels in similar experiments.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anydrous conditions in an argon atmosphere unless otherwise indicated.

In the Examples, all temperatures are in degrees Centigrade (°C.). Mass spectra were performed upon a VG Zab mass spectrometer using fast atom bombardment, unless otherwise indicated. ¹H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal, Sat. indicates a saturated solution, eq indicates the proportion of a molar equivalent of reagent relative to the principal reactant.

Flash chromatography is run over Merck Silica gel 60 (230–400 mesh).

EXAMPLE 1

1-[3-(4-Morpholinyl)propyl]-4-(4-fluorophenyl)-5-(4-pyridyl)imidazole a) 4-fluorophenyl-tolylthiomethylformamide A solution of p-fluorobenzaldehyde (13.1 milliliters (hereinafter mL), 122 millimoles (hereinafter mmol) thiocresol (16.64 grams (hereinafter g), 122 mmol), formamide (15.0 mL, 445 mmol), and toluene (300 mL) were combined and heated to toluene reflux with azeotropic removal of H₂O for 18 h. The cooled reaction was diluted with EtOAc (500 mL) and washed with said aq N₂CO₃(3×100 mL), satd aq NaCl (100 mL), dried (N₂SO₄), and concentrated. The residue was triturated with petroleum ether, filtered and dried in vacuo to afford 28.50 g of the title compound as a white solid (85%). melting point (hereinafter top)= 119°–120°.

b) 4-fluorophenyl-tolylthiomethylisocyanide

The compound of example 1(a) (25 g, 91 mmol) in CH₂Cl₂ (300 mL) was cooled to −30° and with mechanical stirring POCl₃ (11 mL, 110 mmol) was added dropwise followed by the dropwise addition of Et₃N (45 mL, 320 mmol) with the temperature maintained below −30°. Stirred at −30 min for 30 min and 5° for 2 h, diluted with CH₂Cl₂ (300 mL) and washed with 5% aq N₂CO₃ (3×100 mL), dried (N₂SO₄) and concentrated to 500 mL. This solution was filtered through a 12×16 cm cylinder of silica in a large sintered glass funnel with CH₂Cl₂ to afford 12.5 g (53%) of purified isonitrile as a light brown, waxy solid. IR (CH₂Cl₂) 2130 cm⁻¹.

c) Pyridine-4-carboxaldehyde [4-Morpholinylprop-3-yl] imine

Pyridine-4-carboxaldehyde (2.14 g, 20 mmoL), 4-(3-aminopropyl)morpholine (2.88 g, 20 mmol), toluene (50 mL) and MgSO₄ (2 g) were combined and stirred under argon for 18 h. The MgSO₄ was filtered off and the filtrate was concentrated and the residue was reconcentrated from CH₂Cl₂ to afford 4.52 g (97%) Of the title compound as a yellow oil containing less than 5% of aldehyde based on ¹H NMR. ¹H NMR (CD₃Cl : d 8.69 (d,J=4.5 Hz, 2H), 8.28 (s, 1H), 7.58 (d, J=4.5 Hz, 2H), 3.84 (m, 6H), 2.44 (m, 6H), 1.91 (m, 2H).

d) 1-[3-(4-Morpholiny)propyl]-4-(4-fluorophenyl)-5-(4-pyridyl)imidazole

The compound of example 1(b) (1.41 g, 5.5 mmol), and the compound of example 1(c) (1.17 g, 5.0 mmol) and CH₂Cl₂ (10 mL) were cooled to 5° C. 1.5.7-triazabicyclo [4.4.0]dec-5-ene, henceforth referred to as TBD, (0.71 g 5.0 mmol) was added and the reaction was kept at 5° C. for 16 h, diluted with EtOAc (80 mL) and washed with said aq N₂CO₃ (2×15 mL). The EtOAc was extracted with 1 N HCl (3 ×15 mL), and the acid phases were washed with EtOAc (2×25 mL), layered with EtOAc (25 mL) and made basic by the addition of solid $K_2CO_3$ til pH 8.0 and then 10% NaOH til pH 10. The phases were separated and the aq was extracted with additional EtOAc (3×25 mL). The extracts were dried ($K_2CO_3$) concentrated and the residue was crystalized from acetone/hexane to afford 0.94 g (51%) of the title compound. mp=149°–150°.

EXAMPLE 2

1-(3-Chloropropyl)-4-(4-fluorophenyl)-5-(4-pyridyl) imidazole a) Pyridine-4-carboxaldehyde (3-Chloropropyl)imine To 3-chloropropylamine HCl (15.1 g, 0.120 moles (hereinafter mol)) and $H_2O$ (100 mL) was added pyridine-4-carboxaldehyde (9.55 mL, 0.100 mol), then $K_2CO_3$ (8.28 g, 0.060 mol) then $CH_2CL_2$ (100 mL) and the mixture was stirred for 40 min. The phases were separated and the aq phase was extracted with additional $CH_2Cl_2$ (2×50 mL), dried ($N_2SO_4$) and concentrated to afford 17.1 g (94%) $^1H$ NMR ($CD_3Cl$): d 8.69 (d, J=4.5 Hz, 2H, 8.32 (s, 1H), 8.28 (s, 1H), 7.58 (d, J=4.5 Hz, 2H), 3.71 (m, 2H), 3.63 (t, J=6Hz, 2H), 2.24 (t, J=6Hz, 2H). The presence of 9% of the aldehyde was evident by $^1H$ NMR.

b) 1-(3-Chloropropyl)-4-(4-fluorophenyl)-5-(4-pyridyl) imidazole

The compound of example 1(*b*) (6.85 g, 26.6 mmol), the compound of example 2(*a*) (6.32 g, 34.6 mmol), $CH_2Cl_2$ (70 mL), and TBD (4.07 g, 28.4 mmol) were reacted by the procedure of example 1(*d*) to afford 3.19 g (38%). mp=139°–140°.

EXAMPLE 3

1-(3-Azidopropyl)-4-(4-fluorophenyl)-5-(4-pyridyl) imidazole

To a solution of the compound of example 2(*b*) (250 milligram (hereinafter mg), 0.79 mmol) and DMF (5 mL) was added $NaN_3$ (256 mg, 3.95 mmol) and NaI (12 mg, 0.08 mmol) and the mixture was heated to 90° till the reaction was completed based on tic analysis (19:1 $CH_2Cl_2$/MeOH). The cooled reaction was added to 5% aq $N_2CO_3$ (20 mL) and extracted with EtOAc (3×25 mL). The combined extracts were washed with $H_2O$ (3×25 mL) and flash chromatographed (2.2×10 cm column) with 0–1% MeOH in $CH_2Cl_2$ to afford 254 mg (100%) of the title compound as a white solid. mp=64°–65°.

EXAMPLE 4

1-(3-Aminopropyl)-4-(4-fluorophenyl)-5-(4-pyridyl) imidazole

The compound of example 3, described above (254 mg, 0.79 mmol), was dissolved in THF (2 mL) an added dropwise to a 0° solution of 1 N $LiAlH_4$ in THF (1.2 mL, 1.2 mmol), stirred at 0° for 15 min, EtOAc (4 mL) was carefully added and the mixture was added to ice cold 10% NaOH (15 mL) and the product was extracted with EtOAc (4×25 mL), dried ($K_2CO_3$) and concentrated to a waxy solid, (175 mg, 75%). mp=81°–82°.

EXAMPLE 5

1-(3-Methylsulfonamidopropyl)-4-(4-fluorophenyl)-5-(4-pyridyl)imidazole

To the compound of Example 4, described above (79 mg, 0.26 mmol) in $CH_2Cl_2$ (0.5 mL) was added Et3N (72 uL, 0.52 mmol), and then methanesulfonyl chloride (25 uL, 0.31 mmol). The reaction exothermed to $CH_2Cl_2$ reflux briefly. The reaction was over within 1 min based on tlc (19:1 $CH_2Cl_2$/MeOH) and was poured into 10% NaOH (5 mL) and extracted with EtOAc (3×20 mL). The extracts were washed with $H_2O$ (10 mL) and said aq Nacl (10 mL), dried ($N_2SO_4$), concentrated and flash chromatographed (1×10 cm silica) with 0–8% MeOH in $CH_2Cl_2$ to afford 63 mg (65%). mp=186°–187°.

EXAMPLE 6

1-[3-(N-Phenylmethyl)aminopropyl]-4-(4-fluorophenyl)-5-(4-pyridyl)imidazole

Following the procedure of example 3 above, except using benzylamine as the nucleophile and purification of the crude product by titration with hot hexane, the title compound was prepared as a white solid (32% yield). mp=125°–126°.

EXAMPLE 7

1-[3-(N-Phenylmethyl-N-methyl)aminopropyl]-4-(4-fluorophenyl)-5-(4-pyridyl)imidazole Following the procedure of example 3 except using N-benzylmethylamine as the nucleophile and purification of the crude product by trituration with hot hexane, the title compound was prepared as a white solid (42% yield). mp=90°–91°.

EXAMPLE 8

1-[3-(1-Pyrrolidinyl)propyl]-4-(4-fluorophenyl)-5-(4-pyridyl)imidazole

Following the procedure of example 3 except using pyrrolidine as the nucleophile and purification of the crude product by titration with hot hexane, the title compound was prepared as a white solid (35% yield). mp=105°–107°.

EXAMPLE 9

1-(3-Diethylaminopropyl)-4-(4-fluorophenyl)-5-(4-pyridyl)imidazole

Following the procedure of example 3 except using diethylamine as the nucleophile and isolation of the product by extraction with diethyl ether, the title compound was prepared as a white solid (21% yield). mp=94°–95°.

EXAMPLE 10

1-[3-(1-Piperidinyl)propyl]-4-(4-fluorophenyl)-5-(4-pyridyl)imidazole

Following the procedure of example 3 except using piperidine as the nucleophile and purification of the crude product by trituration with hot hexane, the title compound was prepared as a white solid (63% yield). mp=105°–108°.

EXAMPLE 11

1-[3-(Methylthio)propyl]-4-(4-fluorophenyl)-5-(4-pyridyl)imidazole

Following the procedure of example 3 except using sodium thiomethane as the nucleophile and omitting the sodium iodide followed by purification of the crude product by trituration with hot hexane, the title compound was prepared as a white solid (50% yield). mp=85°–86°.

EXAMPLE 12

1-[2-(4-Morpholinyl)ethyl]-4-(4-fluorophenyl)-5-(4-pyridyl)imidazole a) Pyridine-4-carboxaldehyde-[2-(4-Morpholinyl)ethyl] imine Following the procedure of example 1(c) except using 4-(2-aminoethyl)morpholine as the amine, the title compound was prepared as a light yellow oil (100%) containing less than 10% of aldehyde based on $^1$H NMR. $^1$H NMR (CD$_3$Cl): d 8.68 (d, J=6 Hz, 2H), 8.28 (s, 1H), 7.58 (d, J=6 Hz, 2H), 3.82 (m, 2H), 3.72 (m, 4H), 2.72 (m, 2H), 2.55 (m, 4H).

b) 1-[2-(4-Morpholinyl)ethyl]-4-(4-fluorophenyl)-5-(4-pyridyl)imidazole

Following the procedure of example 1(d) except using the compound of example 20(a) as the imine, afforded the title compound as a white solid (21%). mp=114°–115°.

EXAMPLE 13

1-[3-(4-Morpholinyl)propyl]-4-(3-methylthiophenyl)-5-(4-pyridyl)imidazole a) N-[3-methylthiophenyl-(tolylthio)methyl]formamide Following the procedure of example 1(a) except using m-methylthiobenzaldehyde as the aldehyde, the title compound was prepared as a white solid (73%). mp.=103°–104°.

b) 3-methylthiophenyl-(tolylthio)methylisocyanide

Following the procedure of example 1(b) except using the compound of the previous step as the formamide, the title compound was prepared as a light brown oil (77%): IR (CH$_2$Cl$_2$) 2120 cm$^{-1}$.

c) 1-[3-(4-Morpholinyl)propyl]-4-(3-methylthiophenyl)-5-(4-pyridyl)imidazole

Following the procedure of example 1(d) except using the compound of the previous step as the isonitrile, afforded the title compound as a white solid (31%). mp =105°–106°.

EXAMPLE 14

1-[3-(4-Morpholinyl)propyl]-4-(3-methylsulfinylphenyl)-5-(4-pyridyl)imidazole The compound of example 13(c) (200 mg, 0.49 mmol) was dissolved in HOAc (4 mL). K$_2$S$_2$O$_8$ (151 mg, 0.56 mmol) dissolved in H$_2$O was added and the solution was stirred for 16 h, poured into 10% aq NaOH (50 mL) (the resulting solution was >pH 10) and extracted with EtOAc (3×25 mL). The extracts were dried (K$_2$CO$_3$), concentrated and the residual oil crystalized from acetone/hexane to afford 87 mg (42%) of a white solid. mp=117°–118°.

EXAMPLE 15

1-[3-(N-methyl-N-benzyl)aminopropyl]-4-(3-methylthiophenyl)-5-(4-pyridyl)imidazole a) Pyridine-4-carboxaldehyde 3-(N-methyl-N-benzylaminopropyl)imine Following the procedure of example 1(c) except using 3(-N-Methyl-N-benzylamino)propylamine as the amine (Ueda, T.; Ishizaki, K.; Chem. Pharm. Bull. 1967, 15, 228–237.), the title compound was obtained as a light yellow oil (100%) containing less than 10% of aldehyde based on $^1$H NMR. $^1$H NMR (CD$_3$Cl): d 8.65 (d, J=7 Hz, 2H), 8.21 (s, 1H), 7.54 (d, J =4.5 Hz, 2H), 7.52 (m, 5H), 3.69 (t, J=11 Hz, 2H), 3.48(s, 2H), 2.44 (t, J=11 Hz, 2H), 2.18 (s, 3H), 1.91 (m, 2H).

b) 1-[3-(N-methyl-N-benzyl)aminopropyl]-4-(3-methylthiophenyl)-5-(4-pyridyl)imidazole Following the procedure of example 1(d) except using the compound of example 13(b) as the isonitrile, and the compound prepared in the previous step as the imine afforded the title compound as a white solid (36%). mp=87°–88°.

EXAMPLE 16

1-[3-(N-methyl-N-benzyl)aminopropyl]-4-(3-methylsulfinylphenyl)-5-(4-pyridyl)imidazole Following the procedure of example 14 except using the compound of example 15(b) as the sulfide afforded the title compound as a white solid (97%). mp=84°–85°.

EXAMPLE 17

1-[4-(Methylthio)phenyl]-4-(4-fluorophenyl)-5-(4-pyridyl)imidazole a) Pyridine-4-carboxaldehdye (4-methylthiophenyl)imine Following the procedure of example 1(c) except using 4-(methylthio)aniline as the amine afforded (100%) of a light yellow oil with no detectable amount of aldehyde based on $^1$H NMR. $^1$H NMR (CD$_3$Cl): d 8.75 (d, J=6 Hz, 2H), 8.47 (s, 1H), 7.74 (d, J=6 Hz, 2H), 7.30 (d, J=8 Hz, 2H), 7.22 (d, J=8 Hz, 2H), 2.52(s, 3H).

b) 1-[4-(Methylthio)phenyl]-4-(4-fluorophenyl)-5-(4-pyridyl)imidazole

Following the procedure of example 1(d) except using the compound of the previous step as the imine afforded the title compound as a white solid (27%). mp=172°–173°.

EXAMPLE 18

1-[4-(Methylsulfinyl)phenyl]-4-(4-fluorophenyl)-5-(4-pyridyl)imidazole

Following the procedure of example 14 except using the compound of example 17(b) as the sulfide afforded the title compound as a white solid (67%). mp=202°–203°.

EXAMPLE 19

1-[3-(Methylthio)phenyl]-4-(4-fluorophenyl)-5-(4-pyridyl)imidazole a) Pyridine-4-carboxaldehyde (3-methylthiophenyl)imine Following the procedure of example 1(c) except using 3-(methylthio)aniline as the amine afforded (98%) of a light yellow oil with ca 2.5% of aldehyde based on $^1$H NMR. $^1$H NMR (CD$_3$Cl): d 8.76 (d, J=6 Hz, 2H), 8.44 (s, 1H), 7.74 (d, J=6 Hz, 2H), 7.30 (d, J=8 Hz, 2H), 7.34–6.98 (m, 4H), 2.52(s, 3H).

b) 1-[3-(methylthio)phenyl]-4-(4-fluorophenyl)-5-(4-pyridyl)imidazole

Following the procedure of example 1(d) except using the compound of the previous step as the amine afforded the title compound as a white solid (42%). mp=155°–156°.

EXAMPLE 20

1-[3-(Methylsulfinyl)phenyl]-4-(4-fluorophenyl)-5-(4-pyridyl)imidazole

Following the procedure of example 14 except using the compound of example 19(b) as the sulfide afforded the title compound as a white solid (67%). mp=233°–234°.

EXAMPLE 21

1-[2-(Methylthio)phenyl]-4-(4-fluorophenyl)-5-(4-pyridyl)imidazole a) Pyridine-4-carboxaldehdye (2-methylthiophenyl)imine Following the procedure of example 1(c) except using 2-(methylthio)aniline as the amine afforded (98%) of a light yellow oil with ca 8% of aldehyde based on $^1$H NMR. $^1$H NMR (CD$_3$Cl): d 8.75 (d, J=6 Hz, 2H), 8.41 (s, 1H), 7.79 (d, J=6 Hz, 2H), 7.36–7.00 (m, 4H), 2.47(s, 3H).

b) 1-12-(methylthio)phenyl]-4-(4-fluorophenyl)-5-(4-pyridyl)imidazole

Following the procedure of example 1(d) except using the compound of the previous step as the imine and purification by flash chromatography with 0–1% MeOH in CH$_2$Cl$_2$ afforded the title compound as a non-crystalline white foam (53%). mp=59°–60°.

EXAMPLE 22

1-[2-(Methylsulfinyl)phenyl]-4-(4-fluorophenyl)-5-(4-pyridyl)imidazole

Following the procedure of example 14 except using the compound of example 21(b) as the sulfide, and purification by flash chromatography with 0–4% MeOH in CH$_2$Cl$_2$ afforded the title compound as a non-crystalline white foam (52%). mp=60°–165°. (The ill defined mp is probably the result of a mixture of conformational isomers which is clearly indicated in the $^1$H and $^{13}$C NMR spectra of this compound.)

EXAMPLE 23

1-(3-Chloropropyl)-4-(4-fluorophenyl)-5-(4-pyridyl)imidazole (See also Example 2 above for alternative method of preparation)

a) 4-Fluorophenyl-tosylmethylformamide

To a solution of toluene sulphinic acid sodium salt hydrate (120 g) in water (750 ml) was added concentrated sulphuric acid (16 ml). Dichloromethane (500 ml) was added and the organic and aqueous layers were separated; the aqueous layers being extracted with dichloromethane (2×200 ml). The combined organic extracts were dried (N$_2$SO$_4$) and evaporated to dryness to yield the solid sulphinic acid (71.79 g, 0.46 mole). This was added to p-fluorobenzaldehyde (57.04 g, 0.46 mole) and formamide (62.1 g, 1.38 mole) and the resulting mixture was stirred with camphor-10-sulphonic acid (21.3 g, 0.092 mole) at 60°–65°, under nitrogen for 22 hours. A solution of sodium bicarbonate (33.6 g, 0.40 mole) in water (400 ml) was added to the ice-cooled solid product which was broken up and stirred for 30 minutes. The crude product was collected and washed with acetone (220 ml) and then ether (3×220 ml) and dried to yield the desired product, 91.5 g, 64.8%.

b) 4-Fluorophenyl-tosylmethylisocyanide

To a suspension of the compound of the previous step (3.22 g, 10.5 mmole) in dimethoxyethane (21 ml) stirring at −10° was added phosphorus oxychloride (2.36 ml, 25.3 mmole) dropwise over 5 minutes. Triethylamine (7.35 ml, 52.5 mmole) was then added dropwise over 10 minutes and the reaction mixture was poured into saturated sodium bicarbonate solution (100 ml) and the oily product was extracted into dichloromethane (2×30 ml). The organic extracts were evaporated to yield a black oil (3.51 g) which was eluted from Grade III basic alumina (60 g) using dichloromethane. The combined product fractions were evaporated and ether added to crystallize the desired product, 1.735 g, 57%.

c) 1-(3-Chloropropyl)-4-(4-fluorophenyl)-5-(4-pyridyl)-imidazole

To a solution of the compound of the previous step (1.183 g, 4.09 mmol) and the compound of example 2(a) (1.122 g, 6.15 mmole) in dimethoxyethane (15 ml) at ambient temperature was added dropwise over 10 minutes a solution of DBU (0.67 ml, 4.51 mmole) in dimethoxyethane (10m I). The reaction mixture was stirred at ambient temperature for 1½ hours and then evaporated to leave an oil which was eluted from Grade III basic alumina (100 g) to yield the desired product, 1.096 g, 85%.

EXAMPLE 24

1-[4-(4-Morpholinyl)butyl]-4-(4-fluorophenyl)-5-(4-pyridyl)imidazole a) 4-(4-Morpholino)butyl-1-pthalimide 4-Bromobutyl-1-pthalimide (5.0 g, 17.7 mmol) and morpholine (20 mL) were combined and stirred for 3 h, diluted with Et$_2$O (200 mL), and filtered. The solid was washed with more Et$_2$O and the combined filtrates were extracted with 3N HCl (3×25 mL). The combined acid phases were washed with Et$_2$O (3×50 mL), layered with EtOAc and made basic by the addition of solid K$_2$CO$_3$ til the foaming stopped and then 10% aq NaOH was added til the pH was >10. Extraction with EtOAc (3×100 mL), drying, (K$_2$CO$_3$), concentration and flash filtration 1 L silica wash first with 0–4% MeOH in CH$_2$Cl$_2$ and then elute product with 4% MeOH and 1% Et$_3$N in CH$_2$Cl$_2$ to afford 5.52 g (54%) of the title compound as a white solid.

b) 4-(4-Morpholino)butylamine

The compound of example 24(a) (1.0 g, 3.47 mmol), hydrazine monohydrate (190 µl, 3.82 mmol) and CH$_3$OH (20 mL) were combined and stirred at 23° overnight. The CH$_3$OH was removed in vacuo and the residue was concentrated to dryness from EtOH. The residue was combined with 2N HCl (20 mL) and stirred for 2h, filtered and the solid was washed with H$_2$O. The combined filtrates were concentrated in vacuo and reconcentrated from EtOH twice to give a white foam which was dissolved in 3:1 CH$_2$Cl$_2$/CH$_3$OH, and stirred with solid K$_2$CO$_3$ for 5 min and filtered. The filtrate was concentrated to afford 0.535 g (80%) of a brown oil. $^1$H NMR (CD$_3$Cl): 3.7–3.2 (m, 6H), 2.7–2.2 (m, 6), 1.6–1.3 (m, 6H).

c) Pyridine-4-carboxaldehyde [4-(4-morpholinyl)butyl] imine

Following the procedure of example 1(c) except using the compound of example 24(b) as the amine the title compound was prepared as a light yellow oil (100%) containing 30% of aldehyde based on $^1$H NMR. $^1$H NMR (CD$_3$Cl): 8.60 (d, J=6 Hz, 2H), 8.19 (s, 1H), 7.51 (d, J=6 Hz, 2H), 3.7-3.2 (m, 6H), 2.5–2.2 (m, 6), 1.7–1.4 (m, 4H).

d) 1-[4-(4-Morpholinyl)butyl]-4-(4-fluorophenyl)-5-(4-pyridyl)imidazole

Following the procedure of example 1(d) except using the compound of example 24(c) as the amine afforded the title compound (38%). mp=103°–104°.

EXAMPLE 25

1-Cyclopropyl-4-(4-fluorophenyl)-5-(4-pyridyl)imidazole a) Pyridine-4-carboxaldehyde cyclopropylimine Following the procedure of example 1(c) except using a 100% excess of the volatile cyclopropylamine the title compound was prepared as a light yellow oil (100%). $^1$H NMR (CD$_3$Cl): 8.65 (d, J=6 Hz, 2H), 8.40 (s, 1H), 7.51 (d, J=6 Hz, 2H), 3.07 (m, 1H), 1.01 (m, 4H)

b) 1-Cyclopropyl-4-(4-fluorophenyl-5-(4-pyridyl)imidazole

The compound of the previous step (20 mmol), the compound of example 1(b) (5.65 g, 22 mmol), and CH$_2$Cl$_2$ (20 mL) were cooled to 0° and TBD (2.84 g, 20 mmol) was added. Stirred at 5° for 2h, 23° for 48h and refluxed for 4 h. The crude reaction was flash filtered through a sintered glass funnel filled with silica (1 L of silica) eluting with 0–4% CH$_3$OH in CH$_2$Cl$_2$. Crystals from hexane/acetone to afford 839 mg (15%) mp=129.0°–129.5°.

EXAMPLE 26

1-Isopropyl-4-(4-fluorophenyl)-5-(4-pyridyl)imidazole a) Pyridine-4-carboxaldehyde isopropylimine Following the procedure of example 1(c) except using isopropylamine as the amine the title compound was prepared as a light yellow oil (100%). $^1$H NMR (CD$_3$Cl): 8.67 (d, J=4.4 Hz, 2H), 8.27 (s, 1H), 7.59 (d, J=4.43 Hz, 2H), 3.59 (m, 1H), 1.27 (d, J=6.3 Hz, 6H).

b) 1-Isopropyl-4-(4-fluorophenyl)-5-(4-pyridyl)imidazole

Following the procedure of example 1(d) and substituting the amine of the previous step the compound was prepared using a modified work up of flash filtration of the crude reaction through silica (0–4% CH$_3$OH in CH$_2$Cl$_2$). Two crystallizations from hexane/acetone afforded the title compound as tan needles (30%). mp=179.0–179.5.

EXAMPLE 27

1-Cyclopropylmethyl:4-(4-fluorophenyl)-5-(4-pyridyl)imidazole a) Pyridine-4-carboxaldehyde Cyclopropylmethylimine Following the procedure of example 1(c) except using cyclopropylmethylamine as the amine the title compound was prepared as a light yellow oil (100%). $^1$H NMR (CD$_3$Cl): 8.69 (d, J=4.5 Hz, 2H), 8.27 (s, 1H), 7.61 (d, J=4.5 Hz, 2H), 3.55 (d, J=6.7 Hz, 2H), 1.15 (m,1H), 0.57 (m, 2H), 0.27 (m, 2H).

b) 1-Cyclopropylmethyl-4-(4-fluorophenyl)-5-(4-pyridyl)imidazole

Following the procedure of example 1(d) substituting the imine of the previous step the compound was prepared using a modified work up of flash filtration of the crude reaction through silica (0–4% CH$_3$OH in CH$_2$Cl$_2$). Crystallization from hexane/acetone afforded the title compound as white flakes (62%). mp=162.0–162.5.

EXAMPLE 28

1-tert-Butyl-4-(4-fluorophenyl)-5-(4-pyridyl)imidazole a) Pyridine-4-carboxaldehyde tert-butylimine Following the procedure of example 1(c) except using tert-butylamine as the amine the title compound was prepared as a light yellow oil (100%). $^1$H NMR (CD$_3$Cl): 8.67 (d, J=4.4 Hz, 2H), 8.22 (s, 1H), 7.61 (d, 1=4.4 Hz, 2H), 1.30 (s, 9H).

b) 1-tert-Butyl-4-(4-fluorophenyl)-5-(4-pyridyl)imidazole

Following the procedure of example 1(d) substituting the imine of the previous step the compound was prepared using a modified work up of flash filtration of the crude reaction through silica (0–4% CH$_3$OH in CH$_2$Cl$_2$) to afford the title compound as tan powder (16%). mp=199.0–200.0.

EXAMPLE 29

1-(2,2-Diethoxyethyl)-4-(4-fluorophenyl)-5-(4-pyridyl)imidazole a) Pyridine-4-carboxaldehyde 2,2-diethoxyethylimine Following the procedure of example 1(c) except using 2,2-diethoxyethylamine as the amine the title compound was prepared as a light yellow oil (100%). $^1$H NMR (CD$_3$Cl): 8.69 (d, J=4.4 Hz, 2H), 8.28 (s, 1H), 7.60 (d, J=4.4 Hz, 2H), 4.82 (t, J=5.1 Hz, 1H0, 3.82 (d, J=5.1 Hz, 1H), 3.72 (m, 2H), 3.57 (m, 2H), 1.21 (t, J=7.3 Hz, 6H).

b) 1-(2,2-Diethoxyethyl)-4-(4-fluorophenyl)-5-(4-pyridyl)imidazole

Following the procedure of example 1(d) substituting the imine of the previous step, the compound was prepared using a modified work up of flash filtration of the crude reaction through silica (0–4% CH$_3$OH in CH$_2$Cl$_2$), followed by a flash chromatography through silica with 25–100% EtOAc in hexane) and trituration of the resulting gum with hexane afforded the title compound as a white powder (47%). mp =69.5–70.0.

EXAMPLE 30

1-Formylmethyl-4-(4-fluorophenyl)-5-(4-pyridyl)imidazole

The product of example 29(b) (400 mg, 1.13 mmol), H$_2$O (10 mL), acetone (10 mL) and concd H$_2$SO$_4$ (1 mL) were combined and refluxed for 24 h. Most of the acetone was removed in vacuo and the residue was combined with 5% aq N$_2$CO$_3$ and extracted with EtOAc, dried (N$_2$SO$_4$), concentrated and crystalized from acetone to afford the title compound as a white powder (47%). mp=118.5–119.0.

EXAMPLE 31

1-Hydroxyiminylmethyl-4-(4-fluorophenyl)-5-(4-pyridyl)imidazole

The product of example 30 (317 mg, 1.13 mmol), hydroxylamine hydrochloride (317 mg), pyridine (317 μL), and EtOH (3.8 mL) were combined and refluxed for 3h, poured into 5% aq N$_2$CO$_3$, and extracted with EtOAc, dried (N$_2$SO$_4$) and flash filtered in 0–4% MeOH in CH$_2$Cl$_2$ to afford 261 mg (78%) of the title compound as a white powder. mp=184.0–185.0.

EXAMPLE 32

1-Cyanomethyl-4-(4-fluorophenyl)-5-(4-pyridyl)imidazole

The product of example 31 (250 mg, 0.84 mmol), and CuSO$_4$ were combined and refluxed for 2h. The cooled reaction was flash filtered in 0–4% MeOH in CH$_2$Cl$_2$ to afford 129 mg (55%) of the title compound as a white powder. mp=132.0–133.0.

EXAMPLE 33

1-[3-(4-Morpholinyl)propyl]-4-(4-fluorophenyl)-5-(2-methylpyrid-4-yl)imidazole a) 4-Formyl-2-methylpyridine 4-Cyano-2-methylpyridine was prepared from 2,6-lutidine asccording to the literature procedure (Yamanaka, H.; Abe,H.; Sakamoto,T.; Hidetoshi, Hiranuma,H.; Kamata, A. Chem. Pharm. Bull. 25(7), 1821–1826.). A solution of 4-Cyano-2-methylpyridine (0.367 g, 3.11 mmoL) and toluene (3.5 mL) was cooled to −78° and 1M DIBAL in hexanes (3.6 mL, 3.6 mmoL) was added dropwise via syringe pump (T<−65°). The reaction was warmed to 5° and stirred for 5 min, recooled to −78° and $CH_3OH$ (3.5 mL) was added (T<−40°), warmed to 5° and stirred for 5 min and then 25% aq Rochelle's salt was added, stirred for 3 min and then acidified to <pH 1.0 with 10% aq $H_2SO_4$. The aqueous was made basic by the addition of solid $K_2CO_3$ and extracted with EtOAc. The extracts were dried ($N_2SO_4$) concentrated and filtered through silica (2% MeOH in $CH_2Cl_2$) to afford 253 mg (84%) of aldehyde. $H^1$ NMR ($CD_3Cl$): d 10.05 (s, 1H), 8.74 (d, J=7Hz, 1 H), 7.51 (s, 1H), 7.30 (d, J=7Hz, 1H), 2.68 (s, 3H).

b) Pyridine-4-carboxaldehyde [3-(4-morpholinyl)propyl] imine

The product of the previous step and 4-(3-aminopropyl) morpholine were reacted by the procedure of example 1(c) to afford the title compound as a yellow oil containing no aldehyde based on $^1H$ NMR. $^1H$ NMR ($CD_3Cl$): d 8.57 (d, J=5.0 Hz, 1H), 8.25 (s, 1H), 7.46 (s, 1H); 7.36 (d, J=5.0 Hz, 1H), 3.71 (m, 6H), 2.60 (s, 1H); 2.35 (m, 6H), 1.90 (m, 2H).

c) 1-[3-(4-Morpholinyl)propyl]-4-(4-fluorophenyl)-5-(2-methylpyrid-4-yl)imidazole The compound of the previous step, and the compound of example 1(b) were reacted by the procedure of example 1(d) to afford the title compound as a white solid [51% from 33 (a)]. mp=116°–117°.

EXAMPLE 34

4-(4-Fluorophenyl)-1-[3-(4-morpholinyl)propyl]-5-(2-chloropyridin-4-yl) imidazole a) 2-Chloropyridine-4-carboxaldehyde [3-(4-morpholinyl)propyl]imine 2-Chloropyridine-4-carboxaldehyde was prepared as described in the patent literature (WPI Acc. No. 88-258820/37) whose disclosure is incorporated by reference in its entirety herein. This aldehyde was reacted with 4-(3-aminopropyl)morpholine by the procedure of example 1(c) to afford the title compound as a yellow oil. 1H NMR ($CD_3Cl$): δ 8.45 (d, J=5.1 Hz, 1H), 8.24 (s, 1H), 7.63 (s, 1H); 7.51 (d, J=5.1 Hz, 1H), 3.72 (m, 6H), 2.44 (m, 6H), 1.91 (m, 2H).

b) 4-(4-Fluorophenyl)-1-[3-(4-morpholinyl)propyl]-5-(2-chloro-4-pyridinyl) imidazole Following the procedure of example 1(d) except using the compound of the previous step as the imine afforded the title compound as a white solid (93%). mp=97.0°–97.5°.

EXAMPLE 35

4-(4-Fluorophenyl)-1-[3-(4-morpholinyl)propyl]-5-(2-amino-4-pyridinyl) imidazole a) 4-(4-Fluorophenyl)-1-[3-(4-morpholinyl)propyl]-5-(2-hydrazinyl-4-pyridinyl) imidazole The compound of example 34(b) (872 mg, 2.18 mmoL) and 98% hydrazine hydrate (9 mL) was heated to 115° (bath temp) for 20 h, cooled to 23° combined with $H_2O$ (20 mL) and extracted with EtOAc (3×25 mL). The combined extracts were washed with $H_2O$ (2×20 mL) and dried ($N_2SO_4$). Flash chromatography with 0–8% $CH_3OH$ in $CH_2Cl_2$ afforded 547 mg (63%) the title compound as a white solid.

b) 4-(4-Fluorophenyl)-1-[3-(4-morpholinyl)propyl]-5-(2-amino-4-pyridinyl) imidazole The compound of the previous step (100 mg, 0.25 mmoL), absolute EtOH (15 mL) and Raney Ni (0.4 mL) were shaken under $H_2$ (45 psi) for 4 h. Flash chromatography with 0–8% $CH_3OH$ in $CH_2Cl_2$ afforded 34 mg (37%) the title compound as a white solid. mp=186°–187°.

EXAMPLE 36

1-(4-Carboxymethyl)propyl-4-(4-fluorophenyl)-5-(4-pyridyl)imidazole a) Pyridine-4-carboxaldehyde (4-carboxymethylbutyl) imine Pyridine-4-carboxaldehyde was reacted with methyl-4-aminobutyrate by the procedure of example 1(c) to afford the title compound as a yellow oil. $^1H$ NMR ($CD_3Cl$): δ 8.69 (d, J=5.8 Hz, 2H), 8.27 (s, 1H); 7.56 (d, 1=5.8 Hz, 2H), 3.70 (m, 2H); 2.31 (t, J=8.0 Hz, 2H), 2.08 (m, 2H).

b) 1-(4-Carboxymethyl)propyl-4-(4-fluorophenyl)-5-(4-pyridyl)imidazole

Following the procedure of example 1(d) except using the compound of the previous step as the imine afforded the title compound as a white solid (35%). mp=69.0°–70.0°.

EXAMPLE 37

1-(4-Carboxypropyl)-4-(4-fluorophenyl)-5-(4-pyridyl)imidazole

The compound of example 36 (100 mg, 0.29 mmol), $CH_3OH$ (3 mL), and THF (1.5 mL) were combined and the resulting soln was treated with a soln of LiOH (62 mg, 1.5 mmol) in $H_2O$ (1.5 mL) and the resulting Soln was stirred for 4 h. Removal of the volatile components in vacuo, redisolving in $H_2O$ and chromatography through HP-20 with $H_2O$ til the eluates were neutral and then with 25% aq MeOH afforded the title compound as the lithium salt; 65 mg (68%). ES (+) MS m/e=326 (MH+).

EXAMPLE 38

1-(3-Carboxymethyl)ethyl-4-(4-fluorophenyl)-5-(4-pyridyl)imidazole a) Pyridine-4-carboxaldehyde (3-carboxymethyl)ethyl imine Pyridine-4-carboxaldehyde was reacted with β-alanine methyl ester by the procedure of example 1(c) to afford the title compound as a yellow oil. $^1H$ NMR ($CD_3Cl$): δ 8.68 (d, J=4.5 Hz, 2H), 8.33 (s, 1H); 7.57 (d, J=4.5 Hz, 2H), 3.93 (t, J=6.7 Hz, 2H); 3.68 (s, 3H), 2.76 (t, J=6.7 Hz, 2H), b) 1-(3-Carboxymethyl)ethyl-4-(4-fluorophenyl)-5-(4-pyridyl)imidazole SB-219302

Following the procedure of example 1(d) except using the compound of the previous step as the imine afforded the title compound as a white solid (40% from the amine). mp=119.0°–120.0°.

EXAMPLE 39

1-(3-Carboxy)ethyl-4-(4-fluorophenyl)-5-(4-pyridyl) imidazole

The compound of example 38(b) was hydrolysed by the procedure of example 37 to afford the title compound as the lithium salt; (71%). ES (+) MS m/e=312 ($MH^+$).

EXAMPLE 40

1-(1-Benzylpiperidin-4-yl)-4-(4-fluorophenyl)-5-(4-pyridyl)imidazole a) Pyridine-4-carboxaldehyde (1-benzylpiperidin-4-yl) imine Pyridine-4-carboxaldehyde was reacted with 4-amino-N-benzylpiperidine by the procedure of example 1(c) to afford the title compound as a yellow oil.

b) 1-(1-Benzylpiperidin-4-yl)-4-(4-fluorophenyl)-5-(4-pyridyl) imidazole

Following the procedure of example 1(d) except using the compound of example the previous step as the imine afforded the fffle compound as a white solid (9% from the amine). ES (+) MS m/e=413 (MH$^+$).

EXAMPLE 41

5-(2-Aminopyrimidin-4-yl)-4-(4-fluorophenyl)-1-[3-(4-Morpholinyl)propyl]imidazole a) 2-Aminopyrimidine-4-carboxaldehyde dimethyl acetal Dimethylformamide dimethyl acetal (55 mL, 0.41 mol), and pyruvic aldehyde dimethyl acetal (50 mL, 0.41 mol) were combined and heated to 100° for 18 h. Methanol was removed in vacuo to afford an oil.

A solution of NaOH (18 g, 0.45 mol) in $H_2O$ (50 mL) was added to guanidine HCl (43 g, 0.45 mol) in $H_2O$ (100 mL), and the resulting solution was added to the above described oil. The resulting mixture was stirred at 23° for 48 h. Filtration afforded 25 g (50%) of the title compound.

b) 2-Aminopyrimidine-4-carboxaldehyde

The compound of the previous step (1.69 g, 10 mmol) and 3N HCl (7.3 mL, 22 mmol) were combined and heated to 48° for 14h, cooled, layered with EtOAc (50 mL) and neutralized by the addition of $NaHCO_3$ (2.1 g, 25 mmol) in small portions. The aq phase was extracted with EtOAc (5×50 mL) and the extracts were dried ($N_2SO_4$) and concentrated to afford 0.793 g (64%) of the title compound.

c) 2-Aminopyrimidine-4-carboxaldehyde [3-(4-Morpholinyl)propyl]imine

The compound of the previous step and 4-(3-aminopropyl)morpholine were reacted by the procedure of example 1(c) to afford the title compound as a yellow oil.

d) 5-(2-Aminopyrimidin-4-yl)-4-(4-fluorophenyl)-1-[3-(4-Morpholinyl)propyl]imidazole SB 216385

Following the procedure of example 1(d) except using the compound of the previous step as the imine afforded the title compound as a white solid. 1H NMR ($CD_3Cl$) δ 8.15(d, J=5.4 Hz, 1H), 7.62(s, 1H), 7.46 (dd, 2H), 7.00(t, J=8.6Hz, 2H), 6.50(d, J=5.4 Hz, 1H), 5.09(brd.s, 2H), 4.34(t, J=7.0 Hz, 2H), 3.69(m, 4H), 2.35(brd.s,4H), 2.24(t, J=4.6 Hz, 2H), 1.84(m, 2H).

EXAMPLE 42

5-(2-Aminopyrimidin-4-yl)-4-(4-fluorophenyl)-1-(1-benzylpiperidin-4-yl)imidazole a) 2-Aminopyrimidine-4-carboxaldehyde (1-benzylpiperidin-4-yl)imine 2-Aminopyrimidine-4-carboxaldehyde and 4-aminobenzylpiperidine were reacted by the procedure of example 1(c) to afford the title compound as a yellow oil.

b) 5-(2-Aminopyrimidin-4-yl)-4-(4-fluorophenyl)-1-(1-benzylpiperidin-4-yl)imidazole Following the procedure of example 1(d) except using the compound of the previous step as the imine afforded the title compound as a white solid (31% from the amine). mp=227°–229° (dec).

EXAMPLE 43

5-(2-Aminopyrimidin-4-yl)-4-(4-fluorophenyl)-1-(2-propyl)imidazole a) 2-Aminopyrimidine-4-carboxaldehyde (2-propyl) imine 2-Aminopyrimidine-4-carboxaldehyde and 2-propyl amine were reacted by the procedure of example 1(c) to afford the title compound as a yellow oil.

b) 5-(2-Aminopyrimidin-4-yl)-4-(4-fluorophenyl)-1-(2-propyl)imidazole

Following the procedure of example 1(d) except using the compound of the previous step as the imine afforded the title compound as a white solid (32% from the 2-aminopyrimidine aldehyde). mp=201°–202°.

EXAMPLE 44

5-(2-Aminopyrimidin-4-yl)-4-(4-fluorophenyl)-1-(cyclopropylmethyl)imidazole a) 2-Aminopyrimidine-4-carboxaldehyde (cyclopropylmethyl)imine 2-Aminopyrimidine-4-carboxaldehyde and 2-cyclopropylmethyl amine were reacted by the procedure of example 1(c) to afford the title compound as a yellow oil.

b) 5-(2-Aminopyrimidin-4-yl)-4-(4-fluorophenyl)-1-(cyclopropyl-methyl)imidazole

Following the procedure of example 1(d) except using the compound of the previous step as the imine afforded the title compound as a white solid (38% from the 2-aminopyrimidine aldehyde). mp=187°–188°.

EXAMPLE 45

5-(2-Aminopyrimidin-4-yl)-4-(4-fluorophenyl)-1-(1-carboxyethyl-4-piperidinyl)imidazole a) 2-Aminopyrimidine-4-carboxaldehyde (1-carboxyethyl-4-piperidinyl)imine, 2-Aminopyrimidine-4-carboxaldehyde and 1-carboxyethyl-4-aminopiperidine were reacted by the procedure of example 1(c) to afford the title compound as a yellow oil.

b) 5-(2-Aminopyrimidin-4-yl)-4-(4-fluorophenyl)-1-(1-carboxyethyl-4-piperidinyl)imidazole Following the procedure of example 1(d) except using the compound of the previous step as the imine afforded the title compound as a white solid (26% from the 2-aminopyrimidine aldehyde). mp=216°–218° (dec).

EXAMPLE 46

5-(2-Aminopyrimidin-4-yl)-4-(4-fluorophenyl)-1-(4-piperidinyl) imidazole a) 2-Aminopyrimidine-4-carboxaldehyde (1-t-butoxycarbonyl-4-aminopiperidinyl)imine 2-Aminopyrimidine-4-carboxaldehyde prepared in Example 41 and 1-t-butoxycarbonyl-4-aminopiperidine (Mach R. H., et. al., J. Med. Chem. 36, p3707–3719, 1993) were reacted by the procedure of example 1(c) to afford the title compound as a yellow oil.

b) 5-[4-(2-Amino)pyrimidinyl]-4-(4-fluorophenyl)-1-(1-t-butoxycarbonylpiperidin-4-yl)imidazole Following the procedure of example 1(d) except using the compound of the previous step as the imine afforded the title compound as a white solid (27% from the 2-aminopyrimidine aldehyde).

c) 5-[4-(2-Amino)pyrimidinyl]-4-(4-fluorophenyl)-1-(4-piperidinyl) imidazole

The compound of the previous step was combined with 4N HCl in dioxane (5 mL), stirred 10 min, diluted with EtOAc and the liquid phase was decanted. The solid was twice washed with $Et_2O$ (25 mL) and the liquid phase was decanted. Further trituration with EtOH (abs) and then $Et_2O$ and drying in vacuo at 50° for 16 h afforded the title compound as the trihydrochloride (41%). mp=265–275 (dec)

EXAMPLE 47

1-Methyl-4-phenyl-5-(4-pyridyl)imidazole

Following the procedure of example 48(b) except using benzonitrile the title compound as a white solid. mp=161°162.

EXAMPLE 48

1-Methyl-4-[3-(chlorophenyl)1-5-[4-pyridinyl]imidazole a) N-(4-Pyridinylmethyl)-N'-methylformamide To a stirring, argon-purged solution of 4-picolyl chloride-HCl (15 g, 91.4 mmol) and N-methylformamide (53.4 ml, 9 14 mmol) in 300 ml of THF at room temperature was added portionwise over a 20 minute period a suspension of 80% NaH (5.48 g, 183 mmol). The reaction was quenched 18h later by the addition of ice, partitioned between methylene chloride and water, washed with water and brine, dried over $MgSO_4$, and evaporated to dryness to afford a dark oil. Flash chromatography on silica gel provided 10.5 g (76%) of the titled compounds a pale yellow oil. TLC; silica gel (9:1 CHCl/MeOH) Rf=0.54.

b) 1-Methyl-4-[3-(chlorophenyl)]-5-[4-pyridinyl]imidazole

To a stirred, argon-covered, −78° solution of lithium diisopropylamide (hereinafter LDA), (prepared from 11.2 ml of diisopropylamine in 150 ml of tetrahydrofuran (hereinafter THF) by the addition of 31.9 ml of 2.5M n-BuLi in hexanes) was added dropwise the product of the previous reaction (10 g, 66.5 mmol) in 100 mL of THF. Stirring of the resultant reddish-brown solution was continued at −78° for 40 min at which point 3-chlorobenzonitrile (18.3 g, 133 mmol) in 100 mL THF was added dropwise over 20 min. The reaction was allowed to warm to room temperature, stirred for 1 h and heated to reflux for 12 h. The reaction was cooled and worked up in a manner similar to the previous reaction. Flash chromatography on silica geI provided 2.15 g of an oil which was Crystallized by dissolution with heating in 10 mL of ethyl acetate. Following crystallization, the solid was collected, washed, and dried (0.4 mm Hg) to afford 1.43 g (8%) of the titled compound as a light tan solid. mp =110°–121°.

EXAMPLE 49

1-Methyl-4-(3-methylthiophenyl)-5-(4-pyridyl)imidazole

Following the procedure of example 48(b) except using the compound of example 13(b) as the aryl nitride the title compound was obtained as a white solid. ES (+) MS m/e=281 (MH+).

EXAMPLE 50

1-Methyl-4(3-methylsulfinylphenyl)-5-(4-pyridyl)imidazole

Following the procedure of example 14 except using the compound of example 49 as the sulfide the title compound was obtained as a white solid. ES (+) MS m/e=297 (MH$^+$)

EXAMPLE 51

(±)-4-(4-Fluorophenyl)-1-[3-(methylsulfinyl)propyl]-5-(4-pyridinyl)imidazole

Following the procedure of example 14 except using the compound from example 11 as the sulfide and quenching with saturated aq $NH_4OH$ afforded the title compound as a white solid (0.87 g, 80%). mp=122°–123°.

EXAMPLE 52

4-(4-Fluorophenyl)-1-[(3-methylsulfonyl)propyl]-5-(4-pyridinyl)imidazole

The compound of Example 51 (0.5087 g, 1.48 mmol) was dissolved in methanol (8 ml) and cooled to 0° C. The addition of trifluoroacetic acid (0.12 ml) was followed by the dropwise addition of meta-chloroperoxybenzoic acid (0.23 g, 2.22 mmol) dissolved in $CH_2Cl_2$ (10 ml). After stirring for 1 h the solvents were evaporated. The residue was partitioned between $H_2O$ and EtOAc and the aqueous phase was made basic by the addition of 2N NaOH. The organic phase was separated, dried ($MgSO_4$) and concentrated and the residue was purified by flash chromatography (silica gel, 5% $MeOH/CH_2Cl_2$) to afford the title compound (0.37 g, 69%). mp=146°–147°.

EXAMPLE 53

1-(3-Phenoxypropyl)-4-(4-fluorophenyl)-5-(4-pyridinyl)imidazole

To a solution of the compound from example 2(b) (0.22 g, .70 mmol) in acetonitrile (10 ml) was added $K_2CO_3$ (0.19 g, 1.40 mmol) and phenol (0.10 g, 1.05 mmol). After stirring at 70° C. for 24 h the reaction was diluted with $H_2O$. The organic phase was separated and concentrated and the residue was purified by flash chromatography (silica gel, 5% $MeOPdCH_2Cl_2$) followed by recrystalization in hexane to afford the title compound (0.02 g, 8%) as a white solid. mp=95°–96°.

EXAMPLE 54

1-8 3-(Phenylthio)propyl]-4-(4-fluorophenyl)-5-(4-pyridinyl)imidazole

Following the procedure for example 3 except using thiophenol as the nucleophile, adding 2.2 eq $K_2CO_3$ and omitting the NaI. The cooled reaction was diluted with 10% NaOH and the product was extracted with ether. Flash chromatography was followed by recrystalization from hexane to afford the title compound (0.13 g, 53%) as white needles. mp=98°–99°.

EXAMPLE 55

1-[3-(4-Morpholinyl)propyl]-4-(4-fluorophenyl)-5-(4-quinolyl)imidazole a) Quinoyl-4-carboxaldehyde [3-(4-Morpholinyl)propyl] imine Quinoyl-4-carboxaldehyde and 4-(3-aminopropyl) morpholine were reacted by the procedure of example 1(c) to afford the title compound as a yellow oil.

b) 1-[3-(4-Morpholinyl)propyl]-4-(4-fluorophenyl)-5-(4-quinolyl)imidazole

Following the procedure of example 1(d) except using the compound of the previous step as the imine afforded the title compound as a white solid (48% from the amine). mp=139.5°140.0.

EXAMPLE 56

(±)-1-(3-Phenylsulfinylpropyl)-4-(4-fluorophenyl)-5-(4-pyridinyl)imidazole

Following the procedure of example 14 except using the compound from example 54 as the sulfide and quenching with saturated aq NH$_4$OH afforded the title compound as a white solid. mp=146.5°–148°.

EXAMPLE 57

1-(3-Ethoxypropyl)-4-(4-fluorophenyl)-5-(4-pyridinyl)imidazole

To a solution of the compound of example 2(b) (0.40 g, 1.26 mmol) in ethanol 25 ml) was added sodium ethoxide (0.8 ml, 21 wt % in ethanol). After refluxing 16 h the mixture was cooled, diluted with H$_2$O and extracted with EtOAc. Concentration of the solvent and purification by flash chromatography (silica gel, 5% MeOFd CH$_2$Cl$_2$) afforded the title compound (0.05 g, 12%). mp=85°–86°.

EXAMPLE 58

1-(3-Phenylsulfonylpropyl-4-(4-fluorophenyl)-5-(4-pyridinyl)imidazole

Following the procedure for example 52 except using the compound from example 56 as the sulfoxide and recrystalizing from hexane following the chromatography afforded the title compound as white solid. mp=109°–110°.

EXAMPLE 59

1-[3-(4-Morpholinyl)propyl]-4-(3-chlorophenyl)-5-(4-pyridyl)imidazole a) 3-chlorophenyl-tolylthiomethylisocyanide Following the procedure of example 1(a,b) except using 3-chlorobenzaldehyde as the aldehyde component the title compound was prepared.

b) 1-[3-(4-Morpholinyl)propyl]-4-(3-chlorophenyl)-5-(4-pyridyl)imidazole

Following the procedure of example 1(d) substituting the isocyanide prepared in the previous step the title compound was prepared. MS-DCI NH$_3$=383 [M+H].

EXAMPLE 60

1-3-(4-Morpholinyl)propyl]-4-(3,4-dichlorophenyl)-5-(4-pyridyl)imidazole

Following the procedure of example 1(d) substituting the isocyanide prepared in Example 67(a) the title compound was prepared. mp=106°.

EXAMPLE 61

4-[4-(4-Fluorophenyl)-1-[3-(4-morpholinyl)propyl]-5-(pyrimid-2-one-4-yl)imidazole a) 2-Methylthiopyrimidine-4-carboxaldehyde [3-(4-morpholinyl)propyl]imine Following the procedure of example 1(c) except using 2-methylthiopyrimidine-4-carboxaldehyde [Bredereck H. et al. *Chem. Ber.* 1964, 3407] afforded the title compound as a yellow oil.

b) 4-(4-Fluorophenyl)-1-[3-(4-morpholinyl)propyl]-5-(pyrimid-2-one-4-yl)imidazole Concentrated aqueous ammonium hydroxide (2 mL) was added to 4-(4-fluorophenyl)-5-[2-(methylsulfinyl)-4-pyrimidinyl]-1-[3-(4-morpholinyl)propyl]imidazole (0.14 g, 0.37 mmol) [prepared in Example 63] and the reaction mixture was heated to 150° C. for 18 h. After cooling to ambient temperature, the ammonium hydroxide was decanted. The residue was purified by flash chromatography eluting successively with 4% and 10% methanol in dichloromethane followed by successive elutions with mixtures of 90/10/1 and 70/30/3 chloroform/methanol/concentrated ammonium hydroxide. Trituration with ether afforded the title compound as an off-white solid (0.035 g, 24%). ESMS (m/z): 38.4 (M$^+$+H).

EXAMPLE 62

4-(4-Fluorophenyl)-5-[2-(methylthio)-4-pyrimidinyl]-1-[3-(4-morpholinyl)propyl]imidazole Following the procedure of 1(d) except using 2-methylthiopyrimidine-4-carboxaldehyde [3-(4-morpholinyl)propyl]imine [prepared in Example 61 (a)] afforded the title compound as a yellow oil. $^1$H NMR (CDCl$_3$) δ 8.31(d, J=7 Hz, 1H), 7.64(s,1H), 7.46 (dd, 2H), 7.05(t, J=8 Hz, 2H), 6.81(d, I=5 Hz, 1H), 4.42(t, J=7.5 Hz, 2H), 3.71(t, J=5 Hz, 4H), 2.58(s, 3H), 2.37(brd. s, 4H), 2.27(t, J=6 Hz, 2H), 1.85(m, 2H).

EXAMPLE 63

4-(4-Fluorophenyl)-5-[2-(methylsulfinyl)-4-pyrimidinyl]-1-[3-(4-morpholinyl)-propyl]imidazole A solution of K$_2$S$_2$O$_8$ (0.20 g, 0.73 mmol) in water (5 mL) was added to 4-(4-fluorophenyl)-5-[2-(methylthio)-4-pyrimidinyl]-1-[3-(4-morpholinyl)propyl]imidazole (0.20 g, 0.48 mmol) in glacial acetic acid (10 mL). After stirring at ambient temperature for 72 h, the reaction mixture was poured into water, neutralized with concentrated aqueous ammonium hydroxide and extracted four times with dichloromethane. The organic phases were combined and evaporated. The residue was purified by flash chromatography eluting successively with 1%, 2%, 4% and 10% methanol in dichloromethane to afford the title compound as a clear oil (0.15 g, 73%). $^1$H NMR (CDCl$_3$) δ 8.57(d, J=7 Hz, 1H), 7.77(s, 1H), 7.47 (dd, 2H), 7.18(d, J=5 Hz, 1H)7.09(t, J=9 Hz, 2H), 4.56(m, 2H), 3.72(t, J=5Hz, 4H), 3.00(s, 3H), 2.40(brd. s, 4H), 2.33(t, J=8 Hz, 2H), 1.94(m, 2H).

EXAMPLE 64

(E)-1-(1-Propenyl)-4-(4-fluorophenyl)-5-(4-pyridinyl)imidazole a) Pyridine-4-carboxaldehyde (2-propenyl)imine Pyridine-4-carboxaldehyde and 2-propenyl amine were reacted by the procedure of example 1(c) to afford the title compound as a yellow oil.

b) (E)-1-(1-Propenyl)-4-(4-fluorophenyl)-5-(4-pyridinyl) imidazole

Following the procedure of example 1(d) except using the compound of the previous step as the imine afforded a mixture of the title compound and 1-(2-Propenyl)-4-(4-fluorophenyl)-5-(4-pyridinyl)imidazole. Chromatography of the mixture with 0–50% EtOAc in hexanes afforded the title compound (43%). mp=173.5–174.0

EXAMPLE 65

1-(2-Propenyl)-4-(4-fluorophenyl)-5-(4-pyridinyl) imidazole

Further chromatography of the mixture from example 64(b) afforded the title compound (54%). mp=116.0°–117.0

EXAMPLE 66

5-[(2-N,N-Dimethylamino)pyrimidin-4-yl]-4-(4-fluorophenyl)-1-[3-(4-morpholinyl)-propyl] imidazole Following the procedure of example 61(b) except using aqueous dimethylamine afforded the title compound as a yellow glass. ESMS (m/z): 411 ($M^+$+H).

EXAMPLE 67

1-[3-(4-Morpholinyl)propyl]-5-(4-pyridinyl)-4-[4-(trifluoromethyl)phenyl]imidazole a) 4-trifluoromethylphenyl-tolylthiomethylisocyanide Following the procedure of example 1(a,b) except using 4-trifluoromethylbenzaldehyde as the aldehyde component the title compound was prepared.

b) 1-[3-(4-Morpholinyl)propyl]-5-(4-pyridinyl)-4-[4-(trifluoromethyl)phenyl]imidazole The imine prepared in Example 1(c) was reacted with the isocyanide prepared in the previous step using the procedure of example 1(d) to prepare the title compound. mp 133°.

EXAMPLE 68

1-[3-(4-Morpholinyl)propyl]-5-(4-pyridinyl)-4-[3-(trifluoromethyl)phenyl]imidazole a) 3-trifluoromethylphenyl-tolylthiomethylisocyanide Following the procedure of example 1(a,b) except using 3-trifluoromethyl-benzaldehyde as the aldehyde component the title compound was prepared.

b) 1-[3-(4-Morpholinyl)propyl]-5-(4-pyridinyl)-4-[4-(trifluoromethyl)phenyl]imidazole The imine prepared in Example 1(c) was reacted with the isocyanide prepared in the previous step using the procedure of example 1(d) to prepare the title compound. ESMS=417 [M+H]

EXAMPLE 69

1-(Cyclopropylmethyl)-4-(3,4-dichlorophenyl)-5-(4-pyridinyl)imidazole a) 3,4-dichlorophenyl-tolylthio methylisocyanide Following the procedure of example 1(a,b) except using 3,4-dichlorobenzaldehyde as the aldehyde component the title compound was prepared.

b) 1-(Cyclopropylmethyl)-4-(3,4-dichlorophenyl)-5-(4-pyridinyl)imidazole

Following the procedure of example 1(d) substituting the imine prepared in Example 27(a) and the isocyanide prepared in the previous step the title compound was prepared. mp=145.5°.

EXAMPLE 70

1-(Cyclopropylmethyl)-4-(3-trifluoromethylphenyl]-5-(4-pyridinyl)imidazole

Following the procedure of Example 1(d) substituting the imine prepared in Example 27(a) and the isocyanide prepared Example 68(a) the title compound was prepared. mp=105.5°.

EXAMPLE 71

1-(Cyclopropylmethyl)-4-(4-fluorophenyl)-5-(2-methylpyrid-4-yl)imidazole a) 2-Methylpyridine-4-carboxaldehyde (cyclopropylmethyl)imine Reaction of 4-formyl-2-methylpyridine [prepared in Example 33(a)] and cyclopropylmethyl amine by the procedure of example 1(c) affords the title compound as a yellow oil.

b) 1-(Cyclopropylmethyl)-4-(4-fluorophenyl)-5-(2-methylpyrid-4-yl)imidazole

Following the procedure of example 1(d) except using the compound of the previous step as the imine afforded the title compound was as a white solid (62% from the 2-aminopydmidine aldehyde). mp=141.0°–141.5°.

EXAMPLE 72

1-[3-(4-Morpholinyl)propyl]-5-(4-pyridinyl)-4-(3,5-bistrifluoromethylphenyl)imidazole a) 3,5-bistrifluoromethylphenyl-tolylthiomethylisocyanide Following the procedure of example 1(a,b) except using 3,5-bistrifluoromethylbenzaldehyde as the aldehyde component the title compound was prepared.

b) 1-[3-(4-Morpholinyl)propyl]-5-(4-pyridinyl)-4-(3,5-bistrifluoromethylphenyl)imidazole Following the procedure of example 1(d) substituting the imine prepared in Example 1(c) and the isocyanide prepared in the previous step the title compound was prepared. mp=136.5°–137.5°.

EXAMPLE 73

5-[4-(2-Aminopyrimidinyl)]-4-(4-fluorophenyl)-1-(2-carboxy-2,2-dimethylethyl) imidazole a) 2-Aminopyrimidine-4-carboxaldehyde (ethyl 3-amino-2,2-dimethylpropionate)imine 2-Aminopyrimidine-4-carboxaldehyde and ethyl 3-amino-2,2-dimethylpropionate, were reacted by the procedure of example 1(c) to afford the title compound as a yellow oil.

b) 5-[4-(2-Aminopyrimidinyl)]-4-(4-fluorophenyl)-1-(2-carboxyethyl-2,2-dimethylpropyl)imidazole Following the procedure of example 1(d) except using the compound of the previous step as the imine afforded the title compound as a white solid (11% from the amine).

c) 5-[4-(2-Aminopyrimidinyl)]-4-(4-fluorophenyl)-1-(2-carboxy-2,2-dimethylethyl)imidazole lithium salt The compound of example 73(c) was hydrolysed by the procedure of example 37 to afford the title compound as the lithium salt; (67%). ES (+) MS m/e=356.

EXAMPLE 74

1-(1-Formyl-4-piperidinyl)-4-(4-fluorophenyl)-5-(4-pyridinyl)imidazole 1-(1-Benzylpiperidin-4-yl)-4-(4-fluorophenyl)-5-(4-pyridyl)imidazole (100 mg; prepared in Example 40) was dissolved in 10% formic acid/methanol under argon and palladium black (100 mg) mixed in 10% formic acid/methanol was added. The reaction was stirred under argon at room temperature for sixteen hours. The reaction mixture was evaporated and the residue mixed in H$_2$O/ethyl acetate and the pH taken to 10. The layers were separated and the aqueous phase extracted with ethyl acetate. The combined organic layers were evaporated and the residue was flash chromatographed (silica gel/methylene Chloride/methanol) to yield the title compound, an off-white solid. ES (+) MS m/e=351 (MH$^+$)

EXAMPLE 75

5-(2-Amino-4-pyrimidinyl)-4-(4-fluorophenyl)-1-(1-methyl-4-piperidinyl)imidazole a) 4-Amino-1-methylpiperidine 1-Methylpiperidin-4-one (4.22 g, 37 mmol) and an ice cold soln of 1N HCl in Et$_2$O (37 mL, 37 mmol) were combined. Titration followed by evaporation of the Et$_2$O at 23° under a stream of argon afforded the hydrochloride. MeOH (114 mL), anhydrous NH$_4$OAc (28.7, 373 mmol) and 3A molecular sieves were added. Stirred 10 min and then NaCNBH$_3$ (2.33 g, 37 mmol) was added, and the mixture was stirred for 1 h. Acidified to <pH 1 with concentrated HCl and washed with Et$_2$O. The resulting mixture was made basic with 50% aq NaOH and extracted with EtOAc, dried (K$_2$CO$_3$), and distilled (bp=55°–60°, 15 mm) to afford 3.88 g (88%) of the title compound.

b) 2-Aminopyrimidine-4-carboxaldehyde (1-methylpiperidin-4-yl)imine

2-Aminopyrimidine-4-carboxaldehyde and the compound of the previous step were reacted by the procedure of example 1(c) to afford the title compound as a yellow oil.

b) 5-(2-Aminopyrimidin-4-yl)-4-(4-fluorophenyl)-1-(1-benzylpiperidin-4-yl)imidazole Following the procedure of example 1(d) except using the compound of the previous step as the amine afforded the title compound after purification by chromatography on silica with 0–10% MeOH and 0–1% Et$_3$N in CH$_2$Cl$_2$ followed by fractional precipitation from MeOH with Et$_2$O; as a yellow solid (20% from the amine). mp=235°–237° (dec.)

EXAMPLE 76

1-(2,2-Dimethyl-3-morpholin-4-yl)propyl-4-(4-fluorophenyl)-5-(2-Amino-4-pyrimidinyl)imidazole a) N-(1-Amino-2,2-dimethylpropyl)morpholine 2,2-dimethyl-3-N-morpholinyl propionaldehyde (Cheney, L. L. J. Amer. Chem. Soc. 1951, 73, p685–686; 855 mg, 5.0 mmol) was dissolved in Et$_2$O (2 mL) and 1N HCl in Et$_2$O (5 mL, 5 mmol) was added. Stirred 5 min and the Et$_2$O was evaporated in a stream of Ar. The solid was dissolved in anhydrous MeOH (15 mL) followed by anhydrous NH$_4$OAc (3.85 g, 50 mmol), and 3A molecular sieves. Stirred 5 min and then NaCNBH$_3$ (0.314 g, 4.0 mmoL) was added. Stirred 45 min and concd HCl was added til the reaction mixture was <pH 1. The MeOH was removed in vacuo and the residual mixture was dissolved in H$_2$O (15 mL) and extracted with Et$_2$O (25 mL). The aq phase was layered with another portion of Et$_2$O and made basic by addition of 50% aq NaOH til >pH 10. Extraction with Et$_2$O (3×40 mL), drying (K$_2$CO$_3$) and concentration afforded the title compound (86%).

b) 2-Aminopyrimidine-4-carboxaldehyde [3-(4-Morpholinyl)-2,2-dimethylpropyl]imine 2-Aminopyrimidine-4-carboxaldehyde and the product of the previous step were reacted by the procedure of example 1(c) to afford the title compound as a yellow oil.

c) 1-(2,2-Dimethyl-3-morpholin-4-yl)propyl-4-(4-fluorophenyl)-5-(2-Amino-4-pyrimidinyl)imidazole Following the procedure of example 1(d) except using the compound of the previous step as the imine afforded the title compound as a white solid (16% from the amine). mp=242°–245° (dec.).

EXAMPLE 77

4-(4-Fluorophenyl)-5-(4-pyridyl)-1-(2-acetoxyethyl)imidazole 500 mg of 4-(4-Fluorophenyl)-5-(4-pyridyl)imidazole was dried at 50° C. overnight in vacuo and added to a flask containing 20 ml of dried (sieve) dimethyl formamide (hereinafter DMF) and treated with NaH (at 0° C.), then stirred at room temperature, and dropwise with 2-acetoxy ethylbromide. After three days, the mixture was poured into ice water, extracted into methylene chloride, the organic phase washed with water, dried over sodium sulfate and stripped in vacuo. Flashed the residue on silica using CH$_2$Cl$_2$-acetone (85:15) and eluting with increasing CH$_3$OH from 0 to 10%. Two major product fractions were obtained, the pure cuts combined to give a slower eluting fraction and a faster eluting isomer. These isomers were stripped and recrystallized from EtOAc-hexane to give the minor isomer (slower moving) and the fast, major isomer (the titled compound). NMR (250 mHz, CDCl$_3$) shows CH$_2$CH$_2$ as singlet at δ 4.1 ppm, very clean, H-ortho to F, triple t at 6.9 ppm. Cal'd C:66.60, H:4.86, N: 12.92; Found C:67.10, 67.03 H:5.07, 4.94 N:13.08, 13.09. IR (nujol mull) shows 1740 cm$^{-1}$ (sharp, ester).

EXAMPLE 78

5-[4-(2-N-Methylamino)pyrimidinyl]-4-(4-fluorophenyl)-1-(4-N-morpholino-1-propyl)imidazol a) 2-N-Methylaminopyrimidine-4-dimethylacetal Sodium (3.27 g, 142 mmol) was dissolved in absolute ethanol (425 mL). 1-Methylguanidine hydrochloride (15.5 g, 142 mmol) was added and the resulting slurry was stirred for about 10 min. 1,1-Dimethoxy-2-oxo-4-dimethylamino-3-butene (142 mmol) dissolved in ethanol (20 mL) was added and the mixture was stirred at reflux for about 24 hours. The mixture was cooled and filtered. Ethanol was evaporated and the resulting residue was triturated with hot EtOAc. EtOAc washings were combined and solvent was evaporated to afford the title compound (23.5 g, 91% yield) as a yellow oil. 1H NMR (CDCl$_3$): δ 8.35 (d, J=4.5 Hz, 1H), 6.74 (d, 1H),. 5.10 (s, 1H), 3.40 (s, 6H), 3.00 (d, 3H).

b) 2-N-Methylaminopyrimidine-4-carboxaldehyde

Following the procedure of Example 41(b) except using the compound of the previous step (11.75 g, 64.6 mmol) afforded the title compound as a yellow foam (7.3 g, 82.7% yield). $^1$H NMR (CDCl$_3$): δ 9.85 (s, J=4.5 Hz, 1H), 8.52 (s, 1H), 7.03 (d, 1H), 5.52 (s, 1H), 3.10 (d, 3H).

c) 5-[4-(2-N-Methylamino)pyrimidinyl]-4-(4-fluorophenyl)-1-(4-N-morpholino-1-propyl)imidazole The compound of the previous step (5.02, 36.5 mmol) and 4-(3-aminopropyl) morpholine (5.3 mL, 36.5 mmol) were stirred in CH$_2$Cl$_2$ (180 mL). After about 16 h the mixture was cooled to 0° C. Added were the compound of Example 1(b) (11.3 g, 43.8 mmol) and TBD (8.4 g, 61.32 mmol). The mixture was let stand for about 3 days at about 5° C. The product filtered and triturated with hot EtOH to afford the title compound (6.06 g, 41.9% yield) as a pale yellow solid. mp=203°–305° C. $^1$H NMR (CDCl$_3$/MeOD): δ 8.01 (d, J=4.5 Hz, 1H), 7.60 (s, 1H), 7.37 (q, 2H), 6.95 (t, 2H), 6.29 (d, 1H), 4.32 (s, iH), 3.63 (t, 4H), 3.57 (m, 2H), 2.95 (s, 3H), 2.33 (m, 4H), 2.23 (t, 2H), 1.82 (t, 2H).

EXAMPLE 79

5-[4-(2-N-Methylamino)pyrimidinyl}-4-(4-fluorophenyl)-1-(4-N-methyl-piperidine)imidazole a) 5-[4-(2-N-Methylamino)pyrimidinyl]-4-(4-fluorophenyl)-1-(4-N-methylpiperidine)imidazole The compounds of Example 75(a) (4.25 g, 37.2 mmol) and Example 78(b) as prepared above (5.1 g, 37.2 mmol) were combined in CH$_2$Cl$_2$ (150 mL). This mixture was stirred for about 16 hours at room temperature, and cooled to 0° C. The compound of Example 1(b) and TBD were added and the resulting mixture was stirred at room temperature for about 3 days. The mixture was poured directly on a silica gel column and was purified by flash chromatography eluting with 0%–5% MeOH/CH$_2$Cl$_2$. The resulting oil was washed in acetone/hexane and the precipitate was filtered, washing with acetone to afford the title compound (1.36 g, 10% yield) as a pale yellow solid. mp=209°–210° C. $^1$H NMR (CDCl$_3$): δ 8.16 (d, J=4.5 Hz, 1H), 7.77 (s, 1H), 7.45 (q, 2H), 6.98 (t, 2H) 6.41 (d, 1H), 5.20 (d, 1H), 4.66 (s,1 H), 3.05, (d, 3H), 2.98 (d, 2H), 2.32 (s, 3H), 2.14 (m, 2H), 2.01 (m, 4H).

In methods analagous to those described above the following compound may be prepared:

EXAMPLE 80

5-[4-(2-N-Methylamino)pyrimidinyl}-4-(4-fluorophenyl)-1-(4-piperidine)imidazole

In an alternative synthesis the title compound may be prepared as follows:

5-[4-(2- N-Methylamino)pyrimidinyl}-4-(4-fluorophenyl)-1-(4-piperidine)-imidazole a) 5-[4-(2-N-Methylamino)pyrimidinyl}-4-(4-fluorophenyl)-1-(4-N-Boc-piperidine)-imidazole A solution of 2-methylamino-4-pyrimidine carboxaldehyde (2.47 g, 17.99 mmol) and t-butyl 4-amino-1-piperidine carboxylate (as described in example 46 (a)), (3.96 g, 19.79 mmol) in 36 mL of DMF was stirred at about 25° C. for about 5 to 6 h. After cooling to about 0° C., the isonitrile of step (b), Example 85 (b) (6.24 g, 21.60 mmol) and powdered K$_2$CO$_3$ (2.98 g, 21.60 mmol) were added. The solution was gradually warmed to about 25° C. over about 3 h. After about 16 h, 100 mL of H$_2$O was added and the resulting mixture was filtered, washed with 20 mL of H$_2$O and 50 mL of t-butyl methyl ether. After drying, 6.85 g (84%) of the title product was obtained as a white powder. $^1$H NMR (300 MHz, CDCl$_3$) δ 8.15 (1H, d, J=5.0 Hz), 7.72 (1H, s), 7.45 (2H, m), 6.99 (2H, t, J=8.7 Hz), 6.40 (1H, d, J=5.1 Hz), 5.20 (1H, m), 4.80 (1H, m), 4.28 (2H, m), 3.03 (3H, d, J=5.0 Hz), 2.76 (2H, t, J=12.2 Hz), 2.17 (2H, d, J=12.2 Hz), 1.86 (2H, dq, 1=4.3, 12.4 Hz), 1.48 (9H, s).

b) 5-[4-(2-N-Methylamino)pyrimidinyl}-4-(4-fluorophenyl)-1-(4-piperidine)imidazole To a stirred suspension of the N-BOC derivative of Step (a) above, (31 g, 68 mmoles) in ethyl acetate (310 mL, 10 volumes) was added 3N aqueous HCl (160 mL, 476 mmoles, 7 equiv.) at 25° C. The resulting cloudy yellow solution was stirred at 25° C. for 2 hours. The pH of the reaction mixture was adjusted to 12–13 by the slow addition of 50% aqueous NaOH. The phases were separated and the aqueous was extracted twice with methylene chloride (200 mL each). The combined organic extracts were washed with water, dried over MgSO$_4$ and rotary evaporated to dryness. The resulting light-yellow residue was slurred in hot ethyl acetate/methylene chloride (200 mL of a 9:1 mixture) and allowed to cool to 25° C. The product was collected by suction filtration and rinsed with ethyl acetate (25 mL). The white solid was dried to a constant weight at 50° C./<1 mm to give 19 g (54 mmoles) of the desired titled product, affording a 79% yield. $^1$H NMR (300 MHz, CDCl$_3$) δ 8.15 (1H, d, J=5.0 Hz), 7.77 (1H, s), 7.45 (2H, m), 6.99 (2H, t, J=8.7 Hz), 6.40 (1H, d, J=5.1 Hz), 5.23 (1H, m), 4.76 (1H, m), 3.22 (2H, d, J=12.4 Hz), 3.05 (3H, d, J=5.1 Hz), 2.67 (2H, dt, J=2.0, 12.3 Hz), 2.15 (2H, d, J=11.8 Hz), 1.86 (2H, dq, 1=3.9, 12.2 Hz).

EXAMPLE 81

5-[(2-Ethylamino)pyrimidin-4-yl]-4-(4-fluorophenyl)-1-(1-methylpiperdin-4-yl)imidazole a) 2-Methylthiopyrimidine-4-carboxaldehyde dimethyl acetal Pyruvaldehyde dimethyl acetal (19.2 mL, 159.1 mmol) and N,N-dimethylformamide dimethyl acetal (21.12 mL, 159.1 mmol) were combined in a 500 mL flask and heated at 100° C. After 4.5 h the flask was removed from the heat, thiourea (11.0 g, 144.5 mmol), NaOMe (25 wt. % solution in MeOH, 39.7 mL, 173 mmol) and 30 mL of MeOH were added and heating was continued at 65° C. After 18 h the solution was cooled to 25° C. and MeI (10.8 mL, 173 mmol) was added over 5 min (exothermic). After 3 h, the solution was diluted with 250 mL of H$_2$O and extracted with EtOAc (3×100 mL). The organics were combined, dried over N$_2$SO$_4$ and concentrated to give the title compound (26.8 g, 93%) as a brown oil.

b) 2-Methylthiopyrimidine-4-carboxaldehyde

2-Methylthiopyrimidine-4-carboxaldehyde dimethyl acetal (30.0 g, 150 mmol) was dissolved in 300 mL of glacial AcOH and 3 mL of conc. H$_2$SO$_4$ and heated at 80° C. After 10 h, the solution was cooled to 25° C. and the AcOH was removed in vacuo, leaving a brown oil residue. This residue was diluted in 200 mL of CH$_2$Cl$_2$ and washed with saturated NaHCO$_3$ (3×50 mL), H$_2$O (50 mL) and brine (50 mL). The organics were dried over MgSO$_4$ and concentrated to yield 22.1 g (96%) of the title compound as a brown oil.

c) 2-Methylthio pyrimidine-4-carboxaldehyde (1-methylpiperdin-4-yl)imine

2-Methylthiopyrimidine-4-carboxaldehyde (5.6 g, 36 mmol) and 4-amino-1-methylpiperidine dihydrochloride (6.73 g, 36 mmol) were dissolved in 200 mL of CH$_2$Cl$_2$ and NaHCO$_3$ (10.6 g, 126 mmol) was added.After 20 h, the solution was filtered and concentrated to yield 8.9 g (98%) of the title compound as a brown oil.

d) 4-(Fluorophenyl)-1-(methyl-4-piperidinyl)-5-(2-methylthio-4-pyrimidinyl)imidazole t-BuNH$_2$ (3.90 mL, 37.08 mmol) was added rapidly to a solution of 2-methylthiopyrimidine-4-carboxaldehyde (1-methylpiperdin-4-yl)imine (3.71 g, 14.83 mmol) and 4-fluorophenyl-2tosylmethylisocyanide (5.15 g, 17.8 mmol) dissolved in 50 mL of DME at 25° C. After 14 h, the solution was diluted with 50 mL of EtOAc and washed with 50 mL of sat. NaHCO$_3$ and 25 mL of brine. The organics were dried over N$_2$SO$_4$ and concentrated. Crystallization from the crude residue using EtOAC/hexanes yielded 2.85 g (50%) of the product as a light brown crystal. $^1$H NMR (CDCl$_3$, 300 MHz) δ 8.31 (1H, d, J=5.1 Hz), 7.78 (1H, s), 7.40 (2H, m), 6.99 (2H, t, J=8.7 Hz), 6.76 (1H, d, J=5.2 Hz), 4.67 (1H, m), 2.97 (2H, m), 2.58 (3H, s), 2.31 (3H, s), 2.06 (6H, m).

e) 4-(Fluorophenyl)-1-(methyl-4-piperidinyl)-5-(2-methysulfinyl-4-pyrimidinyl)imidazole Potassium persulfate (3.2 g, 7.0 mmol) in water (75 mL) was added to a solution of 4-(fluorophenyl)-1-(methyl-4-piperidinyl)-5-(2-methylthio-4-pyrimidinyl)imidazole (2.7 g, 7.0 mmol) in glacial AcOH (150 mL). After stirring at ambient temperature for 72 h, the reaction mixture was neutralized by the portion-wise addition of concentrated aqueous NH$_4$OH and extracted with CH$_2$Cl$_2$. The organic extract was washed with brine, dried (MgSO$_4$) and concentrated. The residue was triturated with ethyl ether to afford the title compound as an off-white solid; yield 2.3 g (83%).

f) 5-[(2-Ethylamino)pyrimidin-4-yl]-4-(4-fluorophenyl)-1-(1-methylpiperdin-4-yl)imidazole 4-(Fluorophenyl)-1-(methyl-4-piperidinyl)-5-(2-methylsulfinyl-4-pyrimidinyl)imidazole (0.25 g, 0.65 mmol) and 70% aqueous ethylamine (2.5 mL) were heated to 120° C. in a sealed reaction vessel for 18 h. After cooling to ambient temperature, volatiles were evaporated and the residue was triturated with ethyl ether to afford the title compound as a white solid; yield 0.13 g (53%): ES (+) MS m/e=381 (MH+).

EXAMPLE 82

4-(4-Fluorophenyl)-5-[2-(isopropyl) aminopyrirnidiny-4-yl]-1-(1-methylpiperdin-4-yl) imidazole Following the procedure of example 81, step (f) except substituting isopropylamine afforded the title compound as a tan solid in 20% yield: ES (+) MS m/e =395 (MH+).

EXAMPLE 83

5-(2-Amino-4-pyrimidinyl)-4-(4-fluorophenyl)-1-(1-methyl-4-piperdinyl)imidazole a) 2-Acetamidopyrimidine-4-carboxaldehyde monomethyl monoacetoxy acetal A mixture of 2-aminopyrimidine-4-carboxaldehyde dimethyl acetal (9.0 g, 53 mmol) and acetic anhydride (25 mL) was heated to 60° for 18 h. Concentrated H$_2$SO$_4$ (10 drops) was added and the solution was heated to 100° for 10 h. After cooling to ambient temperature, the volatiles were evaporated and the residue was vacuum filtered through a pad of silica gel eluting with 4% MeOH in CH$_2$Cl$_2$. Evaporation of the filtrate followed by trituration of the residue with ether afforded the title compound as a white solid; yield 8.6 g (68%).

b) 2-Acetamidopyrimidine-4-carboxaldehyde

Sodium methoxide (0.056 g, 1.0 mmol) was added to a solution of 2-acetamido-pyrimidine-4-carboxaldehyde monomethyl monoacetoxy acetal (5.0 g, 21 mmol) in MeOH (25 mL) at ambient temperature. After stirring at this temperature for 3 h, the reaction mixture was neutralized by addition of 3N HCl. The resulting solution was concentrated and the residue was treated with CH$_2$Cl$_2$. Remaining solids were removed by filtration and the solvent was evaporated to afford the title compound as a yellow solid; yield 3.2 g (92%).

c) 2-Acetamidopyrimidine-4-carboxaldehyde (1-methylpiperdine-4-yl)imine

Following the procedure of example 75(b) except substituting 2-acetamidopyrimidine-4-carboxaldehyde afforded the title compound as off-white solid in 75% yield.

d) 5-(2-Acetamido-4-pyrimidinyl)-4-(4-fluorophenyl)-1-(1-methyl-4-piperdinyl)imidazole Following the procedure of example 81(d) except substituting 2-acetamidopyrimidine-4-carboxaldehyde (1-methylpiperdine-4-yl)imine afforded the title compound as yellow solid in 51% yield.

e) 5-(2-Amino-4-pyrimidinyl)-4-4(4-fluorophenyl)-1-(1-methyl-4-piperdinyl)imidazole A solution of 5-(2-acetamido-4-pyrimidinyl)-4-(4-fluorophenyl)-1-(1-methyl-4-piperdinyl)imidazole (4.0 g, 0.010 mol) in 40 mL of 3N HCl was heated to 75° C. for 18 h. After cooling to ambient temperature, the reaction mixture was neutralized with solid sodium hydrogen carbonate. The resulting precipitate was isolated by filtration, washed with water and air dried to afford the title compound as a white solid in quatitative yield.

EXAMPLE 84

5-(2-Acetamido-4-pyrimidinyl)-4-(4-fluorophenyl)-1 -(4-N-morpholino-1-propyl)imidazole A solution of 5-(2-amino-4-pyrimidinyl)-4-(4-fluorophenyl)-1-(4-N-morpholino-1-propyl)imidazole (0.50 g, 1.3 mmol) in acetic anhydride (10 mL) was heated to reflux for 18 h. After cooling to ambient temperature, excess acetic anhydride was evaporated and the residue was partitioned between saturated aqueous NaHCO$_3$ and ethyl acetate. The layers were separated and the organic phase was concentrated. The residue was dissolved in MeOH (10 mL) and 2.5N NaOH (1 mL) was added. After stirring at ambient temperature for 2 h, the solution was partially evaporated and the resulting precipitate was collected by filtration, washed with water and air-dried to afford the title compound as a white solid; yield 0.28 g (51%): ES (+) MS m/e=425 (MH+).

EXAMPLE 85 a) α-(p-Toluenesulfonyl)-4-fluorobenzylformamide

To a stirred solution of 4-fluorobenzaldehyde (124 g, 979 mmoles) in acetonitrile (620 mL, 5 volumes) and toluene (620 mL, 5 volumes) was added formamide (110 g, 2.45 moles, 2.5 equiv.) followed by chlorotrimethylsilane (119 g, 1.07 moles, 1.1 equiv.). The reaction was heated at 50° C. under nitrogen for 5 hours. To the resulting white slurry was added p-toluenesulfinic acid (230 g, 1.47 moles, 1.5 equiv.) and the reaction was heated at 50° C. for an additional 5 hours then Cooled to ambient temperature. Methanol (250 mL) and t-butyl methyl ether (620 mL). were added. After 15 minutes the reaction was poured into water (3 L) precooled to 0° C. After stirring for 30 minutes at 0° C., the product was collected by suction filtration and rinsed with t-butyl methyl ether (250 mL). The product, a white, crystalline solid, was dried to a constant weight at 40° C./<1 mm Hg to afford 270 g (879 mmoles) of desired product (90% yield). $^1$H NMR (300 MHz, CD$_3$CN) δ 7.99 (1H, s), 7.92 (1H, m), 7.71 (2H, d, J=8.3 Hz), 7.49 (2H, dd, J=5.3, 8.8 Hz), 7.39 (2H, d, J=8.1 Hz), 7.16 (2H, t, J=8.8 Hz), 6.31 (1H, d, J=10.6 Hz), 2.42 (3H, s).

b) α-(p-Toluenesulfonyl)-4-fluorobenzylisonitrile

A stirred suspension of cc-(p-toluenesulfonyl)-4-fluorobenzylformamide produced in step (a) above, (100 g, 325 mmoles) in THF (650 mL, 6.5 volumes) was cooled to 0° C. and POCl₃ (46 mL, 487 mmoles, 1.5 equiv.) was added. A 1° C. exotherm was observed. After 15 minutes at 0° C., the white slurry was cooled to −5° C. Triethylamine (166 g, 1.62 moles, 5 equiv.) was added dropwise to the slurry over 45 minutes at such a rate to keep the reaction temperature below 0° C. but above −5° C. Caution should be exercised at the beginning of the addition because the reaction has a tendency to exotherm quickly. After complete addition, the yellow slurry was stirred for 30 minutes at 0° C. The reaction slurry has a tendency to darken during the stirring period. The reaction was poured into a mixture of saturated aqueous sodium bicarbonate (1 L) and ethyl acetate (1 L), both pre-cooled to 0° C. The organic phase was subsequently washed with water followed by brine. The organic phase was concentrated under vacuum via rotary evaporation until about 10% of the initial volume remained. 1-Propanol (200 mL) was added and concentrated again under vacuum at 35° C. until about 10% of the initial volume remained. This process was repeated with fresh 1-propanol (200 mL). A fine, yellow precipitate was observed. The precipitate was cooled to 0° C. and the product was collected by suction filtration and rinsed with 1-propanol (50 mL). The off-white solid was dried to a constant weight at 40° C./<1 mm to give 65.7 g (227 mmoles) of desired product, affording a 70% yield. $^1$H NMR (300 MHz, CDCl₃) δ 7.62 (2H, d, J=6.7 Hz), 7.46 (4H, m), 7.08 (2H, t, J=8.6 Hz), 5.62 (1H, s), 2.46 (3H, s).

EXAMPLE 86

5-(2-Acetamido-4-pyrimidinyl)-4-(4-fluorophenyl)-1-(1-methyl-4-piperidinyl)-imidazole To a solution of the 2-acetyamido pyrimidinyl-4-carboxaldehyde (0.84 g, 5.08 mmol) and 1-methylpiperidin-4-yl-amino dihydrochloride salt (1.04 g, 5.59 mmol) in 21 mL of DMF was added powdered K₂CO₃ (1.54 g, 11.2 mmol). After approx 6 h, the α-(p-Toluenesulfonyl)-4-fluorobenzylisonitrile, produced in Step (b) Example 85 above, (1.76 g, 6.10 mmol) and powdered K₂CO₃ (0.84 g, 6.10 mmo) were added and the sides of the flask rinsed with 5 mL of DMF. After 16 h, 300 mL of H₂O were added to the reaction mixture and the solution was extracted with EtOAc (3×100 mL). The combined organics were washed with H₂O (3×50 mL), dried over N₂SO₄ and concentrated. The pure title compound (0.75 g, 38%) was recrystallized from EtOAc as a pale yellow crystal. $^1$H NMR (300 MHz, CDCl₃) δ 8.71 (1H, s), 8.39 (1H, d, J=5.2 Hz), 7.81 (1H, s), 7.39 (2H, m), 7.13 (2H, t, J=8.7 Hz), 6.81 (1H, d, J=5.2 Hz), 4.88 (1H, m), 2.94 (2H, d, J=10. I Hz), 2.47 (3H, s), 2.32 (3H, s), 2.07 (6H, m).

EXAMPLE 87

5-[4-(2-N-Methylthioamino)pyrimidinyl}-4-(4-fluorophenyl)-1-(4-piperidine)imidazole To a solution of the 2-methylthio amino-4-pyrimidine carboxaldehyde (3.4 g, 22.07 mmol) and 4-amino-1-methyl piperidine dihydrochloride salt (4.54 g, 24.3 mmol) in 44 mL. of DMF was added K₂CO₃ (7.02 g, 50.8 mmol). After about 6 h, the solution was cooled to about 0° C. and the isonitrile of Example 85 step C.) (7.68 g, 26.5 mmol) and K₂CO₃ (3.57 g, 25.38 mmol) were added and stirred with gradual warming to about 25° C. After about 16 h, the reaction mixture was diluted with 200 mL of EtOAc and washed with 200 mL of H₂O. The aqueous layer was extracted .with EtOAc (2×100 mL) and the combined organics were washed with H₂O (3×100 mL). The organics were dried over N₂SO₄ and concentrated and the titled product was recrystallized from EtOAc/Hex to give 5.12 g (61%) of a pale yellow crystal. $^1$H NMR (300 MHz, CDCl₃) δ 8.33 (1H, d, J=5.3 Hz), 7.79 (1H, s), 7.41 (2H, m), 7.01 (2H, t, J=8.7 Hz), 6.77 (2H, d, J =5.2 Hz), 4.68 (1H, m), 2.98 (2H, m), 2.59 (3H, s), 2.32 (3H, s), 2.07 (6H, m).

EXAMPLE 88

5-[4-(2-N-Methylamino)pyrimidinyl}-4-(4-fluorophenyl)-1-(4-N-methyl-piperidine)imidazole To a solution of the 2-methylamino-4-pyrimidine carboxaldehyde (2.79 g, 20.37 mmol) and 4-amino-1-methyl piperidine dihydrochloride salt (4.19 g, 22.41 mmol) in 41 mL of DMF was added powdered K₂CO₃ (6.19 g, 44.82 mmol). The mixture was stired at room temperature for about 6 h. The solution was cooled to about 0° C. and the isonitrile of Example 85, step (b) (7.07 g, 24.44 mmol) and powdered K₂CO₃ (3.10 g, 22.41 mmol) were added. Stir at about 0° C. for about 3 h, then slowly warm to room temperature over about 2 h. Add 100 mL of H₂O and stir for about 15 min. Filter the solution and wash with 50 mL of H₂O and 50 mL of TBME. After drying, 5.56 g (74%) of the titled compound was isolated as an off-white powder. $^1$H NMR (300 MHz, CDCl₃) a 8.15 (1H, d, J=4.9 Hz), 7.76 (1H, s), 7.45 (2H, m), 6.99 (2H, t, J=8.7 Hz), 6.40 (1H, d, J=5.1 Hz), 5.29 (1H, m), 4.65 (1H, br s), 3.04 (3H, d, J=5.1 Hz), 2.97 (2H, m), 2.31 (3H, s), 2.13–1.98 (6H, m).

EXAMPLE 89

5-[4-(2-Aminopyrimidinyl)]-4-(4-fluorophenyl)-1-(2,2,6,6-tetramethyl-4-piperidinyl)imidazole a) 2-Aminopyrimidine-4-carboxaldehyde 4-(2,2,6,6-tetramethylpiperidinyl)imine The compound of example 41(b) (0.752 g, 6.1 mmol), 4-Amino-2,2,6,6-tetramethylpiperidine (1.00 g, 6.42 g), CH₂Cl₂ (90 mL), and CH₃OH (1 mL) were combined, stirred overnight and concentrated to afford the title compound as a yellow solid.

b) 5-[4-(2-amino)pyrimidinyl}-4-(4-fluorophenyl)-1-(2,2,6,6-tetramethyl-4-piperidinyl)imidazole The product of example 89(a) the product of example 79(b) (1.86 g, 6.42 mmol), K₂CO₃ (0.842 g, 6.1 mmol), and DMF (12 mL), were combined and stirred for 3 days. Poured into H₂O (25 mL) and extracted with EtOAc (4×25 mL) dried (N₂SO₄) and concentrated to an oil. Flash chromatography (0–10% MeOH in CH₂Cl₂) afforded 0.837 g (35%) of the title compound. mp=227–230 (dec).

EXAMPLE 90

In methods analogous to those described above except using the compound of example 78(b) as the aldehyde precursor to the imine the following compound may be prepared:

5-[4-(2-N-Methylamino-4-pyrimidinyl)]-4-(4-fluorophenyl)-1-(2,2,6,6-tetramethyl-4-piperidine)imidazole mp=184°185.

In methods analogous to those described in example 1 except using the product of example of example 41(b) or the product of example 78(b) as the aldehyde and the appropriate amine to afford the imine intermediate, the following compounds may be prepared:

EXAMPLE 91

5-(2-Amino-4-pyrimidinyl)-4-(4-fluorophenyl)-1-(tetrahydro-4-thiopyranyl)imidazole mp=228–230.

EXAMPLE 92

5-(2-Amino4-pyrimidinyl)-4-(4-fluorophenyl)-1-(tetrahydro-4-pyranyl)imidazole mp=222–223

EXAMPLE 93

5-(2-Methylamino-4-pyrimidinyl)-4-(4-fluorophenyl)-1-(2-cyanoethyl)imidazole mp=193–194.

In methods analogous to those described in example 14 except using the product of example of example 91 as starting material, the following compound may be prepared:

EXAMPLE 94

5-(2-Amino-4-pyrimidinyl)-4-(4-fluorophenyl)-1-(tetrahydro-4-sulfinylpyranyl)imidazole mp=255–265 (dec)

EXAMPLE 95

5-(2-Amino-4-pyrimidinyl)-4-(4-fluorophenyl)-1-(tetrahydro-4-sulfonylpyranyl)imidazole The product of example 91 (213 mg, 0.6 mmol), $CH_2Cl_2$ (2.25 mL), $CH_3OH$ (0.75 mL), and TFA (92 mL, 1.2 mmol) were cooled to 4° and MCPBA (ca. 80%) (387 mg) was added, warmed to 23°, over 20 min, poured into EtOAc (50 mL), and washed with 5% aq $N_2CO_3$, dried ($N_2SO_4$), concentrated, filtered through a plug of silica (0–4% MeOH), afforded pure 5-(2-amino-4-pyrimidinyl}-4-(4-fluorophenyl)-1-(tetrahydro-4-sulfonylpyranyl)imidazole (SB 226880) (80 mg, 34%). mp=228–230.

In methods analogous to those described in example 80 except using 1-(2,2,2-trifluoroethyl)-4-aminopiperidine as the appropriate amine to afford the amine intermediate, the following compound may be prepared:

EXAMPLE 96

5-(2-Methylamino-4-pyrimidinyl)-4-(4-fluorophenyl)-1-(2,2,2-trifluoroethyl-4-piperidinyl)imidazole mp=189–191.

EXAMPLE 97

5-(2-Amino-4-pyrimidinyl}-4-(4-fluorophenyl)-1-(trifluoroacetyl-4-piperidinyl)imidazole The product of example 46(c) (500 mg, 1.12 mmol) was suspended in $CH_2Cl_2$ (50 mL), and $Et_3N$ (585 mL, 4.2 mmol)was added and after 30 sec trifluoroacetic anhydride (160 mL, 1.12 mmol) was added. After 1 h the insoluble material was filtered off and the filtrate was concentrated. The resulting white powder was filtered through a plug of silica (1–2% $CH_3OH$ in $CH_2Cl_2$ to afford 350 mg (72%) of the title compound. mp=249–250.

In methods analogous to those described in example 1 to 97 the following compounds may be prepared:

EXAMPLE 98

5-(4-Pyridyl)-4-(4-fluorophenyl)-1-(4-piperidinyl) imidazole; m.p. 185°–187.0° C.; and

EXAMPLE 99

5-(4-Pyridyl)-4-(4-fluorophenyl)-1-(1-t-butoxy carbonyl-4-piperidinyl) imidazole

EXAMPLE 100

2-thiomethylpyrimidine aldehyde 2-thiomethylpyrimidine acetal (30.0 g, 150 mmol) was dissolved in 300 ml of concentrated $H_2SO_4$ and heated to 70°–80° C. The reaction was monitored on GC/MS. After about 3.5 hours, the starting material was completely consumed and the reaction was cooled to 25° C. and AcOH was removed in vacuo, leaving a brown oil residue. This residue was diluted in 200 ml of $CH_2Cl_2$ and $NaHCO_3$ (3×50 ml), $H_2O$ and brine (50 ml). The organics were dried over $MgSO_4$ and concentrated to yield 22.1 g (96%) of a brown oil which was pure by NMR.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A process for preparing a compound of Formula (I).

$R_1$ is a pyrimidinyl ring, which ring is optionally substituted with one or two substituents each of which is independently selected from $C_{1-4}$ alkyl, halogen, hydroxyl, $C_{1-4}$ alkoxy; $C_{1-4}$ alkylthio, $C_{1-4}$ alkylsulfinyl, $CH_2OR_{12}$, amino, mono and di- $C_{1-6}$ alkyl substituted amino, $N(R_{10})$ $C(O)R_a$ or an N-heterocyclyl ring which ring has from 5 to 7 members and optionally contains an additional heteroatom selected from oxygen, sulfur or $NR_{15}$;

$R_4$ is phenyl, naphth-1-yl or naphth-2-yl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —C(Z)NR₇R₁₇, —C(Z)OR₁₆, —(CR₁₀R₂₀)ᵥCOR₁₂, —SR5, —SOR5, —OR₁₂, halo-substituted-$C_{1-4}$ alkyl, $C_{1-4}$ alkyl, —ZC(Z)R₁₂, —NR₁₀C(Z)R₁₆, or —(CR₁₀R₂₀)ᵥNR₁₀R₂₀ and which, for other positions of substitution, is halogen, cyano, —C(Z)NR₁₃R₁₄, —C(Z)OR₃, —(CR₁₀R₂₀)ₘ‴COR₃, —S(O)mR₃, —OR₃, —OR₁₂, halo substituted $C_{1-4}$ alkyl, $C_{1-4}$ alkyl, —(CR₁₀R₂₀)ₘ‴NR₁₀C (Z)R₃, —NR₁₀S(O)ₘR₈, —NR₁₀S(O)ₘ·NR₇R₁₇, —ZC(Z)R₃, or —(CR₁₀R₂₀)ₘ‴NR₁₃R₁₄;

v is 0, or an integer having a value of 1 or 2;
m is 0, or the integer 1 or 2;
m' is an integer having a value of 1 or 2,
m" is 0, or an integer having a value of 1 to 5;
$R_2$ is $C_{1-10}$ alkyl $N_3$, —$(CR_{10}R_{20})_n OR_9$, heterocyclyl, heterocyclyl$C_{1-10}$alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl$C_{1-10}$alkyl, aryl, aryl$C_{1-10}$alkyl, heteroaryl, heteroaryl$C_{1-10}$alkyl, $(CR_{10}R_{20})_n OR11$, $(CR_{10}R_{20})_n S(O)_m R_{18}$, $(CR_{10}R_{20})_n NHS(O)_2 R_{18}$, $(CR_{10}R_{20})_n NR_{13}R_{14}$, $(CR_{10}R_{20})_n NO_2$, $(CR_{10}R_{20})_n CN$, $(CR_{10}R_{20})_{n'} SO_2 R_{18}$, $(CR_{10}R_{20})_n S(O)_{m'} NR_{13}R_{14}$, $(CR_{10}R_{20})_n C(Z)R_{11}$, $(CR_{10}R_{20})_n OC(Z)R_{11}$, $(CR_{10}R_{20})_n C(Z)OR_{11}$, $(CR_{10}R_{20})_n C(Z)NR_{13}R_{14}$, $(CR_{10}R_{20})_n C(Z)NR_{11}OR_9$, $(CR_{10}R_{20})_n NR_{10}C(Z)R_{11}$, $(CR_{10}R_{20})_n NR_{10}C(Z)NR_{13}R_{14}$, $(CR_{10}R_{20})_n N(OR_6)C(Z)NR_{13}R_{14}$, $(CR_{10}R_{20})_n N(OR_6)C(Z)R_{11}$, $(CR_{10}R_{20})_n C(=NOR_6)R_{11}$, $(CR_{10}R_{20})_n NR_{10}C(=NR_{19})NR_{13}R_{14}$, $(CR_{10}R_{20})_n OC(Z)NR_{13}R_{14}$, $(CR_{10}R_{20})_n NR_{10}C(Z)NR_{13}R_{14}$, $(CR_{10}R_{20})_n NR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl; wherein the cycloalky, cycloalkyl, alkyl, aryl, arylalkyl, heteroaryl, heteroaryl alkyl, heterocyclic and heterocyclic alkyl groups may be optionally substituted;
n is an integer having a value of 1 to 10;
n' is 0, or an integer having a value of 1 to 10;
Z is oxygen or sulfur;
$R_a$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;
$R_3$ is heterocyclyl, heterocyclyl$C_{1-10}$ alkyl or $R_8$;
$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$S(O)R_5$ being —$SOH$;
$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$_{1-10}$alkyl, heterocyclyl, aroyl, or $C_{1-10}$ alkanoyl;
$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;
$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_n OR_{11}$, $(CR_{10}R_{20})_n S(O)m R_{18}$, $(CR_{10}R_{20})_n NHS(O)2R_{18}$, $(CR_{10}R_{20})_n NR_{13}R_{14}$; wherein the aryl, arylalkyl, heteroaryl, heteroaryl alkyl may be optionally substituted;
$R_9$ is hydrogen, —$C(Z)R_{11}$, optionally substituted $C_{1-10}$ alkyl, $S(O)_2 R_{18}$, optionally substituted aryl or optionally substituted aryl-$C_{1-4}$ alkyl;
$R_{10}$ and $R_{20}$ is each independently selected from hydrogen or $C_{1-4}$ alkyl;
$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;
$R_{12}$ is hydrogen or $R_{16}$;
$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;
$R_{15}$ is $R_{10}$ or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;
$R_{18}$ is $C_{1-10}$ alkyl, $C_{3-7}$ cycloalkyl, heterocyclyl, aryl, aryl 1–10alkyl, heterocyclyl, heterocyclyl-$C_{1-10}$alkyl, heteroaryl or heteroarylalkyl;
$R_{19}$ is hydrogen, cyano, $C_{1-4}$ alkyl, $C_{3-7}$ cycloalkyl or aryl; or a pharmaceutically acceptable salt thereof.
which comprises reacting a compound of Formula (II):

with a compound of Formula (III):

wherein p is 0 or 2; and $R_1$, $R_2$ and $R_4$ are as defined above in Formula (I) or are a precursor of the groups $R_1$, $R_2$, and $R_4$ and Ar is an optionally substituted phenyl group, and thereafter if necessary converting or further reacting an $R_1$, $R_2$ and $R_4$ moiety to a yield a final compound of Formula (I) having a group $R_1$, $R_2$ and $R_4$ as defined therein.

2. The process according to claim 1 wherein the reaction is performed in an inert solvent.

3. The process according to claim 2 wherein p=0.

4. The process according to claim 3 wherein the solvent is halogenated solvent, ethers, DMF, tetrahydrofuran, toluene, acetonitrile, or dimethoxyethane; or mixtures thereof.

5. The process according to claim 4 wherein the halogenated solvent is methylene chloride, chloroform, or carbon tetrachloride, and wherein the ethers are THF, DMF, diethyl ether or t-butyl methyl ether.

6. The process according to claim 3 wherein the the solvent is methylene chloride, DMF, tetrahydrofuran, toluene, acetonitrile, or dimethoxyethane.

7. The process according to claim 6 wherein the solvent is methylene chloride, tetrahydrofuran toluene, or dimethoxyethane.

8. The process according to claim 3 wherein the reaction utilizes TBD, DBU, t-butoxide, Li+, Na+ or K+ hexamethyldisilazide as a base.

9. The process according to claim 8 wherein the reaction utilizes TBD, or DBU.

10. The process according to claim 3 wherein the reaction takes places from about −20° to about 40° C.

11. The process according to claim 10 wherein the reaction takes places from about 0° to about 23° C.

12. The process according to claim 1 wherein the Ar is substituted by $C_{1-4}$alkyl, $C_{1-4}$alkoxy or halo.

13. The process according to claim 2 wherein p=2.

14. The process according to claim 13 wherein a base is used which is strong enough to deprotonate the isonitrile moiety of Formula (II).

15. The process according to claim 14 wherein the base is an amine, a carbonate, a hydride, or an alkyl or aryl lithium reagent or mixtures thereof.

16. The process according to claim 15 wherein the base is potassium carbonate, sodium hydride, or an alkyl or aryl lithium reagent or mixtures thereof.

17. The process according to claim 16 wherein the primary or secondary amine is t-butylamine, morpholine, piperidine, or pyrrolidine.

18. The process according to claim 13 wherein the solvent is a halogenated solvent, DMF, MeCN, benzene, toluene, tetrahydrofuran, DMSO, alcohol or dimethoxyethane.

19. The process according to claim 18 wherein the halogenated solvent is methylene chloride, or chloroform, and wherein the alcohol solvent is methanol or ethanol.

20. The process according to claim 10 wherein the the solvent DMF, tetrahydrofuran, MeCN, or dimethoxyethane.

21. The process according to claim 3 wherein the reaction takes places from about 0° to about 25° C.

22. The process according to claim 11 wherein the compound of Formula (III) is produced by reacting an aldehyde $R_1CHO$ with $R_2NH_2$; where $R_1$ and $R_2$, or a suitably protected $R_2$, is defined according to Formula (I).

23. The process according to claim 1 wherein the primary amine $R_2NH_2$ is an optionally substituted heterocyclic amine or a heterocyclic $C_{1-10}$alkyl amine.

24. The process according to claim 23 wherein the primary amine $R_2NH_2$ is 4-amino piperidine, 1-methyl-4-aminopiperidine, or 4-amino-2,2,6,6-tetramethyl piperidine.

25. The process according to claim 13 wherein the imine of Formula (III) is formed, in situ, by reacting an optionally substituted pyrimidine aldehyde of the formula $R_1CHO$ wherein $R_1$ is as defined for Formula (I), and $R_2$ may be suitably protected as necessary.

26. The process according to claim 25 wherein the imine formation utilizes dehydrating conditions.

27. The process according to claim 25 wherein the imine formation utilizes acid catalysis.

28. The process according to claim 25 wherein the base is added prior to the addition of the isonitrile.

29. The process according to claim 28 wherein the reagent $R_2NH_2$ is added as a salt.

* * * * *